US008092800B2

(12) United States Patent (10) Patent No.: US 8,092,800 B2
Cassone et al. (45) Date of Patent: Jan. 10, 2012

(54) ANTIBODIES AGAINST CANDIDA ANTIGENS

(75) Inventors: Antonio Cassone, Rome (IT); Flavia de Bernardis, Rome (IT); Steven Grant, Ely (GB); Haiqun Liu, Cambridge (GB)

(73) Assignee: Istituto Superiore di Sanita, Rome (IT)

( * ) Notice: Subject to any disclaimer, the term of this patent is extended or adjusted under 35 U.S.C. 154(b) by 954 days.

(21) Appl. No.: 11/886,492

(22) PCT Filed: Mar. 10, 2006

(86) PCT No.: PCT/GB2006/000843
§ 371 (c)(1),
(2), (4) Date: Sep. 17, 2007

(87) PCT Pub. No.: WO2006/097689
PCT Pub. Date: Sep. 21, 2006

(65) Prior Publication Data
US 2008/0193450 A1 Aug. 14, 2008

(30) Foreign Application Priority Data

Mar. 18, 2005 (GB) .................................. 0505489.5
Sep. 29, 2005 (GB) .................................. 0519883.3

(51) Int. Cl.
*A61K 39/00* (2006.01)
*A61K 39/395* (2006.01)
*A61K 39/38* (2006.01)
(52) U.S. Cl. ............... 424/133.1; 424/130.1; 424/131.1; 424/135.1; 424/150.1; 424/184.1
(58) Field of Classification Search ............... 424/130.1, 424/131.1, 133.1, 135.1, 150.1, 184.1
See application file for complete search history.

(56) References Cited

FOREIGN PATENT DOCUMENTS

| EP | 1 068 232 B1 | 3/2005 |
|---|---|---|
| WO | WO 2003/072736 | 9/2003 |
| WO | WO 2004/003019 A | 1/2004 |
| WO | WO 2004/081026 | 9/2004 |
| WO | WO 2005/097202 A2 | 10/2005 |
| WO | WO 2006/097689 | 9/2006 |
| WO | WO 2008/068048 | 6/2008 |

OTHER PUBLICATIONS

De Bernardis, F., et. al., "Protective Role Of Antimannan And Anti-Aspartyl Proteinase Antibodies In An Experimental Model Of *Candida albicans* Vaginitis In Rats", *Infection And Immunity*, 65(8):3399-3405 (1997).
Accession No. CQ761109, "Sequence 2 From Patent W02004003019", Database EPO Proteins [online], Mar. 2, 2004 [retrieved on Nov. 15, 2007]. Retrieved from the Internet: <URL: http://srs.ebi.ac.uk>.
Accession No. ADL92389, "New Dual-Specific Ligands, Useful In Drug Discovery And Development, Or For Diagnosing, Preventing Or Treating A Disease, Such As Cancer, Autoimmune Disease, Or Inflammatory Disease, Including Rheumatoid Arthritis or Asthma," Database Geneseq [online], May 20, 2004 [retrieved on Nov. 15, 2007]. Retrieved from the Internet: <URL: http://stnweb.cas.org>.
Accession No. CQ761116, "Sequence 9 From Patent W02004003019", Database EPO Proteins [online], Mar. 2, 2004 [retrieved on Nov. 15, 2007]. Retrieved from the Internet: <URL: http://srs.ebi.ac.uk>.
Accession No. ADL92395, "New Dual-Specific Ligands, Useful in Drug Discovery and Development, or for Diagnosing, Preventing or Treating a Disease, Such As Cancer, Autoimmune Disease, or Inflammatory Disease, Including Rheumatoid Arthritis or Asthma", Database Geneseq [online], May 20, 2004 [retrieved on Nov. 15, 2007]. Retrieved from the Internet: <URL: http://stnweb.cas.org>.
Accession No. ADS78332, "Novel Polymer-Linked Antibody Single Variable Domain, In Which Polymer Is Linked to Cysteine or Lysine Residue, Useful for Treating Inflammation, Cancer, Autoimmune Disorders, Transplantation Rejection, Pulmonary Disorder or Hepatitis", Database Geneseq [online], Dec. 16, 2004 [retrieved on Nov. 15, 2007]. Retrieved from the Internet: <http://stnweb.cas.org>.
Han, Yongmoon, et al., "Protection Against Candidiasis by an Immunoglobulin G3 (IgG3) Monoclonal Antibody Specific for the Same Mannotriose As an IgM Protective Antibody", *Infection and Immunity*, 68(3): 1649-1654 (2000).
K.E. Conrath, et al., "Camel Single-Domain Antibodies As Modular Building Units In Bispecific and Bivalent Antibody Constructs", *Journal of Biological Chemistry*, 276(10):7346-7350 (2001).
Naglik, J.R., et al., "*Candida albicans* Secreted Aspartyl Proteinases In Virulence and Pathogenesis", *Microbiology And Molecular Biology Reviews*, 67(3):400-428 (2003).
Bartolini, S., et al., "Human Hypervariable Antibody Domains Recognizing Virulence Traits of *Candida albicans* Confer Passive Protection Against Experimental Vaginal Candidiasis", *Progress Report Quinto Programma Nazionale Di Ricerca Sull'aids*, [Online], May 2, 2005 [retrieved on Sep. 16, 2007]. Retrieved from the Internet: <URL: www.unicri.it/wwk/publications/dacp/legislation/aids/sis%202005%2012%20iss%20progress%20report.pdf> p. 198.
Cassone, A. et al., "An Outline of the Role of Anti-*Candida* Antibodies Within The Context of Passive Immunization and Protection From Candidiasis", *Current Molecular Medicine*, 5(4):377-382 (2005).
Holt L.J. et al., "Domain Antibodies: Proteins For Therapy" *Trends in Biotechnology*, 21(11):484-490 (2003).
Gomez, M.J., et al., "Purification and Biochemical Characterization Of A 65-Kilodalton Mannoprotein (MP65), A Main Target of Anti-*Candida* Cell-Mediated Immune Responses in Humans", *Infection And Immunity*, 64(7):2577-2584 (1996).
Cassone, A. et al., "Production Characterization Of A Monoclonal Antibody to a Cell-Surface Glucomannoprotein Constituent of *Candida albicans* And Other Pathogenic *Candida* Species", *Journal of Medical Microbiology*, 27(4):233-238 (1988).
Magliani, W. et al., "Therapeutic Potential of Antiidiotypic Single Chain Antibodies With Yeast Killer Toxin Activity", *Nature Biotechnology*, 15:155-158 (1997).
PCT Search Report for WO 2006/097689.
Abad-Zapatero et al. (1998) "Structure of Secreted Aspartic Proteinases from *Candida*, Implications for the Design of Antifungal Agents," In; *Aspartic Proteinases*, Plenum Press, New York, pp. 297-313.

(Continued)

*Primary Examiner* — Rodney P. Swartz
(74) *Attorney, Agent, or Firm* — Greenlee Sullivan P.C.

(57) ABSTRACT

This invention relates to domain antibodies. In particular, it relates to domain antibodies (dAbs) that recognize virulence traits of *Candida* spp. and confer passive protection against candidiasis.

56 Claims, 6 Drawing Sheets

OTHER PUBLICATIONS

British Search Report in Corresponding British Application No. GB 0624500.5, Completed Mar. 28, 2007.

Cassone et al. (2004) "Passive Vaccination and Antidotes: A Novel Strategy for Generation of Wide Spectrum Protective Antibodies," *Novel Vaccination Strategies*, Kaufmann Ed, Wiley, pp. 365-386.

De Bernardis et al. (1999) "Rat Model of *Candida* Vaginal Infection," In; *Handbook of Animal Models of Infection*, Zak et al. Eds, Academic Press, New York, NY, USA, pp. 735-740.

De Bernardis et al. (2001) "Aspartyl Proteinases of *Candida albicans* and their Role in Pathogenicity," *Med. Mycol.* 39:303-313.

De Bernardis et al. (Jun. 2000) "Local Anticandidal Immune Responses in a Rat Model of Vaginal Infection by and Protection Against *Candida albicans*," *Infect. Immun.* 68(6):3297-3304.

De Bernardis et al. (Jan. 1999) "Evidence that Members of the Secretory Aspartyl Proteinase Gene Family, in Particular SAP2, are Virulence Factors for *Candida* vaginitis," *J. Infect. Dis.* 179:201-208.

De Bernardis et al. (Aug. 1, 1997) "Protective Role of Antimannan and Anti-Aspartyl Proteinase Antibodies in an Experimental Model of *Candida albicans* Vaginitis in Rats," *Infect. Immun.* 65(8):3399-3405.

Ghadjari et al. (1997) "Epitope Mapping *Candida albicans* Proteinase (SAP2)," *FEMS Immunol. Med. Microbiol.* 19:115-123.

International Search Report, Corresponding to International Application No. PCT/EP2007/011075, Mailed Jun. 5, 2008.

La Valle et al. (Oct. 1995) "Molecular Cloning and Expression of a 70-kilodalton Heat Shock Protein of *Candida albicans*," *Infect. Immun.* 63(10):4039-4045.

Magliani et al. (Mar. 2002) "New Immunotherapeutic Strategies to Control Vaginal Candidiasis," *Trends Mol. Med.* 8(3):121-126.

Nyirjesy et al. (2003) "Vulvovaginal Candidiasis," *Obst. Gynecol. Clin. North Am.* 30:671-684.

Sandini et al. (Web Release Jan. 9, 2007) "The 65kDa Mannoprotein Gene of *Candida albicans* Encodes a Putative β-Glucanase Adhesin Required for Hyphal Morphogenesis and Experimental Pathogenicity," *Cell. Microbiol.* 9(5):1223-1238.

Tacconelli et al. (2004) "Candidiasis and HIV-Protease Inhibitors: The Expected and the Unexpected," *Curr. Med. Chem.—Immun. Endoc. Metab. Agents* 4(1):49-59.

Vilanova et al. (2004) "Protection Against Systemic Candidiasis in Mice Immunized with Secreted Asparic Proteinase 2", *Immunology* 111:334-342.

SEQUENCE LISTING

```
<160> NUMBER OF SEQ ID NOS: 35

<210> SEQ ID NO 1
<211> LENGTH: 34
<212> TYPE: DNA
<213> ORGANISM: Artificial Sequence
<220> FEATURE:
<223> OTHER INFORMATION: Primer used to amplify full-length SAP2 CDS

<400> SEQUENCE: 1
gggggatcca tgtttttaaa gaatattttc attg                              34

<210> SEQ ID NO 2
<211> LENGTH: 36
<212> TYPE: DNA
<213> ORGANISM: Artificial Sequence
<220> FEATURE:
<223> OTHER INFORMATION: Primer used to amplify full-length SAP2 CDS

<400> SEQUENCE: 2
cctaagctta ggtcaaggca gaaatactgg aagcag                            36

<210> SEQ ID NO 3
<211> LENGTH: 26
<212> TYPE: DNA
<213> ORGANISM: Artificial Sequence
<220> FEATURE:
<223> OTHER INFORMATION: Primer used to amplify CaMP65

<400> SEQUENCE: 3
cccggatccc tgttcatgtt gttacc                                       26

<210> SEQ ID NO 4
<211> LENGTH: 26
<212> TYPE: DNA
<213> ORGANISM: Artificial Sequence
<220> FEATURE:
<223> OTHER INFORMATION: Primer used to amplify CaMP65

<400> SEQUENCE: 4
gggctgcagg tgcttagtta gagtaa                                       26

<210> SEQ ID NO 5
<211> LENGTH: 120
<212> TYPE: PRT
<213> ORGANISM: Homo sapiens
<220> FEATURE:
```

```
<223> OTHER INFORMATION: MP65-binding dAb

<400> SEQUENCE: 5

Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Pro Asp Tyr
            20                  25                  30

Ser Met Thr Trp Val Arg Gln Ala Pro Gly Lys Gly Leu Glu Trp Val
        35                  40                  45

Ser Leu Ile Ser Asn Ser Gly Lys Thr Thr Met Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Trp Val Asn Arg Ile Leu Gln Glu Phe Asp Tyr Trp Gly Gln
            100                 105                 110

Gly Thr Leu Val Thr Val Ser Ser
        115                 120

<210> SEQ ID NO 6
<211> LENGTH: 120
<212> TYPE: PRT
<213> ORGANISM: Homo sapiens
<220> FEATURE:
<223> OTHER INFORMATION: MP65-binding dAb

<400> SEQUENCE: 6

Asp Ile Gln Met Thr Gln Ser Pro Ser Ser Leu Ser Ala Ser Val Gly
 1               5                  10                  15

Asp Arg Val Thr Ile Thr Cys Arg Ala Ser Gln Ser Ile Ser Ala Ala
            20                  25                  30

Leu Ala Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ile Gly Arg Arg Pro Asp
                85                  90                  95

Thr Phe Gly Gln Gly Thr Lys Val Glu Ile Lys Arg Ala Ala Ala Glu
            100                 105                 110

Gln Lys Leu Ile Ser Glu Glu Asp
        115                 120

<210> SEQ ID NO 7
<211> LENGTH: 120
<212> TYPE: PRT
<213> ORGANISM: Homo sapiens
<220> FEATURE:
<223> OTHER INFORMATION: MP65-binding dAb

<400> SEQUENCE: 7

Asp Ile Gln Met Thr Gln Ser Pro Ser Ser Leu Ser Ala Ser Val Gly
 1               5                  10                  15

Asp Arg Val Thr Ile Thr Cys Arg Ala Ser Gln Ser Ile Lys Lys Lys
            20                  25                  30

Leu Ala Trp Tyr Gln Gln Lys Pro Gly Lys Ala Pro Lys Leu Leu Ile
        35                  40                  45
```

```
Tyr Asn Ala Ser His Leu Gln Ser Gly Val Pro Ser Arg Phe Ser Gly
         50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Trp Arg Arg Phe Pro Ile
                 85                  90                  95

Thr Phe Gly Gln Gly Thr Lys Val Glu Ile Lys Arg Ala Ala Ala Glu
             100                 105                 110

Gln Lys Leu Ile Ser Glu Glu Asp
         115                 120

<210> SEQ ID NO 8
<211> LENGTH: 120
<212> TYPE: PRT
<213> ORGANISM: Homo sapiens
<220> FEATURE:
<223> OTHER INFORMATION: MP65-binding dAb

<400> SEQUENCE: 8

Asp Ile Gln Met Thr Gln Ser Pro Ser Ser Leu Ser Ala Ser Val Gly
  1               5                  10                  15

Asp Arg Val Thr Ile Thr Cys Arg Ala Ser Gln Ser Ile Lys Lys Gln
             20                  25                  30

Leu Asn Trp Tyr Gln Gln Lys Pro Gly Lys Ala Pro Lys Leu Leu Ile
         35                  40                  45

Tyr Lys Ala Ser His Leu Gln Ser Gly Val Pro Ser Arg Phe Ser Gly
     50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Met Arg Val Leu Pro Ile
                 85                  90                  95

Thr Phe Gly Gln Gly Thr Lys Val Glu Ile Lys Arg Ala Ala Ala Glu
             100                 105                 110

Gln Lys Leu Ile Ser Glu Glu Asp
         115                 120

<210> SEQ ID NO 9
<211> LENGTH: 120
<212> TYPE: PRT
<213> ORGANISM: Homo sapiens
<220> FEATURE:
<223> OTHER INFORMATION: MP65-binding dAb

<400> SEQUENCE: 9

Asp Ile Gln Met Thr Gln Ser Pro Ser Ser Leu Ser Ala Ser Val Gly
  1               5                  10                  15

Asp Arg Val Thr Ile Thr Cys Arg Ala Ser Gln Ser Ile Lys Lys His
             20                  25                  30

Leu Ala Trp Tyr Gln Gln Lys Pro Gly Lys Ala Pro Lys Leu Leu Ile
         35                  40                  45

Tyr Gly Ala Ser His Leu Gln Ser Gly Val Pro Ser Arg Phe Ser Gly
     50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Trp Arg Arg Lys Pro Ile
                 85                  90                  95

Thr Phe Gly Gln Gly Thr Lys Val Glu Ile Lys Arg Ala Ala Ala Glu
             100                 105                 110
```

```
Gln Lys Leu Ile Ser Glu Glu Asp
        115                 120

<210> SEQ ID NO 10
<211> LENGTH: 120
<212> TYPE: PRT
<213> ORGANISM: Homo sapiens
<220> FEATURE:
<223> OTHER INFORMATION: MP65-binding dAb

<400> SEQUENCE: 10

Asp Ile Gln Met Thr Gln Ser Pro Ser Ser Leu Ser Ala Ser Val Gly
 1               5                  10                  15

Asp Arg Val Thr Ile Thr Cys Arg Ala Ser Gln Ser Ile Lys Lys Gln
            20                  25                  30

Leu Asn Trp Tyr Gln Gln Lys Pro Gly Lys Ala Pro Lys Leu Leu Ile
        35                  40                  45

Tyr Lys Ala Ser His Leu Gln Ser Gly Val Pro Ser Arg Phe Ser Gly
 50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Trp Arg Arg Phe Pro Ile
                85                  90                  95

Thr Phe Gly Gln Gly Thr Lys Val Glu Ile Lys Arg Ala Ala Ala Glu
            100                 105                 110

Gln Lys Leu Ile Ser Glu Glu Asp
        115                 120

<210> SEQ ID NO 11
<211> LENGTH: 120
<212> TYPE: PRT
<213> ORGANISM: Homo sapiens
<220> FEATURE:
<223> OTHER INFORMATION: MP65-binding dAb

<400> SEQUENCE: 11

Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Pro Ser Tyr
            20                  25                  30

Ser Met Val Trp Val Arg Gln Ala Pro Gly Lys Gly Leu Glu Trp Val
        35                  40                  45

Ser Leu Ile Ser Lys Ala Gly Ser Thr Thr Leu Tyr Ala Asp Ser Val
 50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Trp Val Asn Arg Ile Leu Gln Glu Phe Asp Tyr Trp Gly Gln
            100                 105                 110

Gly Thr Leu Val Thr Val Ser Ser
        115                 120

<210> SEQ ID NO 12
<211> LENGTH: 120
<212> TYPE: PRT
<213> ORGANISM: Homo sapiens
<220> FEATURE:
<223> OTHER INFORMATION: MP65-binding dAb
```

-continued

```
<400> SEQUENCE: 12

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Lys His Ser
            20                  25                  30

Leu Gln Trp Tyr Gln Gln Lys Pro Gly Lys Ala Pro Lys Leu Leu Ile
        35                  40                  45

Tyr Lys Ala Ser Arg Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Val Lys Arg Arg Pro Gly
                85                  90                  95

Thr Phe Gly Gln Gly Thr Lys Val Glu Ile Lys Arg Ala Ala Ala Glu
            100                 105                 110

Gln Lys Leu Ile Ser Glu Glu Asp
        115                 120

<210> SEQ ID NO 13
<211> LENGTH: 120
<212> TYPE: PRT
<213> ORGANISM: Homo sapiens
<220> FEATURE:
<223> OTHER INFORMATION: MP65-binding dAb

<400> SEQUENCE: 13

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Lys Lys Gln
            20                  25                  30

Leu Asn Trp Tyr Gln Gln Lys Pro Gly Lys Ala Pro Lys Leu Leu Ile
        35                  40                  45

Tyr Lys Ala Ser His Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Met Arg Val Leu Pro Ile
                85                  90                  95

Thr Phe Gly Gln Gly Thr Lys Val Glu Ile Lys Arg Ala Ala Ala Glu
            100                 105                 110

Gln Lys Leu Ile Ser Glu Glu Asp
        115                 120

<210> SEQ ID NO 14
<211> LENGTH: 120
<212> TYPE: PRT
<213> ORGANISM: Homo sapiens
<220> FEATURE:
<223> OTHER INFORMATION: Sap2-binding dAb

<400> SEQUENCE: 14

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Phe Ile Ala
            20                  25                  30

Leu Lys Trp Tyr Gln Gln Lys Pro Gly Lys Ala Pro Lys Leu Leu Ile
        35                  40                  45

Tyr Asn Ala Ser Val Leu Gln Ser Gly Val Pro Ser Arg Phe Ser Gly
```

```
                50                  55                  60
Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Gln Ser Arg Lys Pro Gln
                 85                  90                  95

Thr Phe Gly Gln Gly Thr Lys Val Glu Ile Lys Arg Ala Ala Ala Glu
                100                 105                 110

Gln Lys Leu Ile Ser Glu Glu Asp
            115                 120

<210> SEQ ID NO 15
<211> LENGTH: 120
<212> TYPE: PRT
<213> ORGANISM: Homo sapiens
<220> FEATURE:
<223> OTHER INFORMATION: Sap2-binding dAb

<400> SEQUENCE: 15

Glu Val Gln Leu Leu Glu Ser Gly Gly Gly Leu Val Gln Pro Gly Gly
  1               5                  10                  15

Ser Leu Arg Leu Ser Cys Ala Ala Ser Gly Phe Thr Phe Ala Gln Tyr
                 20                  25                  30

Arg Met Ala Trp Val Arg Gln Ala Pro Gly Lys Gly Leu Glu Trp Val
             35                  40                  45

Ser Gln Ile Asn Ala Gln Gly Thr Gln Thr Gly Tyr Ala Asp Ser Val
         50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Lys Trp Val Gly Ala Arg Tyr Thr Phe Asp Tyr Trp Gly Gln
                100                 105                 110

Gly Thr Leu Val Thr Val Ser Ser
            115                 120

<210> SEQ ID NO 16
<211> LENGTH: 120
<212> TYPE: PRT
<213> ORGANISM: Homo sapiens
<220> FEATURE:
<223> OTHER INFORMATION: Sap2-binding dAb

<400> SEQUENCE: 16

Glu Val Gln Leu Leu Glu Ser Gly Gly Gly Leu Val Gln Pro Gly Gly
  1               5                  10                  15

Ser Leu Arg Leu Ser Cys Ala Ala Ser Gly Phe Thr Phe Leu Asp Tyr
                 20                  25                  30

Gln Met Ser Trp Val Arg Gln Ala Pro Gly Lys Gly Leu Glu Trp Val
             35                  40                  45

Ser Gly Ile Ser Arg Ser Gly Asn Lys Thr Lys Tyr Ala Asp Ser Val
         50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Lys Trp Ala Gly Leu Asn Arg His Asp Phe Asp Tyr Trp Gly Gln
                100                 105                 110

Gly Thr Leu Val Thr Val Ser Ser
```

<210> SEQ ID NO 17
<211> LENGTH: 123
<212> TYPE: PRT
<213> ORGANISM: Homo sapiens
<220> FEATURE:
<223> OTHER INFORMATION: Sap2-binding dAb

<400> SEQUENCE: 17

Glu Val Gln Leu Leu Glu Ser Gly Gly Gly Leu Val Gln Pro Gly Gly
 1               5                  10                  15

Ser Leu Arg Leu Ser Cys Ala Ala Ser Gly Asp Arg Ile Ser Ser Glu
            20                  25                  30

Phe Met Gly Trp Val Arg Gln Ala Pro Gly Lys Gly Leu Glu Trp Val
        35                  40                  45

Ser Ala Ile Tyr Lys Pro Asn Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Arg Ala Arg Arg Thr Glu Ser Thr Tyr Gln Leu Arg Tyr
            100                 105                 110

Trp Gly Gln Gly Thr Leu Val Thr Val Ser Ser
        115                 120

<210> SEQ ID NO 18
<211> LENGTH: 123
<212> TYPE: PRT
<213> ORGANISM: Homo sapiens
<220> FEATURE:
<223> OTHER INFORMATION: Sap2-binding dAb

<400> SEQUENCE: 18

Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Arg Val Ser Asn Tyr
            20                  25                  30

Asp Leu Thr Trp Val Arg Gln Ala Pro Gly Lys Gly Leu Glu Trp Val
        35                  40                  45

Ser Thr Ile Ser Ala Thr Asn Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Ala Val Thr Trp Trp Leu Leu Arg His Asn Asp Asn Leu Gly Phe
            100                 105                 110

Trp Gly Gln Gly Thr Leu Val Thr Val Ser Ser
        115                 120

<210> SEQ ID NO 19
<211> LENGTH: 123
<212> TYPE: PRT
<213> ORGANISM: Homo sapiens
<220> FEATURE:
<223> OTHER INFORMATION: Sap2-binding dAb

<400> SEQUENCE: 19

-continued

```
Glu Val Gln Leu Leu Glu Ser Gly Gly Gly Leu Val Gln Pro Gly Gly
 1               5                  10                  15

Ser Leu Arg Leu Ser Cys Ala Ala Ser Gly Tyr Ser Val Thr Tyr Gln
             20                  25                  30

Asn Met Ala Trp Val Arg Gln Ala Pro Gly Lys Gly Leu Glu Trp Val
         35                  40                  45

Ser Thr Ile Thr Val Pro Asn Gly Ser Thr Tyr Tyr Ala Asp Ser Val
     50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Gly Leu Gly Glu Val Leu Arg Asp Gly Asn Ala Asn Val Gln Phe
            100                 105                 110

Trp Gly Gln Gly Thr Leu Val Thr Val Ser Ser
            115                 120
```

<210> SEQ ID NO 20
<211> LENGTH: 123
<212> TYPE: PRT
<213> ORGANISM: Homo sapiens
<220> FEATURE:
<223> OTHER INFORMATION: Sap2-binding dAb

<400> SEQUENCE: 20

```
Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Ser Leu Ser Tyr Lys
             20                  25                  30

Val Met Gly Trp Val Arg Gln Ala Pro Gly Lys Gly Leu Glu Trp Val
         35                  40                  45

Ser Ala Ile Asn Arg Glu Asn Gly Ser Thr Tyr Tyr Ala Asp Ser Val
     50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Gly Phe Ala Arg Arg Gly Ala Pro His Ser Ala Ser Val Glu Phe
            100                 105                 110

Trp Gly Gln Gly Thr Leu Val Thr Val Ser Ser
            115                 120
```

<210> SEQ ID NO 21
<211> LENGTH: 119
<212> TYPE: PRT
<213> ORGANISM: Homo sapiens
<220> FEATURE:
<223> OTHER INFORMATION: Sap2-binding dAb

<400> SEQUENCE: 21

```
Glu Val Gln Leu Leu Glu Ser Gly Gly Gly Leu Val Gln Pro Gly Gly
 1               5                  10                  15

Ser Leu Arg Leu Ser Cys Ala Ala Ser Gly Val Arg Leu Ser His Gln
             20                  25                  30

Val Met Gly Trp Val Arg Gln Ala Pro Gly Lys Gly Leu Glu Trp Val
         35                  40                  45

Ser Ala Ile Arg Ser Ser Asp Gly Ser Thr Tyr Tyr Ala Asp Ser Val
     50                  55                  60
```

-continued

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Gly Trp Arg Ser Ala Lys Ser Gln Met His Tyr Trp Gly Gln Gly
            100                 105                 110

Thr Leu Val Thr Val Ser Ser
            115

<210> SEQ ID NO 22
<211> LENGTH: 128
<212> TYPE: PRT
<213> ORGANISM: Homo sapiens
<220> FEATURE:
<223> OTHER INFORMATION: Sap2-binding dAb

<400> SEQUENCE: 22

Glu Val Gln Leu Leu Glu Ser Gly Gly Gly Leu Val Gln Pro Gly Gly
1               5                   10                  15

Ser Leu Arg Leu Ser Cys Ala Ala Ser Gly Val Ser Val Ser Ala Tyr
            20                  25                  30

Thr Met Ser Trp Val Arg Gln Ala Pro Gly Lys Gly Leu Glu Trp Val
        35                  40                  45

Ser Ala Ile Leu Lys Lys Asn Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Gly Arg Pro Ser Val Thr Phe Gly Gly Pro Gly Lys Arg Tyr Asp
            100                 105                 110

Tyr His Phe Gln Tyr Trp Gly Gln Gly Thr Leu Val Thr Val Ser Ser
            115                 120                 125

<210> SEQ ID NO 23
<211> LENGTH: 127
<212> TYPE: PRT
<213> ORGANISM: Homo sapiens
<220> FEATURE:
<223> OTHER INFORMATION: Sap2-binding dAb

<400> SEQUENCE: 23

Glu Val Gln Leu Leu Glu Ser Gly Gly Gly Leu Val Gln Pro Gly Gly
1               5                   10                  15

Ser Leu Arg Leu Ser Cys Ala Ala Ser Gly Val Ile Phe Thr Asp Gln
            20                  25                  30

Thr Met Gly Trp Val Arg Gln Ala Pro Gly Lys Gly Leu Glu Trp Val
        35                  40                  45

Ser Ala Ile Lys Thr Arg Asp Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Phe Leu Arg Pro Asn Ala Ser Arg Gly Ser Ala Arg Glu Ala
            100                 105                 110

Gln Ile His Ser Trp Gly Gln Gly Thr Leu Val Thr Val Ser Ser
            115                 120                 125

```
<210> SEQ ID NO 24
<211> LENGTH: 126
<212> TYPE: PRT
<213> ORGANISM: Homo sapiens
<220> FEATURE:
<223> OTHER INFORMATION: Sap2-binding dAb

<400> SEQUENCE: 24

Glu Val Gln Leu Leu Glu Ser Gly Gly Gly Leu Val Gln Pro Gly Gly
 1               5                  10                  15

Ser Leu Arg Leu Ser Cys Ala Ala Ser Gly Asp Thr Val Ser Ser Lys
            20                  25                  30

Ala Met Ala Trp Val Arg Gln Ala Pro Gly Lys Gly Leu Glu Trp Val
        35                  40                  45

Ser Gly Ile Phe Ile Pro Asn Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Ala Lys Gln Arg Ala Val Leu Ser Arg Trp Gly Ser Ser Thr Glu
            100                 105                 110

Phe Gly Ser Trp Gly Gln Gly Thr Leu Val Thr Val Ser Ser
        115                 120                 125

<210> SEQ ID NO 25
<211> LENGTH: 121
<212> TYPE: PRT
<213> ORGANISM: Homo sapiens
<220> FEATURE:
<223> OTHER INFORMATION: Sap2-binding dAb

<400> SEQUENCE: 25

Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Ser Ile Ser Tyr Lys
            20                  25                  30

Asn Met Ala Trp Val Arg Gln Ala Pro Gly Lys Gly Leu Glu Trp Val
        35                  40                  45

Ser Ala Ile Lys Ala Ala Asn Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Thr Gly Ser Gln Lys Lys Arg Thr Tyr Thr Phe Asp Phe Trp Gly
            100                 105                 110

Gln Gly Thr Leu Val Thr Val Ser Ser
        115                 120

<210> SEQ ID NO 26
<211> LENGTH: 116
<212> TYPE: PRT
<213> ORGANISM: Homo sapiens
<220> FEATURE:
<223> OTHER INFORMATION: Sap2-binding dAb

<400> SEQUENCE: 26

Glu Val Gln Leu Leu Glu Ser Gly Gly Gly Leu Val Gln Pro Gly Gly
 1               5                  10                  15
```

```
Ser Leu Arg Leu Ser Cys Ala Ala Ser Gly Phe Thr Phe Asp Leu Tyr
            20                  25                  30

Ser Met Lys Trp Val Arg Gln Ala Pro Gly Lys Gly Leu Glu Trp Val
        35                  40                  45

Ser Gly Ile Ser Ala Asn Gly Met Ile Thr Trp Tyr Ala Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                85                  90                  95

Ala Lys Gly Trp Ala Ala Phe Asp Tyr Arg Gly Gln Gly Thr Leu Val
            100                 105                 110

Thr Val Ser Ser
        115

<210> SEQ ID NO 27
<211> LENGTH: 116
<212> TYPE: PRT
<213> ORGANISM: Homo sapiens
<220> FEATURE:
<223> OTHER INFORMATION: Sap2-binding dAb

<400> SEQUENCE: 27

Glu Val Gln Leu Leu Glu Ser Gly Gly Gly Leu Val Gln Pro Gly Gly
 1               5                   10                  15

Ser Leu Arg Leu Ser Cys Ala Ala Ser Gly Phe Thr Phe Ala Val Tyr
            20                  25                  30

Thr Met Asp Trp Val Arg Gln Ala Pro Gly Lys Gly Leu Glu Trp Val
        35                  40                  45

Ser Ser Ile Arg Pro Met Gly His Gln Thr Arg Tyr Ala Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                85                  90                  95

Ala Lys Asn Gly Glu Ile Phe Asp Tyr Trp Gly Gln Gly Thr Leu Val
            100                 105                 110

Thr Val Ser Ser
        115

<210> SEQ ID NO 28
<211> LENGTH: 120
<212> TYPE: PRT
<213> ORGANISM: Homo sapiens
<220> FEATURE:
<223> OTHER INFORMATION: Sap2-binding dAb

<400> SEQUENCE: 28

Glu Val Gln Leu Leu Glu Ser Gly Gly Gly Leu Val Gln Pro Gly Gly
 1               5                   10                  15

Ser Leu Arg Leu Ser Cys Ala Ala Ser Gly Phe Thr Phe Arg Glu Tyr
            20                  25                  30

Val Met Asp Trp Val Arg Gln Ala Pro Gly Lys Gly Leu Glu Trp Val
        35                  40                  45

Ser Gly Ile Thr Gly Asn Gly Val Ser Thr Arg Tyr Ala Asp Ser Val
 50                  55                  60

Lys Gly Arg Phe Thr Ile Ser Arg Asp Asn Ser Lys Asn Thr Leu Tyr
 65                  70                  75                  80
```

```
Leu Gln Met Asn Ser Leu Arg Ala Glu Asp Thr Ala Val Tyr Tyr Cys
                85                  90                  95

Ala Lys Ser Glu Ser Pro Gly Met Ala Ile Phe Asp Tyr Trp Gly Gln
            100                 105                 110

Gly Thr Leu Val Thr Val Ser Ser
            115                 120

<210> SEQ ID NO 29
<211> LENGTH: 120
<212> TYPE: PRT
<213> ORGANISM: Homo sapiens
<220> FEATURE:
<223> OTHER INFORMATION: Sap2-binding dAb

<400> SEQUENCE: 29

Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Arg Val Tyr
            20                  25                  30

Met Met Ala Trp Val Arg Gln Ala Pro Gly Lys Gly Leu Glu Trp Val
        35                  40                  45

Ser Lys Ile Ser Ser Gln Gly Ile Ser Thr His Tyr Ala Asp Ser Val
 50                  55                  60

Lys Gly Arg Phe Thr Ile Ser Arg Asp Asn Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Gln Ala Arg Leu Gly His Gln Ser Phe Asp Tyr Trp Gly Gln
            100                 105                 110

Gly Thr Leu Val Thr Val Ser Ser
            115                 120

<210> SEQ ID NO 30
<211> LENGTH: 116
<212> TYPE: PRT
<213> ORGANISM: Homo sapiens
<220> FEATURE:
<223> OTHER INFORMATION: Sap2-binding dAb

<400> SEQUENCE: 30

Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Gly Leu Tyr
            20                  25                  30

Ser Met Ser Trp Val Arg Gln Ala Pro Gly Lys Gly Leu Glu Trp Val
        35                  40                  45

Ser Gly Ile Leu Ala Gly Gly Ala Thr Ser Tyr Ala Asp Ser Val
 50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Gly Leu Leu Leu Phe Asp Tyr Trp Gly Gln Gly Thr Leu Val
            100                 105                 110

Thr Val Ser Ser
        115

<210> SEQ ID NO 31
```

```
<211> LENGTH: 119
<212> TYPE: PRT
<213> ORGANISM: Homo sapiens
<220> FEATURE:
<223> OTHER INFORMATION: Sap2-binding dAb

<400> SEQUENCE: 31

Glu Val Gln Leu Leu Glu Ser Gly Gly Gly Leu Val Gln Pro Gly Gly
  1               5                  10                  15

Ser Leu Arg Leu Ser Cys Ala Ala Ser Gly Phe Thr Phe Ala Asp Tyr
             20                  25                  30

Leu Met Leu Trp Val Arg Gln Ala Pro Gly Lys Gly Leu Glu Trp Val
         35                  40                  45

Ser Ala Ile Gly Ala Ser Gly Ser Ser Thr Ile Tyr Ala Asp Ser Val
     50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Lys Lys Gly Met Arg Leu Lys Gln Phe Asp Tyr Trp Gly Gln Gly
            100                 105                 110

Thr Leu Val Thr Val Ser Ser
            115

<210> SEQ ID NO 32
<211> LENGTH: 120
<212> TYPE: PRT
<213> ORGANISM: Homo sapiens
<220> FEATURE:
<223> OTHER INFORMATION: Sap2-binding dAb

<400> SEQUENCE: 32

Glu Val Gln Leu Leu Glu Ser Gly Gly Gly Leu Val Gln Pro Gly Gly
  1               5                  10                  15

Ser Leu Arg Leu Ser Cys Ala Ala Ser Gly Phe Thr Phe Ala Asp Tyr
             20                  25                  30

Leu Met Leu Trp Val Arg Gln Ala Pro Gly Lys Gly Leu Glu Trp Val
         35                  40                  45

Ser Ala Ile Gly Ala Ser Gly Ser Ser Thr Ile Tyr Ala Asp Ser Val
     50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Lys Gln Ala Arg Leu Gly His Gln Ser Phe Asp Tyr Trp Gly Gln
            100                 105                 110

Gly Thr Leu Val Thr Val Ser Ser
            115                 120

<210> SEQ ID NO 33
<211> LENGTH: 116
<212> TYPE: PRT
<213> ORGANISM: Homo sapiens
<220> FEATURE:
<223> OTHER INFORMATION: Sap2-binding dAb

<400> SEQUENCE: 33

Glu Val Gln Leu Leu Glu Ser Gly Gly Gly Leu Val Gln Pro Gly Gly
  1               5                  10                  15

Ser Leu Arg Leu Ser Cys Ala Ala Ser Gly Phe Thr Phe Gly Leu Tyr
```

```
                    20                  25                  30
Ser Met Ser Trp Val Arg Gln Ala Pro Gly Lys Gly Leu Glu Trp Val
            35                  40                  45

Ser Gly Ile Leu Ala Gly Gly Ala Thr Ser Tyr Ala Asp Ser Val
        50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Gly Asp Thr Ala Val Tyr Tyr Cys
                85                  90                  95

Ala Lys Gly Leu Leu Leu Phe Asp Tyr Trp Gly Gln Gly Thr Leu Val
            100                 105                 110

Thr Val Ser Ser
        115

<210> SEQ ID NO 34
<211> LENGTH: 120
<212> TYPE: PRT
<213> ORGANISM: Homo sapiens
<220> FEATURE:
<223> OTHER INFORMATION: Sap2-binding dAb

<400> SEQUENCE: 34

Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Gln Ser Tyr
            20                  25                  30

Ser Met Met Trp Val Arg Gln Ala Pro Gly Lys Gly Leu Glu Trp Val
            35                  40                  45

Ser Arg Ile Ser Ser Arg Gly Leu Glu Thr Tyr Tyr Ala Asp Ser Val
        50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                85                  90                  95

Ala Lys Arg Ser Arg Phe Gln Pro Arg Ser Phe Asp Tyr Trp Gly Gln
            100                 105                 110

Gly Thr Leu Val Thr Val Ser Ser
        115                 120

<210> SEQ ID NO 35
<211> LENGTH: 116
<212> TYPE: PRT
<213> ORGANISM: Homo sapiens
<220> FEATURE:
<223> OTHER INFORMATION: Sap2-binding dAb

<400> SEQUENCE: 35

Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Arg Met Tyr
            20                  25                  30

Ser Met Arg Trp Val Arg Gln Ala Pro Gly Lys Gly Leu Glu Trp Val
            35                  40                  45

Ser Ala Ile Ser Gly Ser Gly Ser Thr Tyr Tyr Ala Asp Ser Val
        50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
```

-continued

```
                85                  90                  95
Ala Lys Gly Trp Gly Ala Phe Asp Tyr Trp Gly Gln Gly Thr Leu Val
            100                 105                 110

Thr Val Ser Ser
        115
```

ANTIBODIES AGAINST *CANDIDA* ANTIGENS

RELATED APPLICATIONS

This application is the U.S. National Stage of International Application No. PCT/GB2006/000843, filed Mar. 10, 2006, published in English, and claims priority under 35 U.S.C. § 119 or 365 to United Kingdom Application No. 0505489.5, filed Mar. 18, 2005, and to United Kingdom Application No. 0519883.3, filed Sep. 29, 2005.

This invention relates to domain antibodies. In particular, it relates to domain antibodies that recognize virulence traits of *Candida* spp. and confer passive protection against candidiasis.

Passive vaccination, the therapeutic or preventative use of antibodies or antigen-reactive antibody fragments, is a remarkably attractive means for control of infectious diseases in an era of emerging and re-emerging infectious agents, increased anti-microbial resistance threat and paucity of new drugs and preventive vaccines. Passive vaccination is particularly attractive for the control of those agents of opportunistic infections which rely upon immune dysfunction to cause disease in a debilitated host. Absence or reduction of immune competence negates to the host the necessary cooperation with antimicrobials, and makes it particularly hard to generate a protective vaccine. *Candida albicans* is one such opportunistic agent for which passive vaccination appears to be particularly promising. It is a major mucosal and systemic pathogen in the setting of immunocompromised host, in particular in AIDS subjects and neutropenic, hemopathic patients undergoing bone-marrow transplantation. It is also an important pathogen in the setting of vaginal candidiasis and other mucocutaneous pathologies. In fact, it has been estimated that three quarters of all normal women in fertile age experience at least one attack of acute vaginal candidiasis, and, more importantly, about 5% of them suffer from chronic recurrences thereafter. Chronic vaginal candidiasis is hardly curable with antimycotics and there is increased concern and some clinical evidence that *Candida* may become antimycotic-refractory under repeated treatment.

*C. albicans* is essentially an extracellular pathogen, with some defined virulence traits. Studies with experimental animal models of infection have demonstrated that antibodies of the right specificity and isotypes can indeed protect against severe mucosal and systemic experimental infections, as well. Studies have particularly highlighted the virulence characteristics of one member of secretory aspartic proteases (SAP2) and a putative mannoprotein adhesin (MP65) of the fungus and laid the ground for an efficacious immunoprotection by specific polyclonal, monoclonal antibodies and peptide fragments against them.

In the perspective of immunotherapy of mucosal candidiasis of humans, the generation of humanized or human antibodies is a critical issue that has recently become more affordable by the use of recombinant DNA technology. In particular, phage expression libraries allow selection and production of human single chain-variable fragments (scFv) or single domain antibodies (dAbs) with predefined specificity, in relatively large amount and easily standardizable.

Therapeutic anti-Candida scFv antibodies have previously been generated (Magliani, W., et al., 1995 *Nat. Biotechnol.* 15: 155-158).

However, there remains in the art, a need for alternative anti-Candida antibodies which are effective in the treatment of *Candida* spp. infection.

SUMMARY OF THE INVENTION

The present inventors have generated a number of single domain antibodies (dabs) which they have shown to be effective in the treatment of *Candida* spp. infection, in particular in the treatment of vaginal candidiasis. These single domain antibodies have been shown to bind and/or inhibit the functional activity of certain *Candida* spp. virulence factors.

Thus in a first aspect the present invention provides a single domain antibody (dAb) which is capable of binding to and/or inhibiting the functional activity of a secretory aspartic protease (Sap) from *Candida* spp.

According to the invention described herein those amino acid sequences designated ADR4-X in the sequence listing provided herein represent Sap2 binding dAb amino acid sequences.

Secretory aspartic proteases for binding by one or more dAbs (dabs) according to the present invention include Sap1, Sap2, Sap3, Sap4, Sap5 and Sap6, Sap 7, Sap8, Sap9 and Sap 10 secretory aspartic proteases. In a preferred embodiment of the above aspect of the invention, the dAb is a Sap2 binding dAb (Sap2 binding dAb).

Preferably it is a Sap2 binding dAb comprising, preferably consisting of, one or more sequences shown in the sequence listing provided herein and designated ADR4-2 designated SEQ ID No 14 to ADR4-23 designated SEQ ID No 35.

In a most preferred embodiment of the above aspect of the invention, the dAb is a Sap2 binding dAb comprising, preferably consisting of, one or more sequences shown in the sequence listing provided herein and designated ADR4-6 represented by SEQ ID No 18 and ADR4-13 represented by SEQ ID No 25 herein.

Advantageously, the dAb according to the present invention binds to one or more SAPs as herein defined with a $K_{off}$ rate constant of between $5\times10^{-1}$ and $1\times10^{-7}$ s$^{-1}$.

More advantageously, the dAb according to the present invention binds to Sap2 with a dissociation constant (Kd) of at least 100 M to 1 µM.

*Candida* infections of any species may be treated using one or more dAbs according to the present invention. Suitable *Candida* spp. infections for treatment using the dAbs of the present include any of those in the group consisting of the following: *Candida ciferrii, Candida famata, Candida lambica, Candida lipolytica, Candida norvegensis, Candida rugosa, Candida viswanathii, Candida zeylanoides, Candida albicans, Candida tropicalis, Candida glabrata, Candida parapsilosis, Candida krusei, Candida lusitaniae, Candida kefyr, Candida guilliermondii* and *Candida dubliniensis*.

Preferred *Candida* spp. for treatment according to the invention include any of those in the group consisting of the following: *Candida albicans, Candida tropicalis, Candida glabrata, Candida parapsilosis, Candida krusei* and *Candida lusitaniae*.

In a most preferred embodiment of the above aspect of the invention, the *Candida* species is *Candida albicans*.

In a further aspect the present invention provides a single domain antibody (dAb) which is capable of binding to and/or inhibiting the functional activity of a secretory aspartic protease (Sap) from *Candida* spp. and which exhibits 80% identity to one or more Sap dabs provided herein.

In a preferred embodiment of the above aspect of the invention, the dAb exhibits 82, 84, 86, 88, 90, 92, 94, 96, 98 or 99% identity to one or more Sap2 dabs provided herein.

In a preferred embodiment of the above aspect of the invention, the dAb according to the present invention is capable of binding to one or more Sap proteins as herein defined with a $K_{off}$ rate constant of between $5\times10^{-1}$ and $1\times10^{-7}$ s$^{-1}$.

More advantageously, the dAb according to the above aspect of the invention is capable of binding to Sap2 with a dissociation constant (Kd) of at least 100 µM to 1 pM and/or a $K_{off}$ rate constant of between $5\times10^{-1}$ and $1\times10^{-7}$ s$^{-1}$.

In a further aspect the present invention provides a single domain antibody (dAb) which is capable of binding to and/or inhibiting the functional activity of mannoprotein adhesin (MP) from *Candida* spp.

According to the present invention, those sequences designated ADR3-X represent the sequences of mannoprotein adhesin (MP) binding dabs (MP dAbs).

According to the above aspect of the invention, advantageously the dAb is a MP65 binding dAb comprising, preferably consisting of, one or more sequences shown in the sequence listing provided herein and designated ADR3-1, ADR3-1, ADR3-3, ADR3-4, ADR3-5, ADR3-6, ADR3-7, ADR3-8, ADR3-9 and represented as SEQ ID No 5 to SEQ ID No 13 respectively.

According to the above aspect of the invention, advantageously the dAb is a MP65 binding dAb comprising, preferably consisting of, one or more sequences shown in the sequence listing provided herein and designated ADR3-1, ADR3-2 and ADR3-6 and designated SEQ ID NOs 5, 6 and 10 respectively.

Advantageously, the dAb according to the present invention is capable of binding to one or more MPs as herein defined with a $K_{off}$ rate constant of between $5 \times 10^{-1}$ and $1 \times 10^{-7}$ s$^{-1}$.

More advantageously, the dAb according to the present invention is capable of binding to MP65 with a dissociation constant (Kd) of at least 100 µM to 1 µM.

*Candida* infections of any species may be treated using one or more dAbs according to the present invention. Preferred *Candida* spp. for treatment according to the invention include any of those in the group consisting of the following: *Candida albicans, Candida tropicalis, Candida glabrata, Candida parapsilosis, Candida krusei* and *Candida lusitaniae*. In a most preferred embodiment of the above aspect of the invention, the *Candida* species is *Candida albicans*.

In a further aspect the present invention provides a single domain antibody (dAb) which is capable of binding to and/or inhibiting the functional activity of mannoprotein adhesin (MP) from *Candida* spp. and which exhibits 80% identity to those dAbs identified as ADR3-1, ADR3-2 and ADR3-6 and designated SEQ ID NOs 5, 6 and 10 respectively.

In a preferred embodiment of the above aspect of the invention, the dAb exhibits 82, 84, 86, 88, 90, 92, 94, 96, 98 or 99% identity to one or more of those dAbs identified as ADR3-1, ADR3-2 and ADR3-6 and designated SEQ ID NOs 5, 6 and 10 respectively.

In a further aspect still the present invention provides a pharmaceutical composition comprising any one or more dAbs according to the invention and a pharmaceutically acceptable carrier, diluent and/or exipient.

In a preferred embodiment of the above aspect of the invention, the pharmaceutical composition comprises, preferably consists of MP65 and Sap 2 binding dabs.

In an alternative embodiment of the above aspect of the invention, the pharmaceutical composition comprises, preferably consists of one or more dAbs which inhibit the functional activity of MP65 and Sap2.

In yet a further aspect the invention provides a method for the prophylaxis and/or treatment of *Candida* spp. infection in a patient by administering to a patient in need of such treatment one or more dAbs or a composition according to the invention.

In a further aspect still, the present invention provides a dAb according to the present invention for use in the prophylaxis and/or treatment of *Candida* spp. infection.

In a further aspect the present invention provides a method for the prophylaxis and/or treatment of azole resistant *Candida* spp. infection in a patient by administering to a patient in need of such treatment a SAP2 and/or MP65 dAb wherein the *Candida* is resistant to any one or more agent/s in the group consisting of the following: itraconazole, fluconazole and voriconazol.

In yet a further aspect still, the present invention provides a method for the treatment of imidazole resistant *Candida* spp. infection in a patient by administering to a patient in need of such treatment a Sap2 and/or MP65 dAb wherein the *Candida* spp. infection is resistant to any one or more agents in the group consisting of the following: Clotrimazole, econazole, fenticonazole, sulconazole and tioconazole.

According to the above aspects of the invention, a Sap2 or MP65 'dAb' refers to a single domain antibody as described herein which is capable of binding to and/or inhibiting the functional activity of Sap2 and/or MP65 described herein.

According to the methods and medicaments of the invention described herein, preferred *Candida* spp, infections for treatment with one or more dAbs/dAbs described herein, include but are not limited to any of those *Candida* spp. infections in the group consisting of the following: *Candida albicans, Candida tropicalis, Candida glabrata, Candida parapsilosis, Candida krusei* and *Candida lusitaniae*.

Those skilled in the art will appreciate that *Candida* spp. infections may be systemic, vaginal, dermal, oral, mucosal, bronchal, and pulmonary. Further, yeast infection may be apparent as onychomycosis (nail infection), oropharyngeal candidasis, esophageal candidasis or vulvovaginitis.

In a preferred embodiment of the invention, one or more dAbs/dAbs according to the invention is used for the prophylaxis and/or treatment of vaginal or systemic *Candida* spp. infection.

Using the methods and medicaments of the invention described herein, effective *Candida* spp. infection treatment in a patient by administration of a dAb/dAb according to the invention results in accelerated clearance of fungal infection; preferably healing/resolution of infection 21 to 28 days after the commencement of treatment with a dAb.

The present inventors consider that the treatment of *Candida* spp. using the methods, dAbs and compositions according to the present invention may not result in total (100%) eradication of *Candida* spp. at the site of infection or in the affected area. Moreover, the present inventors consider that some residual *Candida* spp. in the affected area may be beneficial to the subject. In a preferred embodiment of the above aspect of the invention, treatment with one or more dAbs or compositions thereof according to the present invention reduces *Candida* spp. levels to commensal levels (i.e., those levels found in normal healthy individuals).

The present inventors consider that the dabs and compositions according to the invention are particularly useful for the prophylaxis and/or treatment of immuno-compromised patients.

Thus in a further aspect the present invention provides the use of a dAb or composition according to the present invention in the preparation of a medicament for the prophylaxis and/or treatment of one or more conditions exhibited by an immuno-compromised individual.

Those particularly at risk from Candidiasis include immunocompromised patient including those with AIDS, or HIV-infected. Other risk factors include granulocytopenia, bone marrow transplantation, type/duration of chemotherapy, graft-versus-host disease, degree of chemotherapy-related mucositis, colonization with *Candida*, use of broad-spectrum antibiotics, hemodialysis and/or azotemia, central vascular catheters, heroin addicts, severity of illness, hyperalimentation, recurrent or persistent gastrointestinal perforation, prior surgery, solid-organ transplantation, and neonates.

Treatment of *Candida* spp infection in any one or more of those patient groups listed above with one or more dAbs according to the present invention is contemplated herein.

In a preferred embodiment of the above aspect of the invention the immunocompromised patient is suffering from one or more conditions in the group consisting of: AIDs, HIV infection and yeast infection.

Methods for the administration of dAbs according to the invention are described in the detailed description of the invention. Preferably, the dAb is administered either by topical and/or systemic administration. In a preferred embodiment of the above aspect of the invention, the administration of a pharmaceutical composition comprising dAbs for the treatment of a patient suffering from Candidiasis includes a continuous infusion over a period of time, or a single dose or bolus administration. Further, it is envisaged that following a single dose or bolus administration a second bolus dose may be administered or a continuous infusion may be administered.

In a preferred embodiment of the invention, dabs are human variable domains or comprise human framework regions (FWs) and one or more heterologous CDRs which bind specifically to one or more Sap and/or MP proteins described herein. CDRs and framework regions are those regions of an immunoglobulin variable domain as defined in the Kabat database of Sequences of Proteins of Immunological Interest.

Preferred human framework regions are those encoded by germline gene segments DP47 and DPK9. Advantageously, FW1, FW2 and FW3 of a $V_H$ or $V_L$ domain have the sequence of FW1, FW2 or FW3 from DP47 or DPK9. The human frameworks may optionally contain mutations, for example up to about 5 amino acid changes or up to about 10 amino acid changes collectively in the human frameworks used in the dabs of the invention.

In a further aspect the present invention provides a method for the prophylaxis and/or treatment of systemic *Candida* spp. infection in a patient wherein the method comprises the step of administering to the patient in need of such treatment one or more of:
(i) An antibody which binds to a Sap and/or MP protein.
(ii) A fragment of an antibody which binds to a Sap and/or MP-protein.
(iii) A dAb which binds to a Sap and/or MP protein.

In a final aspect the present invention provides a method for the prophylaxis and/or treatment of systemic *Candida* spp. infection in a patient wherein the method comprises the step of administering to the patient in need of such treatment one or more of:
(i) An antibody which inhibits the functional activity of a Sap and/or MP protein.
(ii) A fragment of an antibody which inhibits the functional activity of a Sap and/or MP protein.
(iii) A dAb which inhibits the functional activity of a Sap and/or MP protein.

In a preferred embodiment of the above aspect of the invention, preferably the antibody or fragment thereof is monospecific. Advantageously the Sap is Sap2 and the MP protein is MP65.

In a further aspect of the present invention, dAbs can be used in a multimeric format wherein the dAbs are conjugated or fused together either directly or by a suitable linker (directly for example by chemical bond formation such as amide bond between the dAbs) or with a linker. Suitable linkers are known in the art and can be simple chains of amino acids such as Ala-Ala-Ala, $Gly_4Ser$ or multiples thereof such as $(Gly_4Ser)_5$ or chemically based such a N-hydroxylsuccinimide or maleimide links.

Further, the multimeric dAbs may be homogenous i.e. one dAb species or heterogeneous i.e. more than one dAb species, so called heteromultimer.

In a preferred embodiment, dAbs according to the invention can be formatted into dimers, which can be homogenous i.e. SAP dAbs only or heterogeneous i.e SAP dAbs and MP dAbs.

A further aspect of the present invention relates to the prevention or treatment of fungal infection or colonisation of medical devices. For example, the use of catheters or cannula eg vascular cannula, central venous catheters, urinary catheters, peritoneal dialysis catheters, and dialysis cannula, in the treatment of disease are at risk from fungal infections particularly from yeast such as *Candida* species. *Candida* species can produce biofilms on medical devices which are often highly resistance to antifungal agents and often necessitate the removal of the device. The domain antibodies according to the invention have been shown to remove or treat fungal infections of plastic.

In a further aspect of the invention, a dAb according to the invention binds Sap or MP, wherein the dAb has an amino acid sequence that is identical to the amino acid sequence of ADR4-2, ADR4-3, ADR4-4, ADR4-5, ADR4-6, ADR4-7, ADR4-8, ADR4-9, ADR4-10, ADR4-11, ADR4-12, ADR4-13, ADR4-14, ADR4-15, ADR4-16, ADR4-17, ADR4-18, ADR4-19, ADR4-21, ADR4-22, ADR4-23 and designated SEQ ID No 14 to SEQ ID No 35 respectively or ADR3-1, ADR3-2, ADR3-3, ADR3-4, ADR3-5, ADR3-6, ADR3-7, ADR3-8 and ADR3-9 and designated SEQ ID NOs 5 to SEQ ID No 13 respectively or differs from the amino acid sequence of ADR4-2, ADR4-3, ADR4-4, ADR4-5, ADR4-6, ADR4-7, ADR4-8, ADR4-9, ADR4-10, ADR4-11, ADR4-12, ADR4-13, ADR4-14, ADR4-15, ADR4-16, ADR4-17, ADR4-18, ADR4-19, ADR4-21, ADR4-22, ADR4-23 and designated SEQ ID No 14 to SEQ ID No 35 ADR3-1, ADR3-2, ADR3-3, ADR3-4, ADR3-5, ADR3-6, ADR3-7, ADR3-8 and ADR3-9 and designated SEQ ID NOs 5 to SEQ ID No 13 respectively at no more than 25 amino acid positions and has a CDR1 sequence that has at least 50% identity to the CDR1 sequence of ADR4-2, ADR4-3, ADR4-4, ADR4-5, ADR4-6, ADR4-7, ADR4-8, ADR4-9, ADR4-10, ADR4-11, ADR4-12, ADR4-13, ADR4-14, ADR4-15, ADR4-16, ADR4-17, ADR4-18, ADR4-19, ADR4-21, ADR4-22, ADR4-23 and designated SEQ ID No 14 to SEQ ID No 35 respectively ADR3-1, ADR3-2, ADR3-3, ADR3-4, ADR3-5, ADR3-6, ADR3-7, ADR3-8 and ADR3-9 and designated SEQ ID NOs 5 to SEQ ID No 13 respectively.

In a further aspect of the invention, a dAb according to the invention binds Sap or MP, wherein the dAb has an amino acid sequence that is identical to the amino acid sequence of ADR4-2, ADR4-3, ADR4-4, ADR4-5, ADR4-6, ADR4-7, ADR4-8, ADR4-9, ADR4-10, ADR4-11, ADR4-12, ADR4-13, ADR4-14, ADR4-15, ADR4-16, ADR4-17, ADR4-18, ADR4-19, ADR4-21, ADR4-22, ADR4-23 and designated SEQ ID No 14 to SEQ ID No 35 respectively or ADR3-1, ADR3-2, ADR3-3, ADR3-4, ADR3-5, ADR3-6, ADR3-7, ADR3-8 and ADR3-9 and designated SEQ ID NOs 5 to SEQ ID No 13 respectively or differs from the amino acid sequence of ADR4-2, ADR4-3, ADR4-4, ADR4-5, ADR4-6, ADR4-7, ADR4-8, ADR4-9, ADR4-10, ADR4-11, ADR4-12, ADR4-13, ADR4-14, ADR4-15, ADR4-16, ADR4-17, ADR4-18, ADR4-19, ADR4-21, ADR4-22, ADR4-23 and designated SEQ ID No 14 to SEQ ID No 35 ADR3-1, ADR3-2, ADR3-3, ADR3-4, ADR3-5, ADR3-6, ADR3-7, ADR3-8 and ADR3-9 and designated SEQ ID NOs 5 to SEQ ID No 13 respectively at no more than 25 amino acid positions and has a CDR2 sequence that has at least 50% identity to the CDR2 sequence of ADR4-2, ADR4-3, ADR4-4, ADR4-5, ADR4-6, ADR4-7, ADR4-8, ADR4-9, ADR4-10, ADR4-11, ADR4-12, ADR4-13, ADR4-14, ADR4-15, ADR4-16, ADR4-17, ADR4-18, ADR4-19, ADR4-21, ADR4-22, ADR4-23 and designated SEQ ID No 14 to SEQ ID No 35 respectively ADR3-1, ADR3-2, ADR3-3, ADR3-4, ADR3-5, ADR3-6, ADR3-7, ADR3-8 and ADR3-9 and designated SEQ ID NOs 5 to SEQ ID No 13 respectively.

In a further aspect of the invention, a dAb according to the invention binds Sap or MP, wherein the dAb has an amino acid sequence that is identical to the amino acid sequence of ADR4-2, ADR4-3, ADR4-4, ADR4-5, ADR4-6, ADR4-7, ADR4-8, ADR4-9, ADR4-10, ADR4-11, ADR4-12, ADR4-13, ADR4-14, ADR4-15, ADR4-16, ADR4-17, ADR4-18, ADR4-19, ADR4-21, ADR4-22, ADR4-23 and designated SEQ ID No 14 to SEQ ID No 35 respectively or ADR3-1, ADR3-2, ADR3-3, ADR3-4, ADR3-5, ADR3-6, ADR3-7, ADR3-8 and ADR3-9 and designated SEQ ID NOs 5 to SEQ ID No 13 respectively or differs from the amino acid sequence of ADR4-2, ADR4-3, ADR4-4, ADR4-5, ADR4-6, ADR4-7, ADR4-8, ADR4-9, ADR4-10, ADR4-11, ADR4-12, ADR4-13, ADR4-14, ADR4-15, ADR4-16, ADR4-17, ADR4-18, ADR4-19, ADR4-21, ADR4-22, ADR4-23 and designated SEQ ID No 14 to SEQ ID No 35 ADR3-1, ADR3-2, ADR3-3, ADR3-4, ADR3-5, ADR3-6, ADR3-7, ADR3-8 and ADR3-9 and designated SEQ ID NOs 5 to SEQ ID No 13 respectively at no more than 25 amino acid positions and has a CDR3 sequence that has at least 50% identity to the CDR3 sequence of ADR4-2, ADR4-3, ADR4-4, ADR4-5, ADR4-6, ADR4-7, ADR4-8, ADR4-9, ADR4-10, ADR4-11, ADR4-12, ADR4-13, ADR4-14, ADR4-15, ADR4-16, ADR4-17, ADR4-18, ADR4-19, ADR4-21, ADR4-22, ADR4-23 and designated SEQ ID No 14 to SEQ ID No 35 respectively ADR3-1, ADR3-2, ADR3-3, ADR3-4, ADR3-5, ADR3-6, ADR3-7, ADR3-8 and ADR3-9 and designated SEQ ID NOs 5 to SEQ ID No 13 respectively.

In a further aspect of the invention, a dAb according to the invention binds Sap or MP, wherein the dAb has an amino acid sequence that is identical to the amino acid sequence of ADR4-2, ADR4-3, ADR4-4, ADR4-5, ADR4-6, ADR4-7, ADR4-8, ADR4-9, ADR4-10, ADR4-11, ADR4-12, ADR4-13, ADR4-14, ADR4-15, ADR4-16, ADR4-17, ADR4-18, ADR4-19, ADR4-21, ADR4-22, ADR4-23 and designated SEQ ID No 14 to SEQ ID No 35 respectively or ADR3-1, ADR3-2, ADR3-3, ADR3-4, ADR3-5, ADR3-6, ADR3-7, ADR3-8 and ADR3-9 and designated SEQ ID NOs 5 to SEQ ID No 13 respectively or differs from the amino acid sequence of ADR4-2, ADR4-3, ADR4-4, ADR4-5, ADR4-6, ADR4-7, ADR4-8, ADR4-9, ADR4-10, ADR4-11, ADR4-12, ADR4-13, ADR4-14, ADR4-15, ADR4-16, ADR4-17, ADR4-18, ADR4-19, ADR4-21, ADR4-22, ADR4-23 and designated SEQ ID No 14 to SEQ ID No 35 respectively or ADR3-1, ADR3-2, ADR3-3, ADR3-4, ADR3-5, ADR3-6, ADR3-7, ADR3-8 and ADR3-9 and designated SEQ ID NOs 5 to SEQ ID No 13 respectively at no more than 25 amino acid positions and has a CDR1 sequence that is has at least 50% identity to the CDR1 sequence of ADR4-2, ADR4-3, ADR4-4, ADR4-5, ADR4-6, ADR4-7, ADR4-8, ADR4-9, ADR4-10, ADR4-11, ADR4-12, ADR4-13, ADR4-14, ADR4-15, ADR4-16, ADR4-17, ADR4-18, ADR4-19, ADR4-21, ADR4-22, ADR4-23 and designated SEQ ID No 14 to SEQ ID No 35 respectively or ADR3-1, ADR3-2, ADR3-3, ADR3-4, ADR3-5, ADR3-6, ADR3-7, ADR3-8 and ADR3-9 and designated SEQ ID NOs 5 to SEQ ID No 13 respectively and has a CDR2 sequence has at least 50% identity to the CDR2 sequence of ADR4-2, ADR4-3, ADR4-4, ADR4-5, ADR4-6, ADR4-7, ADR4-8, ADR4-9, ADR4-10, ADR4-11, ADR4-12, ADR4-13, ADR4-14, ADR4-15, ADR4-16, ADR4-17, ADR4-18, ADR4-19, ADR4-21, ADR4-22, ADR4-23 and designated SEQ ID No 14 to SEQ ID No 35 respectively or ADR3-1, ADR3-2, ADR3-3, ADR3-4, ADR3-5, ADR3-6, ADR3-7, ADR3-8 and ADR3-9 and designated SEQ ID NOs 5 to SEQ ID No 13 respectively.

In a further aspect of the invention, a dAb according to the invention binds Sap or MP, wherein the dAb has an amino acid sequence that is identical to the amino acid sequence of ADR4-2, ADR4-3, ADR4-4, ADR4-5, ADR4-6, ADR4-7, ADR4-8, ADR4-9, ADR4-10, ADR4-11, ADR4-12, ADR4-13, ADR4-14, ADR4-15, ADR4-16, ADR4-17, ADR4-18, ADR4-19, ADR4-21, ADR4-22, ADR4-23 and designated SEQ ID No 14 to SEQ ID No 35 respectively or ADR3-1, ADR3-2, ADR3-3, ADR3-4, ADR3-5, ADR3-6, ADR3-7, ADR3-8 and ADR3-9 and designated SEQ ID NOs 5 to SEQ ID No 13 respectively, or differs from the amino acid sequence of ADR4-2, ADR4-3, ADR4-4, ADR4-5, ADR4-6, ADR4-7, ADR4-8, ADR4-9, ADR4-10, ADR4-11, ADR4-12, ADR4-13, ADR4-14, ADR4-15, ADR4-16, ADR4-17, ADR4-18, ADR4-19, ADR4-21, ADR4-22, ADR4-23 and designated SEQ ID No 14 to SEQ ID No 35 respectively or ADR3-1, ADR3-2, ADR3-3, ADR3-4, ADR3-5, ADR3-6, ADR3-7, ADR3-8 and ADR3-9 and designated SEQ ID NOs 5 to SEQ ID No 13 respectively at no more than 25 amino acid positions and has a CDR sequence that has at least 50% identity to the CDR2 sequence of ADR4-2, ADR4-3, ADR4-4, ADR4-5, ADR4-6, ADR4-7, ADR4-8, ADR4-9, ADR4-10, ADR4-11, ADR4-12, ADR4-13, ADR4-14, ADR4-15, ADR4-16, ADR4-17, ADR4-18, ADR4-19, ADR4-21, ADR4-22, ADR4-23 and designated SEQ ID No 14 to SEQ ID No 35 respectively or ADR3-1, ADR3-2, ADR3-3, ADR3-4, ADR3-5, ADR3-6, ADR3-7, ADR3-8 and ADR3-9 and designated SEQ ID NOs 5 to SEQ ID No 13 respectively and has a CDR3 sequence that has at least 50% identity to the CDR3 sequence of ADR4-2, ADR4-3, ADR4-4, ADR4-5, ADR4-6, ADR4-7, ADR4-8, ADR4-9, ADR4-10, ADR4-11, ADR4-12, ADR4-13, ADR4-14, ADR4-15, ADR4-16, ADR4-17, ADR4-18, ADR4-19, ADR4-21, ADR4-22, ADR4-23 and designated SEQ ID No 14 to SEQ ID No 35 respectively or ADR3-1, ADR3-2, ADR3-3, ADR3-4, ADR3-5, ADR3-6, ADR3-7, ADR3-8 and ADR3-9 and designated SEQ ID NOs 5 to SEQ ID No 13 respectively.

In a further aspect of the invention, a dAb according to the invention binds Sap or MP, wherein the dAb has an amino acid sequence that is identical to the amino acid sequence of ADR4-2, ADR4-3, ADR4-4, ADR4-5, ADR4-6, ADR4-7, ADR4-8, ADR4-9, ADR4-10, ADR4-11, ADR4-12, ADR4-13, ADR4-14, ADR4-15, ADR4-16, ADR4-17, ADR4-18, ADR4-19, ADR4-21, ADR4-22, ADR4-23 and designated SEQ ID No 14 to SEQ ID No 35 respectively or ADR3-1, ADR3-2, ADR3-3, ADR3-4, ADR3-5, ADR3-6, ADR3-7, ADR3-8 and ADR3-9 and designated SEQ ID NOs 5 to SEQ ID No 13 respectively, or differs from the amino acid sequence of ADR4-2, ADR4-3, ADR4-4, ADR4-5, ADR4-6, ADR4-7, ADR4-8, ADR4-9, ADR4-10, ADR4-11, ADR4-12, ADR4-13, ADR4-14, ADR4-15, ADR4-16, ADR4-17, ADR4-18, ADR4-19, ADR4-21, ADR4-22, ADR4-23 and designated SEQ ID No 14 to SEQ ID No 35 respectively or ADR3-1, ADR3-2, ADR3-3, ADR3-4, ADR3-5, ADR3-6, ADR3-7, ADR3-8 and ADR3-9 and designated SEQ ID NOs 5 to SEQ ID No 13 respectively at no more than 25 amino acid positions and has a CDR1 sequence that has at least 50% identity to the CDR1 sequence of ADR4-2, ADR4-3, ADR4-

4, ADR4-5, ADR4-6, ADR4-7, ADR4-8, ADR4-9, ADR4-10, ADR4-11, ADR4-12, ADR4-13, ADR4-14, ADR4-15, ADR4-16, ADR4-17, ADR4-18, ADR4-19, ADR4-21, ADR4-22, ADR4-23 and designated SEQ ID No 14 to SEQ ID No 35 respectively or ADR3-1, ADR3-2, ADR3-3, ADR3-4, ADR3-5, ADR3-6, ADR3-7, ADR3-8 and ADR3-9 and designated SEQ ID NOs 5 to SEQ ID No 13 respectively and has a CDR3 sequence that has at least 50% identity to the CDR3 sequence of ADR4-2, ADR4-3, ADR4-4, ADR4-5, ADR4-6, ADR4-7, ADR4-8, ADR4-9, ADR4-10, ADR4-11, ADR4-12, ADR4-13, ADR4-14, ADR4-15, ADR4-16, ADR4-17, ADR4-18, ADR4-19, ADR4-21, ADR4-22, ADR4-23 and designated SEQ ID No 14 to SEQ ID No 35 respectively or ADR3-1, ADR3-2, ADR3-3, ADR3-4, ADR3-5, ADR3-6, ADR3-7, ADR3-8 and ADR3-9 and designated SEQ ID NOs 5 to SEQ ID No 13 respectively.

In a further aspect of the invention, a dAb according to the invention binds Sap or MP, wherein the dAb has an amino acid sequence that is identical to the amino acid sequence of ADR4-2, ADR4-3, ADR4-4, ADR4-5, ADR4-6, ADR4-7, ADR4-8, ADR4-9, ADR4-10, ADR4-11, ADR4-12, ADR4-13, ADR4-14, ADR4-15, ADR4-16, ADR4-17, ADR4-18, ADR4-19, ADR4-21, ADR4-22, ADR4-23 and designated SEQ ID No 14 to SEQ ID No 35 respectively or ADR3-1, ADR3-2, ADR3-3, ADR3-4, ADR3-5, ADR3-6, ADR3-7, ADR3-8 and ADR3-9 and designated SEQ ID NOs 5 to SEQ ID No 13 respectively, or differs from the amino acid sequence of ADR4-2, ADR4-3, ADR4-4, ADR4-5, ADR4-6, ADR4-7, ADR4-8, ADR4-9, ADR4-10, ADR4-11, ADR4-12, ADR4-13, ADR4-14, ADR4-15, ADR4-16, ADR4-17, ADR4-18, ADR4-19, ADR4-21, ADR4-22, ADR4-23 and designated SEQ ID No 14 to SEQ ID No 35 respectively or ADR3-1, ADR3-2, ADR3-3, ADR3-4, ADR3-5, ADR3-6, ADR3-7, ADR3-8 and ADR3-9 and designated SEQ ID NOs 5 to SEQ ID No 13 respectively at no more than 25 amino acid positions and has a CDR1 sequence that has at least 50% identity to the CDR1 sequence of ADR4-2, ADR4-3, ADR4-4, ADR4-5, ADR4-6, ADR4-7, ADR4-8, ADR4-9, ADR4-10, ADR4-11, ADR4-12, ADR4-13, ADR4-14, ADR4-15, ADR4-16, ADR4-17, ADR4-18, ADR4-19, ADR4-21, ADR4-22, ADR4-23 and designated SEQ ID No 14 to SEQ ID No 35 respectively or ADR3-1, ADR3-2, ADR3-3, ADR3-4, ADR3-5, ADR3-6, ADR3-7, ADR3-8 and ADR3-9 and designated SEQ ID NOs 5 to SEQ ID No 13 respectively and has a CDR2 sequence that has at least 50% identity to the CDR2 sequence of ADR4-2, ADR4-3, ADR4-4, ADR4-5, ADR4-6, ADR4-7, ADR4-8, ADR4-9, ADR4-10, ADR4-11, ADR4-12, ADR4-13, ADR4-14, ADR4-15, ADR4-16, ADR4-17, ADR4-18, ADR4-19, ADR4-21, ADR4-22, ADR4-23 and designated SEQ ID No 14 to SEQ ID No 35 respectively or ADR3-1, ADR3-2, ADR3-3, ADR3-4, ADR3-5, ADR3-6, ADR3-7, ADR3-8 and ADR3-9 and designated SEQ ID NOs 5 to SEQ ID No 13 respectively and has a CDR3 sequence that has at least 50% identity to the CDR3 sequence of ADR4-2, ADR4-3, ADR4-4, ADR4-5, ADR4-6, ADR4-7, ADR4-8, ADR4-9, ADR4-10, ADR4-11, ADR4-12, ADR4-13, ADR4-14, ADR4-15, ADR4-16, ADR4-17, ADR4-18, ADR4-19, ADR4-21, ADR4-22, ADR4-23 and designated SEQ ID No 14 to SEQ ID No 35 respectively or ADR3-1, ADR3-2, ADR3-3, ADR3-4, ADR3-5, ADR3-6, ADR3-7, ADR3-8 and ADR3-9 and designated SEQ ID NOs 5 to SEQ ID No 13 respectively.

In a further aspect of the invention, a dAb according to the invention binds Sap or MP, wherein the dAb has a CDR1 sequence that has at least 50% identity to the CDR1 sequence of ADR4-2, ADR4-3, ADR4-4, ADR4-5, ADR4-6, ADR4-7, ADR4-8, ADR4-9, ADR4-10, ADR4-11, ADR4-12, ADR4-13, ADR4-14, ADR4-15, ADR4-16, ADR4-17, ADR4-18, ADR4-19, ADR4-21, ADR4-22, ADR4-23 and designated SEQ ID No 14 to SEQ ID No 35 respectively or ADR3-1, ADR3-2, ADR3-3, ADR3-4, ADR3-5, ADR3-6, ADR3-7, ADR3-8 and ADR3-9 and designated SEQ ID NOs 5 to SEQ ID No 13 respectively.

In a further aspect of the invention, a dAb according to the invention binds Sap or MP, wherein the dAb has a CDR2 sequence that has at least 50% identity to the CDR2 sequence of ADR4-2, ADR4-3, ADR4-4, ADR4-5, ADR4-6, ADR4-7, ADR4-8, ADR4-9, ADR4-10, ADR4-11, ADR4-12, ADR4-13, ADR4-14, ADR4-15, ADR4-16, ADR4-17, ADR4-18, ADR4-19, ADR4-21, ADR4-22, ADR4-23 and designated SEQ ADR3-5, ADR3-6, ADR3-7, ADR3-8 and ADR3-9 and designated SEQ ID NOs 5 to SEQ ID No 13 respectively.

In a further aspect of the invention, a dAb according to the invention binds Sap or MP, wherein the dAb has a CDR3 sequence that has at least 50% identity to the CDR3 sequence of ADR4-2, ADR4-3, ADR4-4, ADR4-5, ADR4-6, ADR4-7, ADR4-8, ADR4-9, ADR4-10, ADR4-11, ADR4-12, ADR4-13, ADR4-14, ADR4-15, ADR4-16, ADR4-17, ADR4-18, ADR4-19, ADR4-21, ADR4-22, ADR4-23 and designated SEQ ID No 14 to SEQ ID No 35 respectively or ADR3-1, ADR3-2, ADR3-3, ADR3-4, ADR3-5, ADR3-6, ADR3-7, ADR3-8 and ADR3-9 and designated SEQ ID NOs 5 to SEQ ID No 13 respectively.

In a further aspect of the invention, a dAb according to the invention binds Sap or MP, wherein the dAb has a CDR1 sequence that has at least 50% identity to the CDR1 sequence of DOM16-39 (SEQ ID NO:345), DOM16-39-87 (SEQ ID NO:420), DOM16-39-100 (SEQ ID NO:423), DOM16-39-107 (SEQ ID NO:430), DOM16-39-109 (SEQ ID NO:432), DOM16-39-115 (SEQ ID NO:438), and DOM16-39-200 (SEQ ID NO:441) and a CDR2 sequence that has at least 50% identity to the CDR2 sequence of DOM16-39 (SEQ ID NO:345), DOM16-39-87 (SEQ ID NO:420), DOM16-39-100 (SEQ ID NO:423), DOM16-39-107 (SEQ ID NO:430), DOM16-39-109 (SEQ ID NO:432), DOM16-39-115 (SEQ ID NO:438), and DOM16-39-200 (SEQ ID NO:441).

In a further aspect of the invention, a dAb according to the invention binds Sap or MP, wherein the dAb has a CDR2 sequence that has at least 50% identity to the CDR2 sequence of DOM16-39 (SEQ ID NO:345), DOM16-39-87 (SEQ ID NO:420), DOM16-39-100 (SEQ ID NO:423), DOM16-39-107 (SEQ ID NO:430), DOM16-39-109 (SEQ ID NO:432), DOM16-39-115 (SEQ ID NO:438), and DOM16-39-200 (SEQ ID NO:441) and a CDR3 sequence that has at least 50% identity to the CDR3 sequence of DOM16-39 (SEQ ID NO:345), DOM16-39-87 (SEQ ID NO:420), DOM16-39-100 (SEQ ID NO:423), DOM16-39-107 (SEQ ID NO:430), DOM16-39-109 (SEQ ID NO:432), DOM16-39-115 (SEQ ID NO:438), and DOM16-39-200 (SEQ ID NO:441).

In a further aspect of the invention, a dAb according to the invention binds Sap or MP, wherein the dAb has a CDR1 sequence that has at least 50% identity to the CDR1 sequence of DOM16-39 (SEQ ID NO:345), DOM16-39-87 (SEQ ID NO:420), DOM16-39-100 (SEQ ID NO:423), DOM16-39-107 (SEQ ID NO:430), DOM16-39-109 (SEQ ID NO:432), DOM16-39-115 (SEQ ID NO:438), and DOM16-39-200 (SEQ ID NO:441) and a CDR3 sequence that has at least 50% identity to the CDR3 sequence of DOM16-39 (SEQ ID NO:345), DOM16-39-87 (SEQ ID NO:420), DOM16-39-100 (SEQ ID NO:423), DOM16-39-107 (SEQ ID NO:430), DOM16-39-109 (SEQ ID NO:432), DOM16-39-115 (SEQ ID NO:438), and DOM16-39-200 (SEQ ID NO:441).

In a further aspect of the invention, a dAb according to the invention binds Sap or MP, wherein the dAb has a CDR1 sequence that has at least 50% identity to the CDR1 sequence of DOM16-39 (SEQ ID NO:345), DOM16-39-87 (SEQ ID NO:420), DOM16-39-100 (SEQ ID NO:423), DOM16-39-107 (SEQ ID NO:430), DOM16-39-109 (SEQ ID NO:432), DOM16-39-115 (SEQ ID NO:438), and DOM16-39-200 (SEQ ID NO:441) and a CDR2 sequence that has at least 50% identity to the CDR2 sequence of DOM16-39 (SEQ ID NO:345), DOM16-39-87 (SEQ ID NO:420), DOM16-39-100 (SEQ ID NO:423), DOM16-39-107 (SEQ ID NO:430), DOM16-39-109 (SEQ ID NO:432), DOM16-39-115 (SEQ ID NO:438), and DOM16-39-200 (SEQ ID NO:441) and a CDR3 sequence that has at least 50% identity to the CDR3 sequence of DOM16-39 (SEQ ID NO:345), DOM16-39-87 (SEQ ID NO:420), DOM16-39-100 (SEQ ID NO:423), DOM16-39-107 (SEQ ID NO:430), DOM16-39-109 (SEQ ID NO:432), DOM16-39-115 (SEQ ID NO:438), and DOM16-39-200 (SEQ ID NO:441).

In a further aspect of the invention the serum half life of the dAb according to the invention can be increased with a half-life extension moiety. In a preferred embodiment the half-life extension moiety is PEG.

DEFINITIONS

Figure 1:
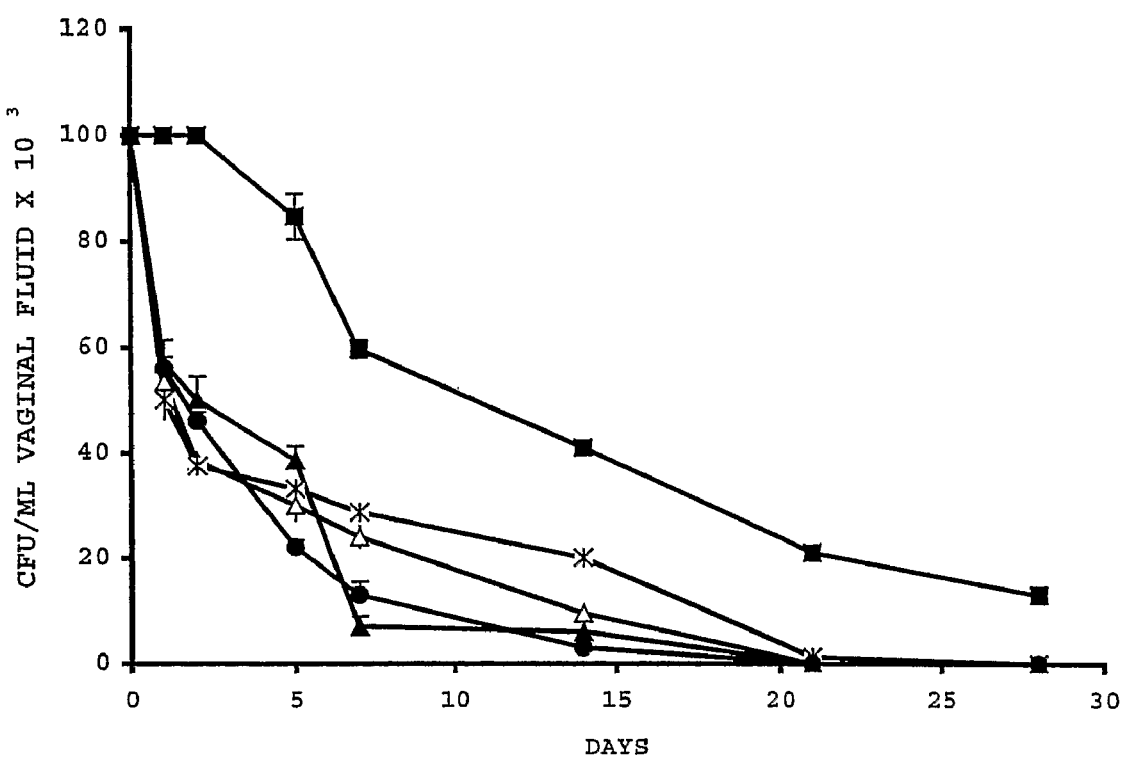
FIG. 1: Vaginal infection with *C. albicans* in rats intravaginally treated with dAbs (open triangles: ADR4-6+SA40; X: ADR3-2+SA40; closed square: SA40 (control); closed circles SA40+fluconazole; closed triangles: SA40+pepstatin).

Immunoglobulin: This refers to a family of polypeptides which retain the immunoglobulin fold characteristic of antibody molecules, which contains two β sheets and, usually, a conserved disulphide bond. Members of the immunoglobulin superfamily are involved in many aspects of cellular and non-cellular interactions in vivo, including widespread roles in the immune system (for example, antibodies, T-cell receptor molecules and the like), involvement in cell adhesion (for example the ICAM molecules) and intracellular signalling (for example, receptor molecules, such as the PDGF receptor). The present invention is applicable to all immunoglobulin superfamily molecules which possess binding domains. Preferably, the present invention relates to antibodies.

Domain: A domain is a folded protein structure which retains its tertiary structure independently of the rest of the protein. Generally, domains are responsible for discrete functional properties of proteins, and in many cases may be added, removed or transferred to other proteins without loss of function of the remainder of the protein and/or of the domain.

The term 'single domain antibody' (dAb) as used herein refers to a folded polypeptide domain comprising sequences characteristic of antibody variable domains. It therefore includes complete antibody variable domains and modified variable domains, for example in which one or more loops have been replaced by further sequences, or antibody variable domains which have been truncated or comprise N- or C-terminal extensions, as well as folded fragments of variable domains which retain at least in part the binding activity and specificity of the full-length domain. Moreover, the term dAb includes within its scope those single antibody variable domains in which one or more hypervariable loops and/or CDRs have been replaced with those from a second variable domain, which may be from the same or different origin.

Library: The term library refers to a mixture of heterogeneous polypeptides or nucleic acids. The library is composed of members, each of which have a single polypeptide or nucleic acid sequence. To this extent, library is synonymous with repertoire. Sequence differences between library members are responsible for the diversity present in the library. The library may take the form of a simple mixture of polypeptides or nucleic acids, or may be in the form of organisms or cells, for example bacteria, viruses, animal or plant cells and the like, transformed with a library of nucleic acids. Preferably, each individual organism or cell contains only one or a limited number of library members. Advantageously, the nucleic acids are incorporated into expression vectors, in order to allow expression of the polypeptides encoded by the nucleic acids. In a preferred aspect, therefore, a library may take the form of a population of host organisms, each organism containing one or more copies of an expression vector containing a single member of the library in nucleic acid form which can be expressed to produce its corresponding polypeptide member. Thus, the population of host organisms has the potential to encode a large repertoire of genetically diverse polypeptide variants.

Antibody An antibody (for example IgG, IgM, IgA, IgD or IgE) or fragment (such as a Fab, F(ab)$_2$, Fv, disulphide linked Fv, scFv, closed conformation multispecific antibody, disulphide-linked scFv, diabody,) dAb whether derived from any species naturally producing an antibody, or created by recombinant DNA technology; whether isolated from serum, B-cells, hybridomas, transfectomas, yeast or bacteria).

Antigen A molecule that is bound by a ligand according to the present invention. Typically, antigens are bound by antibody ligands and are capable of raising an antibody response in vivo. It may be a polypeptide, protein, nucleic acid or other molecule. Generally, the dAbs according to the invention are selected for target specificity against a particular antigen. In the case of conventional antibodies and fragments thereof, the antibody binding site defined by the variable loops (L1, L2, L3 and H1, H2, H3) is capable of binding to the antigen.

Epitope A unit of structure conventionally bound by an immunoglobulin $V_H/V_L$ pair. Epitopes define the minimum binding site for an antibody, and thus represent the target of specificity of an antibody. In the case of a single domain antibody, an epitope represents the unit of structure bound by a variable domain in isolation.

Universal framework A single antibody framework sequence corresponding to the regions of an antibody conserved in sequence as defined by Kabat ("Sequences of Proteins of Immunological Interest", US Department of Health and Human Services, 1991, NIH Publication No. 91-3242) or corresponding to the human germline immunoglobulin repertoire or structure as defined by Chothia and Lesk, (1987) J. Mol. Biol. 196:910-917. The invention provides for the use of a single framework, or a set of such frameworks, which has been found to permit the derivation of virtually any binding specificity though variation in the hypervariable regions alone.

Substantially identical: A first amino acid or nucleotide sequence that contains a sufficient number of identical amino acid residues or nucleotides to a second amino acid or nucleotide sequence such that the first and second amino acid or nucleotide sequences have similar activities. In the case of antibodies, the second antibody has the same binding specificity and has at least 50% of the affinity of the same.

Systemic candidiasis: In this application the term systemic candidiasis is used but is synonymous with the terms "invasive Candidiasis", "disseminated Candidiasis" and "hematogenous Candidiasis".

DETAILED DESCRIPTION OF THE INVENTION

Unless defined otherwise, all technical and scientific terms used herein have the same meaning as commonly understood by one of ordinary skill in the art (e.g., in cell culture, molecular genetics, nucleic acid chemistry, hybridisation techniques and biochemistry). Standard techniques are used for molecular, genetic and biochemical methods (see generally, Sambrook et al., Molecular Cloning: A Laboratory Manual, 2d ed. (1989) Cold Spring Harbor Laboratory Press, Cold Spring Harbor, N.Y. and Ausubel et al., Short Protocols in Molecular Biology (1999) 4$^{th}$ Ed, John Wiley & Sons, Inc. which are incorporated herein by reference) and chemical methods.

(A) *Candida* spp. Infection.

Yeast infections usually result from an overgrowth of a species of fungus called *Candida albicans*. They can occur on the skin, under nails or mucous membranes of the mouth, vagina, bronchi, and lungs.

Vaginal yeast infections are a type of vaginitis. The hallmark symptom of a yeast infection is itching of the external and internal genitalia, which is often associated with a white discharge that can be thick and/or curdy (like cottage cheese). Severe infections lead to inflammation of the tissue and subsequent redness, swelling, and even pinpoint bleeding.

Candida infections of any species may be treated using one or more dAbs according to the present invention. Preferred *Candida* spp, for treatment according to the invention include any of those in the group consisting of the following: *Candida albicans, Candida tropicalis, Candida glabrata, Candida parapsilosis, Candida krusei* and *Candida lusitaniae*. In a most preferred embodiment of the above aspect of the invention, the *Candida* species is *Candida albicans*.

Current Medical Treatments.

Over the counter drugs available to treat yeast infection caused by candida include clotrimazole (Gyne-Lotrimin®, Mycelex®), miconazole (Monistat®), and butoconazole (Femstat®).

Prescription drugs include oral fluconazole (Diflucan®), nystatin (Mycostatin®) vaginal tablets, terconazole (Terazol®) vaginal cream, and butoconazole (Gynazole®) vaginal cream. The antifungal creams may also be applied topically to the vulva (external genitalia) to help relieve itching.

Vaginitis

Vaginitis is inflammation of the vagina.

The three general causes of vaginitis are hormonal imbalance, irritation, and infection. Infectious vaginitis is most common in reproductive-age women and is generally caused by one of three types of infections: bacterial vaginosis (BV), candidiasis-caused by *Candida* spp. infection (for example *Candida albicans* infection), or trichomoniasis.

(B) *Candida* spp. Virulence Factor Binding Dabs According to the Invention.

In a first aspect the present invention provides a single domain antibody (dAb) which is capable of binding to and/or inhibiting the functional activity of a secretory aspartic protease (Sap) from *Candida* spp.

In a further aspect the present invention provides a single domain antibody (dAb) which is capable of binding to and/or inhibiting the functional activity of mannoprotein adhesin (MP) from *Candida* spp.

(Bi) *Candida* spp. Virulence Factors.

(i) SAPs.

The secreted aspartyl proteinases (Sap), encoded by a family of 10 SAP genes, are key virulence determinants of the pathogenic members of the Candida family. Those of the *C. albicans* are the most studied. All 10 SAP genes of *C. albicans* encode preproenzymes approximately 60 amino acids longer than the mature enzyme, which are processed when transported via the secretory pathway. The mature enzymes are between 35 and 50 kDa in size and contain sequence motifs typical for all aspartyl proteinases, including the two conserved aspartate residues of the active site and conserved cysteine residues implicated in the maintenance of the three-dimensional structure. Most Sap proteins contain putative N-glycosylation sites. It is currently believed that the main roles of the *C. albicans* proteinases are to provide nutrition for the cells, to aid penetration and invasion, and to evade immune responses. (Naglik, J. R. 2003 Microbiology and Molecular Biology Reviews, 67. 3. 400-428).

(ii) Mannoprotein Adhesin.

Successful colonization and infection of host tissues by the pathogenic Candida species depend upon the ability of these organisms to adhere to mucosal surfaces. The different species vary in their ability to adhere, and there is a clear correlation between adhesion and virulence. The mechanism of adhesion of the most pathogenic species, Candida albicans, to epithelial cells has been studied in detail and is thought to involve lectin-like interactions between specific binding molecules (adhesins) on the yeast surface and complementary receptor molecules on the epithelial cell surface. Current information suggests that the protein portion of mannoprotein located in fibrils on the yeast surface serves as the adhesin and interacts with glycoside receptors on epithelial cells.

(Bii) Sap Binding dAbs According to the Invention.

Secretory aspartic proteases for binding by one or more dAbs according to the present invention include Sap1, Sap2, Sap3, Sap4, Sap5 and Sap6, Sap8, Sap9 and Sap10 secretory aspartic proteases. In a preferred embodiment of the above aspect of the invention, the dAb is a Sap2 binding dAb (Sap2 binding dAb). Preferably it is a Sap2 binding dAb comprising, preferably consisting of, one or more sequences shown in the sequence listing provided herein and designated ADR4-2 designated SEQ ID No 14 to ADR4-23 designated SEQ ID No 35. According to the invention described herein, those amino acid sequences designated ADR4-X represent Sap2 amino acid sequences.

Advantageously, the dAb according to the present invention is capable of binding to one or more Saps as herein defined with a $K_{off}$ rate constant of between $5 \times 10^{-1}$ and $1 \times 10^{-7}$ s$^{-1}$.

More advantageously, the dAb according to the present invention is capable of binding to Sap2 with a dissociation constant (Kd) of at least 100 µM to 1 µM.

(Biii) MP Binding dAbs According to the Invention.

According to the present invention, those sequences designated ADR3-X in the sequence listing provided herein represent the sequences of mannoprotein adhesin (MP) binding dAbs.

According to the present invention, advantageously the dAb is a MP65 binding dAb comprising, preferably consisting of, one or more sequences shown in the sequence listing provided herein and designated ADR3-1, ADR3-1, ADR3-3, ADR3-4, ADR3-5, ADR3-6, ADR3-7, ADR3-8, ADR3-9 and represented as SEQ ID No 5 to SEQ ID No 13 respectively.

According to the above aspect of the invention, more advantageously the dAb is a MP65 binding dAb comprising, preferably consisting of, one or more sequences shown in the sequence listing provided herein and designated ADR3-1, ADR3-2 and ADR3-6 and designated SEQ ID NOs 5, 6 and 10 respectively.

Advantageously, the dAb according to the present invention is capable of binding to one or more MPs as herein defined with a $K_{off}$ rate constant of between $5 \times 10^{-1}$ and $1 \times 10^{-7}$ s$^{-1}$.

More advantageously, the dAb according to the present invention is capable of binding to MP65 with a dissociation constant (Kd) of at least 100 µM to 1 µM.

In a further aspect the present invention provides a single domain antibody (dAb) which is capable of binding to and/or inhibiting the functional activity of mannoprotein adhesin (MP) from *Candida* spp. and which exhibits 80% identity to those dAbs identified as ADR3-1, ADR3-2 and ADR3-6 and designated SEQ ID NOs 5, 6 and 10 respectively.

In a preferred embodiment of the above aspect of the invention, the dAb exhibits 82, 84, 86, 88, 90, 92, 94, 96, 98 or 99% identity to one or more of those dabs identified as ADR3-1, ADR3-2 and ADR3-6 and designated SEQ ID NOs 5, 6 and 10 respectively.

Calculation of Amino Acid Sequence Identity

Sequences similar or homologous (e.g., at least about 80% sequence identity) to the sequences disclosed herein are also part of the invention. In some embodiments, the sequence identity at the amino acid level can be about 85%, 90%, 91%, 92%, 93%, 94%, 95%, 96%, 97%, 98%, 99% or higher. At the nucleic acid level, the sequence identity can be about 90%, 91%, 92%, 93%, 94%, 95%, 96%, 97%, 98%, 99% or higher. Alternatively, substantial identity exists when the nucleic acid segments will hybridize under selective hybridization conditions (e.g., very high stringency hybridization conditions), to the complement of the strand. The nucleic acids may be present in whole cells, in a cell lysate, or in a partially purified or substantially pure form.

Calculations of "homology" or "sequence identity" or "similarity" between two sequences (the terms are used interchangeably herein) are performed as follows. The sequences are aligned for optimal comparison purposes (e.g., gaps can be introduced in one or both of a first and a second amino acid or nucleic acid sequence for optimal alignment and non-homologous sequences can be disregarded for comparison purposes). In a preferred embodiment, the length of a reference sequence aligned for comparison purposes is at least 30%, preferably at least 40%, more preferably at least 50%, even more preferably at least 60%, and even more preferably at least 70%, 80%, 90%, 100% of the length of the reference sequence. The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position (as used herein amino acid or nucleic acid "homology" is equivalent to amino acid or nucleic acid "identity"). The percent identity between the two sequences is a function of the number of identical positions shared by the sequences, taking into account the number of gaps, and the length of each gap, which need to be introduced for optimal alignment of the two sequences.

Advantageously, the BLAST algorithm (version 2.0) is employed for sequence alignment, with parameters set to default values. The BLAST algorithm is described in detail at the world wide web site ("www") of the National Center for Biotechnology Information (".ncbi") of the National Institutes of Health ("nih") of the U.S. government (".gov"), in the "/Blast/" directory, in the "blast_help.html" file. The search parameters are defined as follows, and are advantageously set to the defined default parameters.

BLAST (Basic Local Alignment Search Tool) is the heuristic search algorithm employed by the programs blastp, blastn, blastx, tblastn, and tblastx; these programs ascribe significance to their findings using the statistical methods of Karlin and Altschul, 1990, *Proc. Natl. Acad. Sci. USA* 87(6): 2264-8 (see the "blast_help.html" file, as described above) with a few enhancements. The BLAST programs were tailored for sequence similarity searching, for example to identify homologues to a query sequence. The programs are not generally useful for motif-style searching. For a discussion of basic issues in similarity searching of sequence databases, see Altschul et al. (1994).

The five BLAST programs available at the National Center for Biotechnology Information web site perform the following tasks:

"blastp" compares an amino acid query sequence against a protein sequence database;

"blastn" compares a nucleotide query sequence against a nucleotide sequence database;

"blastx" compares the six-frame conceptual translation products of a nucleotide query sequence (both strands) against a protein sequence database;

"tblastn" compares a protein query sequence against a nucleotide sequence database dynamically translated in all six reading frames (both strands).

"tblastx" compares the six-frame translations of a nucleotide query sequence against the six-frame translations of a nucleotide sequence database.

BLAST uses the following search parameters:

HISTOGRAM Display a histogram of scores for each search; default is yes. (See parameter H in the BLAST Manual).

DESCRIPTIONS Restricts the number of short descriptions of matching sequences reported to the number specified; default limit is 100 descriptions. (See parameter V in the manual page). See also EXPECT and CUTOFF.

ALIGNMENTS Restricts database sequences to the number specified for which high-scoring segment pairs (HSPs) are reported; the default limit is 50. If more database sequences than this happen to satisfy the statistical significance threshold for reporting (see EXPECT and CUTOFF below), only the matches ascribed the greatest statistical significance are reported. (See parameter B in the BLAST Manual).

EXPECT The statistical significance threshold for reporting matches against database sequences; the default value is 10, such that 10 matches are expected to be found merely by chance, according to the stochastic model of Karlin and Altschul (1990). If the statistical significance ascribed to a match is greater than the EXPECT threshold, the match will not be reported. Lower EXPECT thresholds are more stringent, leading to fewer chance matches being reported. Fractional values are acceptable. (See parameter E in the BLAST Manual).

CUTOFF Cutoff score for reporting high-scoring segment pairs. The default value is calculated from the EXPECT value (see above). HSPs are reported for a database sequence only if the statistical significance ascribed to them is at least as high as would be ascribed to a lone HSP having a score equal to the CUTOFF value. Higher CUTOFF values are more stringent, leading to fewer chance matches being reported. (See parameter S in the BLAST Manual). Typically, significance thresholds can be more intuitively managed using EXPECT.

MATRIX Specify an alternate scoring matrix for BLASTP, BLASTX, TBLASTN and TBLASTX. The default matrix is BLOSUM62 (Henikoff & Henikoff, 1992, *Proc. Natl. Acad. Sci. USA* 89(22):10915-9). The valid alternative choices include: PAM40, PAM120, PAM250 and IDENTITY. No alternate scoring matrices are available for BLASTN; specifying the MATRIX directive in BLASTN requests returns an error response.

STRAND Restrict a TBLASTN search to just the top or bottom strand of the database sequences; or restrict a BLASTN, BLASTX or TBLASTX search to just reading frames on the top or bottom strand of the query sequence.

FILTER Mask off segments of the query sequence that have low compositional complexity, as determined by the SEG program of Wootton & Federhen (1993) Computers and Chemistry 17:149-163, or segments consisting of short-periodicity internal repeats, as determined by the XNU program of Clayerie & States, 1993, Computers and Chemistry 17:191-201, or, for BLASTN, by the DUST program of Tatusov and Lipman (see the world wide web site of the NCBI). Filtering can eliminate statistically significant but biologically uninteresting reports from the blast output (e.g., hits against common acidic-, basic- or proline-rich regions), leaving the more biologically interesting regions of the query sequence available for specific matching against database sequences.

Low complexity sequence found by a filter program is substituted using the letter "N" in nucleotide sequence (e.g., "N" repeated 13 times) and the letter "X" in protein sequences (e.g., "X" repeated 9 times).

Filtering is only applied to the query sequence (or its translation products), not to database sequences. Default filtering is DUST for BLASTN, SEG for other programs.

It is not unusual for nothing at all to be masked by SEG, XNU, or both, when applied to sequences in SWISS-PROT, so filtering should not be expected to always yield an effect. Furthermore, in some cases, sequences are masked in their entirety, indicating that the statistical significance of any matches reported against the unfiltered query sequence should be suspect.

NCBI software causes NCBI gi identifiers to be shown in the output, in addition to the accession and/or locus name.

Most preferably, sequence comparisons are conducted using the simple BLAST search algorithm provided at the NCBI world wide web site described above, in the "/BLAST" directory.

(C) Preparation of dAbs According to the Invention.

DAbs according to the invention, may be prepared according to previously established techniques, used in the field of antibody engineering, for the preparation of scFv, "phage" antibodies and other engineered antibody molecules. Techniques for the preparation of antibodies, are for example described in the following reviews and the references cited therein: Winter & Milstein, (1991) Nature 349:293-299; Plueckthun (1992) Immunological Reviews 130:151-188; Wright et al., (1992) Crit. Rev. Immunol. 12:125-168; Holliger, P. & Winter, G. (1993) Curr. Op. Biotechn. 4, 446-449; Carter, et al. (1995) J. Hematother. 4, 463-470; Chester, K. A. & Hawkins, R. E. (1995) Trends Biotechn. 13, 294-300; Hoogenboom, H. R. (1997) Nature Biotechnol. 15, 125-126; Fearon, D. (1997) Nature Biotechnol. 15, 618-619; Pluckthun, A. & Pack, P. (1997) Immunotechnology 3, 83-105; Carter, P. & Merchant, A. M. (1997) Curr. Opin. Biotechnol. 8, 449-454; Holliger, P. & Winter, G. (1997) Cancer Immunol. Immunother. 45,128-130.

The techniques employed for selection of the variable domains employ libraries and selection procedures which are known in the art. Natural libraries (Marks et al. (1991) *J. Mol. Biol.,* 222: 581; Vaughan et al. (1996) *Nature Biotech.,* 14: 309) which use rearranged V genes harvested from human B cells are well known to those skilled in the art. Synthetic libraries (Hoogenboom & Winter (1992) *J. Mol. Biol.,* 227: 381; Barbas et al. (1992) *Proc. Natl. Acad. Sci. USA,* 89: 4457; Nissim et al. (1994) *EMBO J.,* 13: 692; Griffiths et al. (1994) *EMBO J.,* 13: 3245; De Kruif et al. (1995) *J. Mol. Biol.,* 248: 97) are prepared by cloning immunoglobulin V genes, usually using PCR. Errors in the PCR process can lead to a high degree of randomisation. $V_H$ and/or $V_L$ libraries may be selected against target antigens or epitopes separately.

Library Vector Systems

A variety of selection systems are known in the art which are suitable for use in the present invention. Examples of such systems are described below.

Bacteriophage lambda expression systems may be screened directly as bacteriophage plaques or as colonies of lysogens, both as previously described (Huse et al. (1989) *Science,* 246: 1275; Caton and Koprowski (1990) *Proc. Natl. Acad. Sci. U.S.A.,* 87; Mullinax et al. (1990) *Proc. Natl. Acad. Sci. U.S.A.,* 87: 8095; Persson et al. (1991) *Proc. Natl. Acad. Sci, U.S.A.,* 88: 2432) and are of use in the invention. Whilst such expression systems can be used to screen up to $10^6$ different members of a library, they are not really suited to screening of larger numbers (greater than $10^6$ members).

Of particular use in the construction of libraries are selection display systems, which enable a nucleic acid to be linked to the polypeptide it expresses. As used herein, a selection display system is a system that permits the selection, by suitable display means, of the individual members of the library by binding the generic and/or target ligands.

Selection protocols for isolating desired members of large libraries are known in the art, as typified by phage display techniques. Such systems, in which diverse peptide sequences are displayed on the surface of filamentous bacteriophage (Scott and Smith (1990) *Science,* 249: 386), have proven useful for creating libraries of antibody fragments (and the nucleotide sequences that encoding them) for the in vitro selection and amplification of specific antibody fragments that bind a target antigen (McCafferty et al., WO 92/01047). The nucleotide sequences encoding the $V_H$ and $V_L$ regions are linked to gene fragments which encode leader signals that direct them to the periplasmic space of *E. coli* and as a result the resultant antibody fragments are displayed on the surface of the bacteriophage, typically as fusions to bacteriophage coat proteins (e.g., pIII or pVIII). Alternatively, antibody fragments are displayed externally on lambda phage capsids (phagebodies). An advantage of phage-based display systems is that, because they are biological systems, selected library members can be amplified simply by growing the phage containing the selected library member in bacterial cells. Furthermore, since the nucleotide sequence that encodes the polypeptide library member is contained on a phage or phagemid vector, sequencing, expression and subsequent genetic manipulation is relatively straightforward.

Methods for the construction of bacteriophage antibody display libraries and lambda phage expression libraries are well known in the art (McCafferty et al. (1990) *Nature*, 348: 552; Kang et al. (1991) *Proc. Natl. Acad. Sci. U.S.A.*, 88: 4363; Clackson et al. (1991) *Nature*, 352: 624; Lowman et al. (1991) *Biochemistry*, 30: 10832; Burton et al. (1991) *Proc. Natl. Acad. Sci. U.S.A.*, 88: 10134; Hoogenboom et al. (1991) *Nucleic Acids Res.*, 19: 4133; Chang et al. (1991) *J. Immunol.*, 147: 3610; Breitling et al. (1991) *Gene*, 104: 147; Marks et al. (1991) supra; Barbas et al. (1992) supra; Hawkins and Winter (1992) *J. Immunol.*, 22: 867; Marks et al., 1992, *J. Biol. Chem.*, 267: 16007; Lerner et al. (1992) *Science*, 258: 1313, incorporated herein by reference).

One particularly advantageous approach has been the use of phage-libraries (Huston et al., 1988, Proc. Natl. Acad. Sci. U.S.A., 85: 5879-5883; Chaudhary et al. (1990) *Proc. Natl. Acad. Sci. U.S.A.*, 87: 1066-1070; McCafferty et al. (1990) supra; Clackson et al. (1991) *Nature*, 352: 624; Marks et al. (1991) *J. Mol. Biol.*, 222: 581; Chiswell et al. (1992) *Trends Biotech.*, 10: 80; Marks et al. (1992) *J. Biol. Chem.*, 267). Various embodiments of scFv libraries displayed on bacteriophage coat proteins have been described. Refinements of phage display approaches are also known, for example as described in WO96/06213 and WO92/01047 (Medical Research Council et al.) and WO97/08320 (Morphosys), which are incorporated herein by reference.

Other systems for generating libraries of polypeptides involve the use of cell-free enzymatic machinery for the in vitro synthesis of the library members. In one method, RNA molecules are selected by alternate rounds of selection against a target ligand and PCR amplification (Tuerk and Gold (1990) *Science*, 249: 505; Ellington and Szostak (1990) *Nature*, 346: 818). A similar technique may be used to identify DNA sequences which bind a predetermined human transcription factor (Thiesen and Bach (1990) *Nucleic Acids Res.*, 18: 3203; Beaudry and Joyce (1992) *Science*, 257: 635; WO92/05258 and WO92/14843). In a similar way, in vitro translation can be used to synthesise polypeptides as a method for generating large libraries. These methods which generally comprise stabilised polysome complexes, are described further in WO88/08453, WO90/05785, WO90/07003, WO91/02076, WO91/05058, and WO92/02536. Alternative display systems which are not phage-based, such as those disclosed in WO95/22625 and WO95/11922 (Affymax) use the polysomes to display polypeptides for selection.

A still further category of techniques involves the selection of repertoires in artificial compartments, which allow the linkage of a gene with its gene product. For example, a selection system in which nucleic acids encoding desirable gene products may be selected in microcapsules formed by water-in-oil emulsions is described in WO99/02671, WO00/40712 and Tawfik & Griffiths (1998) *Nature Biotechnol* 16(7), 652-6. Genetic elements encoding a gene product having a desired activity are compartmentalised into microcapsules and then transcribed and/or translated to produce their respective gene products (RNA or protein) within the microcapsules. Genetic elements which produce gene product having desired activity are subsequently sorted. This approach selects gene products of interest by detecting the desired activity by a variety of means.

Library Construction.

Libraries intended for selection, may be constructed using techniques known in the art, for example as set forth above, or may be purchased from commercial sources. Libraries which are useful in the present invention are described, for example, in WO99/20749. Once a vector system is chosen and one or more nucleic acid sequences encoding polypeptides of interest are cloned into the library vector, one may generate diversity within the cloned molecules by undertaking mutagenesis prior to expression; alternatively, the encoded proteins may be expressed and selected, as described above, before mutagenesis and additional rounds of selection are performed. Mutagenesis of nucleic acid sequences encoding structurally optimised polypeptides is carried out by standard molecular methods. Of particular use is the polymerase chain reaction, or PCR, (Mullis and Faloona (1987) *Methods Enzymol.*, 155: 335, herein incorporated by reference). PCR, which uses multiple cycles of DNA replication catalysed by a thermostable, DNA-dependent DNA polymerase to amplify the target sequence of interest, is well known in the art. The construction of various antibody libraries has been discussed in Winter et al. (1994) Ann. Rev. Immunology 12, 433-55, and references cited therein.

PCR is performed using template DNA (at least 1 fg; more usefully, 1-1000 ng) and at least 25 pmol of oligonucleotide primers; it may be advantageous to use a larger amount of primer when the primer pool is heavily heterogeneous, as each sequence is represented by only a small fraction of the molecules of the pool, and amounts become limiting in the later amplification cycles. A typical reaction mixture includes: 2 µl of DNA, 25 pmol of oligonucleotide primer, 2.5 µl of 10×PCR buffer 1 (Perkin-Elmer, Foster City, Calif.), 0.4 µl of 1.25 µM DNTP, 0.15 µl (or 2.5 units) of Taq DNA polymerase (Perkin Elmer, Foster City, Calif.) and deionized water to a total volume of 25 µl. Mineral oil is overlaid and the PCR is performed using a programmable thermal cycler. The length and temperature of each step of a PCR cycle, as well as the number of cycles, is adjusted in accordance to the stringency requirements in effect. Annealing temperature and timing are determined both by the efficiency with which a primer is expected to anneal to a template and the degree of mismatch that is to be tolerated; obviously, when nucleic acid molecules are simultaneously amplified and mutagenised, mismatch is required, at least in the first round of synthesis. The ability to optimise the stringency of primer annealing conditions is well within the knowledge of one of moderate skill in the art. An annealing temperature of between 30° C. and 72° C. is used. Initial denaturation of the template molecules normally occurs at between 92° C. and 99° C. for 4 minutes, followed by 20-40 cycles consisting of denaturation (94-99° C. for 15 seconds to 1 minute), annealing (temperature determined as discussed above; 1-2 minutes), and extension (72° C. for 1-5 minutes, depending on the length of the amplified product). Final extension is generally for 4 minutes at 72° C., and may be followed by an indefinite (0-24 hour) step at 4° C.

i. Selection of the Main-Chain Conformation

The members of the immunoglobulin superfamily all share a similar fold for their polypeptide chain. For example, although antibodies are highly diverse in terms of their primary sequence, comparison of sequences and crystallographic structures has revealed that, contrary to expectation, five of the six antigen binding loops of antibodies (H1, H2, L1, L2, L3) adopt a limited number of main-chain conformations, or canonical structures (Chothia and Lesk (1987) *J. Mol. Biol.*, 196: 901; Chothia et al. (1989) *Nature*, 342: 877). Analysis of loop lengths and key residues has therefore enabled prediction of the main-chain conformations of H1, H2, L1, L2 and L3 found in the majority of human antibodies (Chothia et al. (1992) *J. Mol. Biol.*, 227: 799; Tomlinson et al. (1995) *EMBO J.*, 14: 4628; Williams et al. (1996) *J. Mol. Biol.*, 264: 220). Although the H3 region is much more diverse in terms of sequence, length and structure (due to the use of D segments), it also forms a limited number of main-chain conformations for short loop lengths which depend on the length and the presence of particular residues, or types of residue, at key positions in the loop and the antibody framework (Martin et al. (1996) *J. Mol. Biol.,* 263: 800; Shirai et al. (1996) *FEBS Letters,* 399: 1).

The dAbs of the invention may themselves be provided in the form of libraries. In one aspect of the present invention, libraries of dAbs and/or domains are designed in which certain loop lengths and key residues have been chosen to ensure that the main-chain conformation of the members is known. Advantageously, these are real conformations of immunoglobulin superfamily molecules found in nature, to minimise the chances that they are non-functional, as discussed above. Germline V gene segments serve as one suitable basic framework for constructing antibody or T-cell receptor libraries; other sequences are also of use. Variations may occur at a low frequency, such that a small number of functional members may possess an altered main-chain conformation, which does not affect its function.

Canonical structure theory is also of use to assess the number of different main-chain conformations encoded by ligands, to predict the main-chain conformation based on ligand sequences and to chose residues for diversification which do not affect the canonical structure. It is known that, in the human $V_\kappa$ domain, the L1 loop can adopt one of four canonical structures, the L2 loop has a single canonical structure and that 90% of human $V_\kappa$ domains adopt one of four or five canonical structures for the L3 loop (Tomlinson et al. (1995) supra); thus, in the $V_\kappa$ domain alone, different canonical structures can combine to create a range of different main-chain conformations. Given that the $V_\lambda$ domain encodes a different range of canonical structures for the L1, L2 and L3 loops and that $V_\kappa$ and $V_\lambda$ domains can pair with any $V_H$ domain which can encode several canonical structures for the H1 and H2 loops, the number of canonical structure combinations observed for these five loops is very large. This implies that the generation of diversity in the main-chain conformation may be essential for the production of a wide range of binding specificities. However, by constructing an antibody library based on a single known main-chain conformation it has been found, contrary to expectation, that diversity in the main-chain conformation is not required to generate sufficient diversity to target substantially all antigens. Even more surprisingly, the single main-chain conformation need not be a consensus structure—a single naturally occurring conformation can be used as the basis for an entire library. Thus, in a preferred aspect, the dAbs of the invention possess a single known main-chain conformation.

The single main-chain conformation that is chosen is preferably commonplace among molecules of the immunoglobulin superfamily type in question. A conformation is commonplace when a significant number of naturally occurring molecules are observed to adopt it. Accordingly, in a preferred aspect of the invention, the natural occurrence of the different main-chain conformations for each binding loop of an immunoglobulin domain are considered separately and then a naturally occurring variable domain is chosen which possesses the desired combination of main-chain conformations for the different loops. If none is available, the nearest equivalent may be chosen. It is preferable that the desired combination of main-chain conformations for the different loops is created by selecting germline gene segments which encode the desired main-chain conformations. It is more preferable, that the selected germline gene segments are frequently expressed in nature, and most preferable that they are the most frequently expressed of all natural germline gene segments.

In designing dAbs or libraries thereof the incidence of the different main-chain conformations for each of the six antigen binding loops may be considered separately. For H1, H2, L1, L2 and L3, a given conformation that is adopted by between 20% and 100% of the antigen binding loops of naturally occurring molecules is chosen. Typically, its observed incidence is above 35% (i.e. between 35% and 100%) and, ideally, above 50% or even above 65%. Since the vast majority of H3 loops do not have canonical structures, it is preferable to select a main-chain conformation which is commonplace among those loops which do display canonical structures. For each of the loops, the conformation which is observed most often in the natural repertoire is therefore selected. In human antibodies, the most popular canonical structures (CS) for each loop are as follows: H1-CS1 (79% of the expressed repertoire), H2-CS 3 (46%), L1-CS 2 of $V_\kappa$ (39%), L2-CS1 (100%), L3-CS1 of $V_\kappa$ (36%) (calculation assumes a κ/λ ratio of 70:30, Hood et al. (1967) *Cold Spring Harbor Symp. Quant. Biol.,* 48: 133). For H3 loops that have canonical structures, a CDR3 length (Kabat et al. (1991) *Sequences of proteins of immunological interest*, U.S. Department of Health and Human Services) of seven residues with a salt-bridge from residue 94 to residue 101 appears to be the most common. There are at least 16 human antibody sequences in the EMBL data library with the required H3 length and key residues to form this conformation and at least two crystallographic structures in the protein data bank which can be used as a basis for antibody modelling (2cgr and 1tet). The most frequently expressed germline gene segments that this combination of canonical structures are the $V_H$ segment 3-23 (DP-47), the $J_H$ segment JH4b, the $V_\kappa$ segment O2/O12 (DPK9) and the $J_\kappa$ segment $J_\kappa 1$. $V_H$ segments DP45 and DP38 are also suitable. These segments can therefore be used in combination as a basis to construct a library with the desired single main-chain conformation.

Alternatively, instead of choosing the single main-chain conformation based on the natural occurrence of the different main-chain conformations for each of the binding loops in isolation, the natural occurrence of combinations of main-chain conformations is used as the basis for choosing the single main-chain conformation. In the case of antibodies, for example, the natural occurrence of canonical structure combinations for any two, three, four, five or for all six of the antigen binding loops can be determined. Here, it is preferable that the chosen conformation is commonplace in naturally occurring antibodies and most preferable that it observed most frequently in the natural repertoire. Thus, in human antibodies, for example, when natural combinations of the five antigen binding loops, H1, H2, L1, L2 and L3, are considered, the most frequent combination of canonical structures is determined and then combined with the most popular conformation for the H3 loop, as a basis for choosing the single main-chain conformation.

ii. Diversification of the Canonical Sequence

Having selected several known main-chain conformations or, preferably a single known main-chain conformation, dAbs according to the invention or libraries for use in the invention can be constructed by varying the binding site of the molecule in order to generate a repertoire with structural and/or functional diversity. This means that variants are generated such that they possess sufficient diversity in their structure and/or in their function so that they are capable of providing a range of activities.

The desired diversity is typically generated by varying the selected molecule at one or more positions. The positions to be changed can be chosen at random or are preferably selected. The variation can then be achieved either by randomisation, during which the resident amino acid is replaced by any amino acid or analogue thereof, natural or synthetic, producing a very large number of variants or by replacing the resident amino acid with one or more of a defined subset of amino acids, producing a more limited number of variants.

Various methods have been reported for introducing such diversity. Error-prone PCR (Hawkins et al. (1992) *J. Mol. Biol.*, 226: 889), chemical mutagenesis (Deng et al. (1994) *J. Biol. Chem.*, 269: 9533) or bacterial mutator strains (Low et al. (1996) *J. Mol. Biol.*, 260: 359) can be used to introduce random mutations into the genes that encode the molecule. Methods for mutating selected positions are also well known in the art and include the use of mismatched oligonucleotides or degenerate oligonucleotides, with or without the use of PCR. For example, several synthetic antibody libraries have been created by targeting mutations to the antigen binding loops. The H3 region of a human tetanus toxoid-binding Fab has been randomised to create a range of new binding specificities (Barbas et al. (1992) *Proc. Natl. Acad. Sci. USA*, 89: 4457). Random or semi-random H3 and L3 regions have been appended to germline V gene segments to produce large libraries with unmutated framework regions (Hoogenboom & Winter (1992) *J. Mol. Biol.*, 227: 381; Barbas et al. (1992) *Proc. Natl. Acad. Sci. USA*, 89: 4457; Nissim et al. (1994) *EMBO J.*, 13: 692; Griffiths et al. (1994) *EMBO J.*, 13: 3245; De Kruif et al. (1995) *J. Mol. Biol.*, 248: 97). Such diversification has been extended to include some or all of the other antigen binding loops (Crameri et al. (1996) *Nature Med.*, 2: 100; Riechmann et al. (1995) Bio/Technology, 13: 475; Morphosys, WO97/08320, supra).

Since loop randomisation has the potential to create approximately more than 1015 structures for H3 alone and a similarly large number of variants for the other five loops, it is not feasible using current transformation technology or even by using cell free systems to produce a library representing all possible combinations. For example, in one of the largest libraries constructed to date, $6 \times 10^{10}$ different antibodies, which is only a fraction of the potential diversity for a library of this design, were generated (Griffiths et al. (1994) supra).

In a preferred embodiment, only those residues which are directly involved in creating or modifying the desired function of the molecule are diversified. For many molecules, the function will be to bind a target and therefore diversity should be concentrated in the target binding site, while avoiding changing residues which are crucial to the overall packing of the molecule or to maintaining the chosen main-chain conformation.

Diversification of the Canonical Sequence as it applies to Antibody Domains

In the case of antibody dAbs, the binding site for the target is most often the antigen binding site. These residues are extremely diverse in the human antibody repertoire and are known to make contacts in high-resolution antibody/antigen complexes. For example, in L2 it is known that positions 50 and 53 are diverse in naturally occurring antibodies and are observed to make contact with the antigen. In contrast, the conventional approach would have been to diversify all the residues in the corresponding Complementarity Determining Region (CDR1) as defined by Kabat et al. (1991, supra), some seven residues compared to the two diversified in the library for use according to the invention. This represents a significant improvement in terms of the functional diversity required to create a range of antigen binding specificities.

In nature, antibody diversity is the result of two processes: somatic recombination of germline V, D and J gene segments to create a naive primary repertoire (so called germline and junctional diversity) and somatic hypermutation of the resulting rearranged V genes. Analysis of human antibody sequences has shown that diversity in the primary repertoire is focused at the centre of the antigen binding site whereas somatic hypermutation spreads diversity to regions at the periphery of the antigen binding site that are highly conserved in the primary repertoire (see Tomlinson et al. (1996) *J. Mol. Biol.*, 256: 813). This complementarity has probably evolved as an efficient strategy for searching sequence space and, although apparently unique to antibodies, it can easily be applied to other polypeptide repertoires. The residues which are varied are a subset of those that form the binding site for the target. Different (including overlapping) subsets of residues in the target binding site are diversified at different stages during selection, if desired.

In the case of an antibody repertoire, an initial 'naive' repertoire is created where some, but not all, of the residues in the antigen binding site are diversified. As used herein in this context, the term "naive" refers to antibody molecules that have no pre-determined target. These molecules resemble those which are encoded by the immunoglobulin genes of an individual who has not undergone immune diversification, as is the case with fetal and newborn individuals, whose immune systems have not yet been challenged by a wide variety of antigenic stimuli. This repertoire is then selected against a range of antigens or epitopes. If required, further diversity can then be introduced outside the region diversified in the initial repertoire. This matured repertoire can be selected for modified function, specificity or affinity.

In the construction of libraries for use in the invention, diversification of chosen positions is typically achieved at the nucleic acid level, by altering the coding sequence which specifies the sequence of the polypeptide such that a number of possible amino acids (all 20 or a subset thereof) can be incorporated at that position. Using the IUPAC nomenclature, the most versatile codon is NNK, which encodes all amino acids as well as the TAG stop codon. The NNK codon is preferably used in order to introduce the required diversity. Other codons which achieve the same ends are also of use, including the NNN codon, which leads to the production of the additional stop codons TGA and TAA.

A feature of side-chain diversity in the antigen binding site of human antibodies is a pronounced bias which favours certain amino acid residues. If the amino acid composition of the ten most diverse positions in each of the $V_H$, $V_\kappa$ and $V_\lambda$ regions are summed, more than 76% of the side-chain diversity comes from only seven different residues, these being, serine (24%), tyrosine (14%), asparagine (11%), glycine (9%), alanine (7%), aspartate (6%) and threonine (6%). This bias towards hydrophilic residues and small residues which can provide main-chain flexibility probably reflects the evolution of surfaces which are predisposed to binding a wide range of antigens or epitopes and may help to explain the required promiscuity of antibodies in the primary repertoire.

Since it is preferable to mimic this distribution of amino acids, the distribution of amino acids at the positions to be varied preferably mimics that seen in the antigen binding site of antibodies. Such bias in the substitution of amino acids that permits selection of certain polypeptides (not just antibody polypeptides) against a range of target antigens is easily applied to any polypeptide repertoire. There are various methods for biasing the amino acid distribution at the position to be varied (including the use of tri-nucleotide mutagenesis, see WO97/08320), of which the preferred method, due to ease of synthesis, is the use of conventional degenerate codons. By comparing the amino acid profile encoded by all combinations of degenerate codons (with single, double, triple and quadruple degeneracy in equal ratios at each position) with the natural amino acid use it is possible to calculate the most representative codon. The codons (AGT)(AGC)T, (AGT)(AGC)C and (AGT)(AGC)(CT)—that is, DVT, DVC and DVY, respectively using IUPAC nomenclature—are those closest to the desired amino acid profile: they encode 22% serine and 11% tyrosine, asparagine, glycine, alanine, aspartate, threonine and cysteine. Preferably, therefore, libraries are constructed using either the DVT, DVC or DVY codon at each of the diversified positions.

D. Characterisation of dAbs According to the Present Invention.

The binding of dAbs according to the invention to its specific antigens (*Candida* spp. virulence factors) or epitopes can be tested by methods which will be familiar to those skilled in the art and include ELISA. In a preferred embodiment binding is tested using monoclonal phage ELISA.

Phage ELISA may be performed according to any suitable procedure: an exemplary protocol is set forth below.

Populations of phage produced at each round of selection can be screened for binding by ELISA to the selected antigen or epitope, to identify "polyclonal" phage antibodies. Phage from single infected bacterial colonies from these populations can then be screened by ELISA to identify "monoclonal" phage antibodies. It is also desirable to screen soluble antibody fragments for binding to antigen or epitope, and this can also be undertaken by ELISA using reagents, for example, against a C- or N-terminal tag (see for example Winter et al. (1994) *Ann. Rev. Immunology* 12, 433-55 and references cited therein).

The diversity of the selected phage monoclonal antibodies may also be assessed by gel electrophoresis of PCR products (Marks et al. 1991, supra; Nissim et al. 1994 supra), probing (Tomlinson et al, 1992) J. Mol. Biol. 227, 776) or by sequencing of the vector DNA.

E. Treatment of *Candida* spp. Infection Using dAbs According to the Invention dAbs selected according to the method of the present invention may be employed in in vivo therapeutic and prophylactic applications, in vitro and in vivo diagnostic applications, in vitro assay and reagent applications, and the like. For example dAbs may be used in antibody based assay techniques, such as ELISA techniques, according to methods known to those skilled in the art.

As alluded to above, dAbs according to the invention are of use in diagnostic, prophylactic and therapeutic procedures. Single domain-effector group antibodies (dAbs) selected according to the invention are of use diagnostically in Western analysis and in situ protein detection by standard immunohistochemical procedures; for use in these applications, the antibodies of a selected repertoire may be labelled in accordance with techniques known to the art. In addition, such antibody polypeptides may be used preparatively in affinity chromatography procedures, when complexed to a chromatographic support, such as a resin. All such techniques are well known to one of skill in the art.

Substantially pure dAbs according to the present invention of at least 90 to 95% homogeneity are preferred for administration to a mammal, and 98 to 99% or more homogeneity is most preferred for pharmaceutical uses, especially when the mammal is a human. Once purified, partially or to homogeneity as desired, the selected dAbs may be used diagnostically and/or therapeutically (including extracorporeally) or in developing and performing assay procedures, immunofluorescent stainings and the like (Lefkovite and Pernis, (1979 and 1981) Immunological Methods, Volumes I and II, Academic Press, NY).

The dAbs of the present invention will typically find use in preventing, suppressing or treating *Candida* spp. infection, in particular, *Candida albicans* infection in an individual.

In the instant application, the term "prevention" involves administration of the protective composition prior to the induction of the disease. "Suppression" refers to administration of the composition after an inductive event, but prior to the clinical appearance of the disease. "Treatment" involves administration of the protective composition after disease symptoms become manifest.

Animal model systems which can be used to screen the dAbs in protecting against or treating *Candida* spp. infection are available and will be familiar to those skilled in the art. Details of some model systems used are provided in the Examples. *Candida* spp. infection may occur systemically, mucosally, bronchially, in the lungs, under nails, orally or vaginally. In a preferred embodiment of the invention described herein, one or more dAbs according to the invention are used for the treatment of vaginal or systemic *Candida* spp. infection, in particular vaginal or systemic *Candida albicans* infection.

dAbs disclosed herein, can be formatted to extend its in vivo serum half life. Increased in vivo half-life is useful in in vivo applications of immunoglobulins, especially antibodies and most especially antibody fragments of small size such as dAbs. Such fragments (Fvs, disulphide bonded Fvs, Fabs, scFvs, dAbs) are rapidly cleared from the body, which can severely limit clinical applications.

A dAb can be formatted be formatted as a larger antigen-binding fragment of an antibody or as and antibody (e.g., formatted as a Fab, Fab', F(ab)$_2$, F(ab')$_2$, IgG, scFv) that has larger hydrodynamic size. dAbs can also be formatted to have a larger hydrodynamic size, for example, by attachment of a polyalkyleneglycol group (e.g. polyethyleneglycol (PEG) group, polypropylene glycol, polybutylene glycol), serum albumin, transferrin, transferrin receptor or at least the transferrin-binding portion thereof, an antibody Fc region, or by conjugation to an antibody domain. In some embodiments, the dAb is PEGylated. Preferably the PEGylated dAb binds SAP and MP with substantially the same affinity or avidity as the same dAb that is not PEGylated. For example, the dAbs can be a PEGylated dAb comprising a dAb that binds SAP and MP with an avidity that differs from the avidity of dAb in unPEGylated form by no more than a factor of about 1000, preferably no more than a factor of about 100, more preferably no more than a factor of about 10, or with avidity substantially unchanged affinity relative to the unPEGylated form. See, PCT/GB03/002804, filed Jun. 30, 2003, (WO 2004/081026) regarding PEGylated of single variable domains and dAbs, suitable methods for preparing same, increased in vivo half life of the PEGylated single variable domains and dAb monomers and multimers, suitable PEGs, preferred hydrodynamic sizes of PEGs, and preferred hydrodynamic sizes of PEGylated single variable domains and dAb monomers and multimers. The entire teaching of PCT/GB03/002804 (WO 2004/081026), including the portions referred to above, are incorporated herein by reference.

Hydrodynamic size of the dAbs (e.g., dAb monomers and multimers) of the invention may be determined using methods which are well known in the art. For example, gel filtration chromatography may be used to determine the hydrodynamic size of a dAb. Suitable gel filtration matrices for determining the hydrodynamic sizes of dAbs, such as cross-linked agarose matrices, are well known and readily available.

The size of a dAb format (e.g., the size of a PEG moiety attached to a dAb), can be varied depending on the desired application. For example, where dAb is intended to leave the circulation and enter into peripheral tissues, it is desirable to keep the hydrodynamic size of the ligand low to facilitate extravazation from the blood stream. Alternatively, where it is desired to have the dAb remain in the systemic circulation for a longer period of time the size of the dAb can be increased, for example by formatting as and Ig like protein or by addition of a 30 to 60 kDa PEG moiety (e.g., linear or branched PEG 30 to 40 kDa PEG, such as addition of two 20 kDa PEG moieties.) The size of the dAb format can be tailored to achieve a desired in vivo serum half life, for example to control exposure to a toxin and/or to reduce side effects of toxic agents.

The hydrodynamic size of a dAb and its serum half-life can also be increased by conjugating or linking the dAb to a binding domain (e.g., antibody or antibody fragment) that binds an antigen or epitope that increases half-live in vivo, as described herein. For example, the dAb can be conjugated or linked to an anti-serum albumin or anti-neonatal Fc receptor antibody or antibody fragment, e.g., an anti-SA or anti-neonatal Fc receptor dAb, Fab, Fab' or scFv, or to an anti-SA affibody or anti-neonatal Fc receptor affibody.

Examples of suitable albumin, albumin fragments or albumin variants for use in a ligand according to the invention are described in WO 2005/077042A2, which is incorporated herein by reference in its entirety. In particular, the following albumin, albumin fragments or albumin variants can be used in the present invention:

a SEQ ID NO: 1 (as disclosed in WO 2005/077042A2, this sequence being explicitly incorporated into the present disclosure by reference);

Albumin fragment or variant comprising or consisting of amino acids 1-387 of SEQ ID NO:1 in WO 2005/077042A2;

Albumin, or fragment or variant thereof, comprising an amino acid sequence selected from the group consisting of: (a) amino acids 54 to 61 of SEQ ID NO:1 in WO 2005/077042A2; (b) amino acids 76 to 89 of SEQ ID NO:1 in WO 2005/077042A2; (c) amino acids 92 to 100 of SEQ ID NO:1 in WO 2005/077042A2; (d) amino acids 170 to 176 of SEQ ID NO:1 in WO 2005/077042A2; (e) amino acids 247 to 252 of SEQ ID NO:1 in WO 2005/077042A2; (f) amino acids 266 to 277 of SEQ ID NO:1 in WO 2005/077042A2; (g) amino acids 280 to 288 of SEQ ID NO:1 in WO 2005/077042A2; (h) amino acids 362 to 368 of SEQ ID NO:1 in WO 2005/077042A2; (i) amino acids 439 to 447 of SEQ ID NO:1 in WO 2005/077042A2 (j) amino acids 462 to 475 of SEQ ID NO:1 in WO 2005/077042A2; (k) amino acids 478 to 486 of SEQ ID NO:1 in WO 2005/077042A2; and (l) amino acids 560 to 566 of SEQ ID NO:1 in WO 2005/077042A2.

Figure 3:
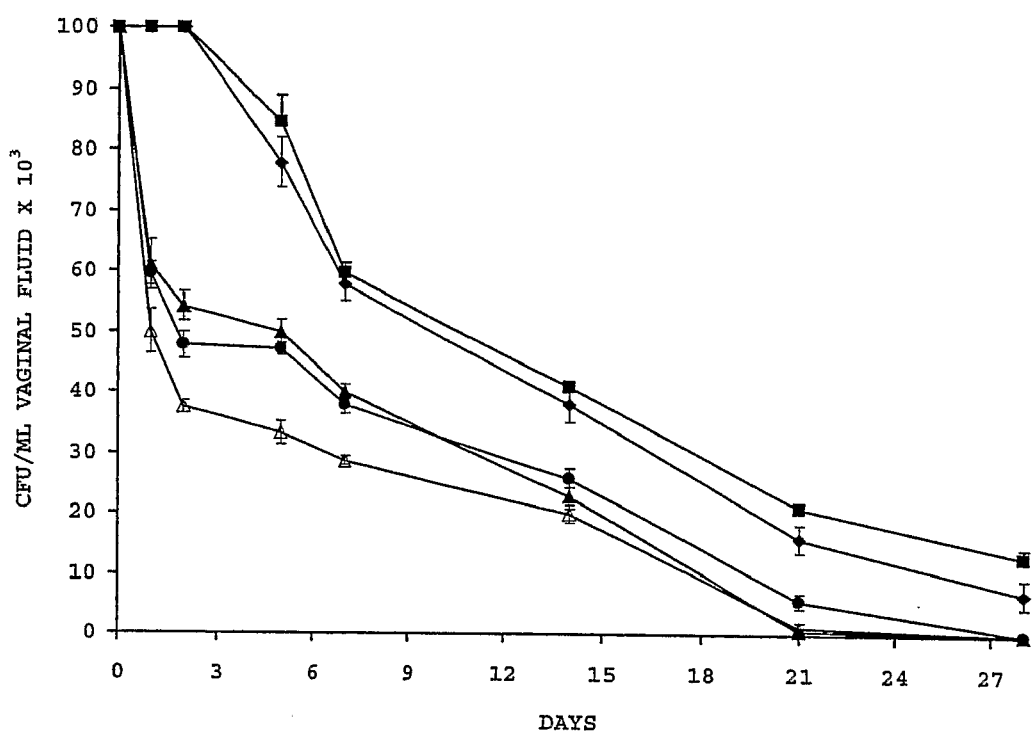
FIG. 3: Vaginal infection with *C. albicans* in rats intravaginally treated with anti-mp65 domains (closed triangles ADR3-1; circles ADR3-2; open triangles ADR3-6; diamonds Hel4; closed squares SA40 (control).

Further examples of suitable albumin, fragments and analogs for use in a dAb composition according to the invention are described in WO 03/076567A2, which is incorporated herein by reference in its entirety. In particular, the following albumin, fragments or variants can be used in the present invention:

Human serum albumin as described in WO 03/076567A2, eg, in FIG. 3 (this sequence information being explicitly incorporated into the present disclosure by reference);

Human serum albumin (HA) consisting of a single non-glycosylated polypeptide chain of 585 amino acids with a formula molecular weight of 66,500 (See, Meloun, et al., FEBS Letters 58:136 (1975); Behrens, et al., Fed. Proc. 34:591 (1975); Lawn, et al., Nucleic Acids Research 9:6102-6114 (1981); Minghetti, et al., J. Biol. Chem. 261:6747 (1986));

A polymorphic variant or analog or fragment of albumin as described in Weitkamp, et al., Ann. Hum. Genet. 37:219 (1973);

An albumin fragment or variant as described in EP 322094, eg, HA(1-373., HA(1-388), HA(1-389), HA(1-369), and HA(1-419) and fragments between 1-369 and 1-419;

An albumin fragment or variant as described in EP 399666, eg, HA(1-177) and HA(1-200) and fragments between HA(1-X), where X is any number from 178 to 199.

Where a (one or more) half-life extending moiety (eg, albumin, transferrin and fragments and analogues thereof) is used in the dAbs of the invention, it can be conjugated to the dAb using any suitable method, such as, by direct fusion to the dAb, for example by using a single nucleotide construct that encodes a fusion protein, wherein the fusion protein is encoded as a single polypeptide chain with the half-life extending moiety located N- or C-terminally to the cell surface target binding moieties. Alternatively, conjugation can be achieved by using a peptide linker between dAb, eg, a peptide linker as described in WO 03/076567A2 or WO 2004/003019 (these linker disclosures being incorporated by reference in the present disclosure to provide examples for use in the present invention).

Typically, a polypeptide that enhances serum half-life in vivo is a polypeptide which occurs naturally in vivo and which resists degradation or removal by endogenous mechanisms which remove unwanted material from the organism (e.g., human). For example, a polypeptide that enhances serum half-life in vivo can be selected from proteins from the extracellular matrix, proteins found in blood, proteins found at the blood brain barrier or in neural tissue, proteins localized to the kidney, liver, lung, heart, skin or bone, stress proteins, disease-specific proteins, or proteins involved in Fc transport.

Suitable polypeptides that enhance serum half-life in vivo include, for example, transferrin receptor specific ligand-neuropharmaceutical agent fusion proteins (see U.S. Pat. No. 5,977,307, the teachings of which are incorporated herein by reference), brain capillary endothelial cell receptor, transferrin, transferrin receptor (e.g., soluble transferrin receptor), insulin, insulin-like growth factor 1 (IGF 1) receptor, insulin-like growth factor 2 (IGF 2) receptor, insulin receptor, blood coagulation factor X, $\alpha$1-antitrypsin and HNF 1$\alpha$. Suitable polypeptides that enhance serum half-life also include alpha-1 glycoprotein (orosomucoid; AAG), alpha-1 antichymotrypsin (ACT), alpha-1 microglobulin (protein HC; AIM), antithrombin III (AT III), apolipoprotein A-1 (Apo A-1), apolipoprotein B (Apo B), ceruloplasmin (Cp), complement component C3 (C3), complement component C4 (C4), C1 esterase inhibitor (C1 INH), C-reactive protein (CRP), ferritin (FER), hemopexin (HPX), lipoprotein(a) (Lp(a)), mannose-binding protein (MBP), myoglobin (Myo), prealbumin (transthyretin; PAL), retinol-binding protein (RBP), and rheumatoid factor (RF).

Suitable proteins from the extracellular matrix include, for example, collagens, laminins, integrins and fibronectin. Collagens are the major proteins of the extracellular matrix. About 15 types of collagen molecules are currently known, found in different parts of the body, e.g. type I collagen (accounting for 90% of body collagen) found in bone, skin, tendon, ligaments, cornea, internal organs or type II collagen found in cartilage, vertebral disc, notochord, and vitreous humor of the eye.

Suitable proteins from the blood include, for example, plasma proteins (e.g., fibrin, α-2 macroglobulin, serum albumin, fibrinogen (e.g., fibrinogen A, fibrinogen B), serum amyloid protein A, haptoglobin, profilin, ubiquitin, uteroglobulin and β-2-microglobulin), enzymes and enzyme inhibitors (e.g., plasminogen, lysozyme, cystatin C, alpha-1-antitrypsin and pancreatic trypsin inhibitor), proteins of the immune system, such as immunoglobulin proteins (e.g., IgA, IgD, IgE, IgG, IgM, immunoglobulin light chains (kappa/lambda)), transport proteins (e.g., retinol binding protein, α-1 microglobulin), defensins (e.g., beta-defensin 1, neutrophil defensin 1, neutrophil defensin 2 and neutrophil defensin 3) and the like.

Suitable proteins found at the blood brain barrier or in neural tissue include, for example, melanocortin receptor, myelin, ascorbate transporter and the like.

Suitable polypeptides that enhances serum half-life in vivo also include proteins localized to the kidney (e.g., polycystin, type IV collagen, organic anion transporter K1, Heymann's antigen), proteins localized to the liver (e.g., alcohol dehydrogenase, G250), proteins localized to the lung (e.g., secretory component, which binds IgA), proteins localized to the heart (e.g., HSP 27, which is associated with dilated cardiomyopathy), proteins localized to the skin (e.g., keratin), bone specific proteins such as morphogenic proteins (BMPs), which are a subset of the transforming growth factor β superfamily of proteins that demonstrate osteogenic activity (e.g., BMP-2, BMP-4, BMP-5, BMP-6, BMP-7, BMP-8), tumor specific proteins (e.g., trophoblast antigen, herceptin receptor, oestrogen receptor, cathepsins (e.g., cathepsin B, which can be found in liver and spleen)).

Suitable disease-specific proteins include, for example, antigens expressed only on activated T-cells, including LAG-3 (lymphocyte activation gene), osteoprotegerin ligand (OPGL; see *Nature* 402, 304-309 (1999)), OX40 (a member of the TNF receptor family, expressed on activated T cells and specifically up-regulated in human T cell leukemia virus type-I (HTLV-I)-producing cells; see *Immunol.* 165 (1):263-70 (2000)). Suitable disease-specific proteins also include, for example, metalloproteases (associated with arthritis/cancers) including CG6512 *Drosophila*, human paraplegin, human FtsH, human AFG3L2, murine ftsH; and angiogenic growth factors, including acidic fibroblast growth factor (FGF-1), basic fibroblast growth factor (FGF-2), vascular endothelial growth factor/vascular permeability factor (VEGF/VPF), transforming growth factor-α (TGF α), tumor necrosis factor-alpha (TNF-α), angiogenin, interleukin-3 (IL-3), interleukin-8 (IL-8), platelet-derived endothelial growth factor (PD-ECGF), placental growth factor (P1GF), midkine platelet-derived growth factor-BB (PDGF), and fractalkine.

Suitable polypeptides that enhance serum half-life in vivo also include stress proteins such as heat shock proteins (HSPs). HSPs are normally found intracellularly. When they are found extracellularly, it is an indicator that a cell has died and spilled out its contents. This unprogrammed cell death (necrosis) occurs when as a result of trauma, disease or injury, extracellular HSPs trigger a response from the immune system. Binding to extracellular HSP can result in localizing the compositions of the invention to a disease site.

Suitable proteins involved in Fc transport include, for example, Brambell receptor (also known as FcRB). This Fc receptor has two functions, both of which are potentially useful for delivery. The functions are (1) transport of IgG from mother to child across the placenta (2) protection of IgG from degradation thereby prolonging its serum half-life. It is thought that the receptor recycles IgG from endosomes. (See, Holliger et al, *Nat Biotechnol* 15(7):632-6 (1997).)

Methods for pharmacokinetic analysis and determination of dAb half-life will be familiar to those skilled in the art. Details may be found in Kenneth, A et al. Chemical Stability of Pharmaceuticals: A Handbook for Pharmacists and in Peters et al, Pharmacokinetc analysis: A Practical Approach (1996). Reference is also made to "Pharmacokinetics", M Gibaldi & D Perron, published by Marcel Dekker, $2^{nd}$ Rev. ex edition (1982), which describes pharmacokinetic parameters such as t alpha and t beta half lives and area under the curve (AUC).

Generally, the dAbs will be utilised in purified form together with pharmacologically appropriate carriers. Typically, these carriers include aqueous or alcoholic/aqueous solutions, emulsions or suspensions, any including saline and/or buffered media. Parenteral vehicles include sodium chloride solution, Ringer's dextrose, dextrose and sodium chloride and lactated Ringer's. Suitable physiologically-acceptable adjuvants, if necessary to keep a polypeptide complex in suspension, may be chosen from thickeners such as carboxymethylcellulose, polyvinylpyrrolidone, gelatin and alginates.

Intravenous vehicles include fluid and nutrient replenishers and electrolyte replenishers, such as those based on Ringer's dextrose. Preservatives and other additives, such as antimicrobials, antioxidants, chelating agents and inert gases, may also be present (Mack (1982) *Remington's Pharmaceutical Sciences,* 16th Edition).

The dAbs of the present invention may be used as separately administered compositions or in conjunction with other agents. These can include various immunotherapeutic drugs, such as cylcosporine, methotrexate, adriamycin or cisplatinum, and immunotoxins. Pharmaceutical compositions can include "cocktails" of various cytotoxic or other agents in conjunction with the dabs of the present invention, or even combinations of dAbs according to the present invention having different specificities.

The route of administration of pharmaceutical compositions according to the invention may be any of those commonly known to those of ordinary skill in the art. For therapy, including without limitation immunotherapy, the dAbs and compositions of the invention can be administered to any patient in accordance with standard techniques. The administration can be by any appropriate mode, including parenterally, intravenously, intramuscularly, intraperitoneally, transdermally, via the pulmonary route, or also, appropriately, by direct infusion with a catheter. The dosage and frequency of administration will depend on the age, sex and condition of the patient, concurrent administration of other drugs, counterindications and other parameters to be taken into account by the clinician.

In a preferred embodiment of the invention, therapeutic compositions described herein are administered by either topically or systemically.

In a preferred embodiment of the invention, the administration of a pharmaceutical composition comprising dAbs for the treatment of a patient suffering from Candidiasis includes a continuous infusion over a period of time, or a single dose or bolus administration. Further, it is envisaged that following a single dose or bolus administration a second bolus dose may be administered or a continuous infusion may be administered.

The dAbs of this invention can be lyophilised for storage and reconstituted in a suitable carrier prior to use. This technique has been shown to be effective with conventional immunoglobulins and art-known lyophilisation and reconstitution techniques can be employed. It will be appreciated by those skilled in the art that lyophilisation and reconstitution can lead to varying degrees of antibody activity loss (e.g. with conventional immunoglobulins, IgM antibodies tend to have greater activity loss than IgG antibodies) and that use levels may have to be adjusted upward to compensate.

The compositions containing the dabs or a cocktail thereof can be administered for prophylactic and/or therapeutic treatments. In certain therapeutic applications, an adequate amount to accomplish at least partial inhibition, suppression, modulation, killing, or some other measurable parameter, of a population of selected cells is defined as a "therapeutically-effective dose". Amounts needed to achieve this dosage will depend upon the severity of the disease and the general state of the patient's own immune system, but generally range from 0.005 to 5.0 mg of selected dAb per kilogram of body weight, with doses of 0.05 to 2.0 mg/kg/dose being more commonly used. For prophylactic applications, compositions containing the dAbs or cocktails thereof may also be administered in similar or slightly lower dosages.

A composition containing a dAb or cocktail thereof according to the present invention may be utilised in prophylactic and therapeutic settings to aid in the alteration, inactivation, killing or removal of a select target cell population in a mammal. In addition, the dAbs described herein may be used extracorporeally or in vitro selectively to kill, deplete or otherwise effectively remove a target cell population from a heterogeneous collection of cells. Blood from a mammal may be combined extracorporeally with the selected antibodies, cell-surface receptors or binding proteins thereof whereby the undesired cells are killed or otherwise removed from the blood for return to the mammal in accordance with standard techniques.

The invention is further described, for the purposes of illustration only, in the following examples.

EXAMPLES

Example 1

Materials and Methods

Microrganism and Growth Conditions

Throughout this study the common laboratory yeast *Candida albicans* was used. However, it is envisaged that the invention can be used to prevention or treat other yeast such as *tropicalis, glabtrata, krusei, norvegensis* or *inconspicua*.

*Candida albicans* strain SA40 and AIDS 68 were used throughout this study. SA40 was fully susceptible to fluconazole and other triazole drugs whereas the strain AIDS 68 was isolated from an AIDS patient as fluconazole resistant (i.e. MIC>64 µg/ml as defined by NCLLS methods). Both strains were routinely grown in Yeast-peptone-dextrose (YPD; 1% yeast extract, 2% bacto-peptone, 2% glucose, all w/v) or Yeast Nitrogen Base (YNB; 2% glucose, 0.17% yeast nitrogen base without amino acids and ammonium sulphate, 0.5% ammonium sulphate, w/v) or Winge (0.3% yeast extract, 0.2% glucose) or SDB (1% bacto-peptone, 2% dextrose) media at 28° C. All media were solidified with 2% agar.

Filamentation (hyphae formation) on agar-solidified media was obtained by diluting stationary-phase cells to $2 \times 10^8$ cells/ml in water, spotting $1 \times 10^6$ cells onto Medium 199, Lee's, spider and serum plates, and incubating them at 37° C. for 7 days. Solid medium 199 (M199 cat. no 31100-019, Invitrogen Corporation, Carlsbad, Calif.) was buffered with 150 mM Tris (pH 7) as previously described (Sharkey, L. L., et al., 1999. J Bacteriol 181:5273-9. Solid spider, serum and modified Lee's medium were prepared as described previously (Liu, H., J., et al., 1994. Science 266:1723-6).

Germ-tube formation was assessed at 37° C. in M199, modified Lee's, spider and serum media following inoculation of stationary-phase cells into pre-warmed broth at a density of $10^8$ cells/ml. Negative controls were incubated in the same medium at 28° C.

All chemicals and antibiotics were from Roche Diagnostic (Perkin Elmer Roche, Branchburg, N.J.,) and Sigma-Aldrich (Milano, Italy). Microbiological powders (except M199) were from Becton Dickinson (Becton Dickinson & Co., Sparks, Md.).

Generation of Recombinant Proteins.

The plasmids pRLV126 and pRLV130 were used for molecular cloning of enolase and MP65, as detailed elsewhere (LaValle, R., S. et al., 2000. Infect Immun 68:6777-84; Sandini, S., et al., 2002. Med Mycol 40:471-8).

In order to clone the mature form of CaMP65 in *E. coli*, the 1200 bp DNA fragment spanning from the secreted N-terminal sequence to the stop codon of CaMP65 was amplified by using Ca69 and Ca65 oligonucleotides (Table 1. The PCR product, after digestion with BamHI and HindIII, was cloned into the corresponding sites of pDS56-RBSII to give pRLV148.

For molecular cloning of proteinase SAP2 coding sequence, the full length SAP2 cds were amplified by using Ca70 and Ca71 oligonucleotides. After partial digestion with BamHI and PstI, SAP2 mature form was cloned into the corresponding sites of pDS56-RBSII to give pRLV 143.

TABLE 1

| ID | Sequence | Restrict Enzyme | CaMP65 Position start = 1 stop = 1138 | CaSAP2 Position start = 1, stop = 1198 |
|---|---|---|---|---|
| Ca70 | GGGGGATCCATGTTTTTAAAG AATATTTTCATTG -SEQ ID No. 1 | BamHI | | 1-25 |
| Ca71 | CCTAAGCTTAGGTCAAGGCAG AAATACTGGAAGCAG -SEQ ID No. 2 | HindIII | | 1216-1198 |
| Ca69 | CCCGGATCCCTGTTCATGTTGT TACC -SEQ ID No. 3 | BamHI | 98-114 | |

TABLE 1-continued

| ID | Sequence | Restrict Enzyme | CaMP65 Position start = 1 stop = 1138 | CaSAP2 Position start = 1, stop = 1198 |
|---|---|---|---|---|
| Ca65 | GGGCTGCAGGTGCTTAGTTAG AGTAA -SEQ ID No. 4 | PstI | 1142-1125 | |

Prior to use, all DNA inserts of pRLV143 and pRLV148 were sequenced to confirm homology to the known genes. Few difference have been observed but none of them confer amino acid changes in the encoded products.

Expression and Purification of Recombinant C. Albicans Proteins.

Expression of recombinant proteins was obtained in E. coli M15 carrying the lac repressor-producing pUHA1 plasmid (Hochuli, et al., 1988. J Chromatogr., 444:293-302). Induction was performed in LB medium, containing kanamycin and ampicillin, by adding isopropyl-13-D-thio-galactopyranoside (IPTG; Boehringer) at a final concentration of 1 mM to a culture with a O.D.$_{600}$ of 0.7, followed by further 5 hours of incubation at 37° C. Recombinant 6× his-tagged proteins were purified by nickel-chelate affinity chromatography as from manufacturer instructions (Qiagen; denaturing conditions). Fractions containing the purified polypeptide was pooled and precipitated with 3 volumes of absolute ethanol, resuspended in water and stored at −20° C.

Refolding of Recombinant C. Albicans Proteins.

The purified proteins dissolved in 8M urea were refolded by dialyses against decreasing concentrations of urea (4M, 2M, 1M, 0.5M) in PBS at 4° C., with samples incubated for 6 h at each urea concentration, followed by a final dialysis against PBS (Sigma-Aldrich) (10 mM phosphate buffer; 2.7 mM KCl; 137 mM NaCl; pH7.4).

Generation of Phage Display dAb Libraries.

The dAb phage libraries were based on a single human antibody framework for VH (V3-23 [locus] DP47 [V Base entry] and J$_H$4b) and for VL (012/02 [locus] DPκ9 [V Base entry] and JK1) with diversity incorporated using DNA nucleotide diversification to generate amino acid side chain diversity at positions that are known to make protein contacts with antigen in known molecular structures and are naturally diversified in the mature human repertoire. The dAb variable domains were cloned into the phage vector pDOM4 which is based on the fd-phage genome and therefore contains all the necessary phage genes to produce infective phage particles used during the selection process.

dAb Selection by Phage Display.

Selections were performed against passively coated MP65 and SAP2 on Maxisorp Immuno™ Tubes immunotubes (Nunc) 4 ml of both antigens at 10 μg/ml in BupH carbonate-bicarbonate buffer (0.2M Carbonate-Bicarbonate Buffer, pH 9.4) (Perbio, UK) were used to coat immunotubes overnight at 4° C. The immunotubes were subsequently blocked with PBS containing 2% skim-milk powder (PBSM) for 1 h at room temperature and washed 3 times with PBS. Approximately 1×10$^{11}$ phage from each dAb library, in total volume of 1 ml 2% PBSM, was incubated in the antigen coated tube for 1 h at room temperature (RT) by rotating at 50 rpm. After ten washes with PBS supplemented with 0.1% Tween-20 (Sigma-Aldrich) (PBST) and ten washes with PBS for round 1 selection (twenty washes for round 2 and 3 selections respectively), bound phage were eluted with 500 μl of PBS containing 1 mg/ml trypsin (Sigma-Aldrich) supplemented with 0.1 mM CaCl2 (Sigma-Aldrich) with rotation at 50 rpm at RT for 10 min. The trypsin solution containing the eluted phage was recovered and 250 μl used to infected 1.75 ml of log phase E. coli TG1 cells at 37° C. for 30 min. Library plating and serial log dilutions (for phage titre) and were done on 2×TYE-agar plates (15 g Bacto-Agar, 8 g NaCl, 10 g tryptone, 5 g Yeast Extract in 1 liter water) supplemented with 15 μg/ml tetracycline (Sigma-Aldrich). For subsequent selection rounds, cells were recovered from the growth plates by scraping into 2 ml 2×TY (16 g tryptone, 10 g yeast extract and 5 g NaCl in 1 liter water) media supplemented with 20% glycerol (Sigma-Aldrich) of which 50 μl was used to inoculate 50 ml of 2×TYE-Tet at 37° C. for phage amplification.

Following the desired number of selection rounds (typically 2 to 3) the enriched dAb genes were recovered by digesting 20 μg of purified (QIAgen Midiprep) dAb phage DNA from the desired selection output with SalI and NotI (NEB) restriction enzymes in NEB3 buffer (1 μg/ml BSA, 10 mM NaCl, 50 mM Tris-HCl, 10 mM MgCl$_2$, 1 mM dithiothreitol, pH 7.9@25° C.). The excised dAb genes were electrophoresed on a 1% agarose (Sigma-Aldrich) gel in TBE (Sigma-Aldrich) (44.5 mM Tris-borate and 1 mM EDTA, pH8.3) at 150V for 1 h. Following electrophoresis the dAb genes were excised and purified using the QIAgen gel purification kit (QIAgen). One hundred nano-grams of the purified digested dAb genes were then ligated with 400 ng of SalI/NotI digested soluble expression vector using T4 DNA ligase (New England Biolabs) in ligation buffer (50 mM Tris-HCl, 10 mM MgCl2, 1 mM ATP, 10 mM dithiothreitol, 25 μg/ml BSA, pH7.5 (25° C.) at RT for 1 hour. Three microlitres of ligation product were used to transform 50 μl of electrocompetent E. coli HB2151 (200Ω, 25 μFd, 2.5 kV, 0.2 cm gap cuvettes) and the desired amount of transformed cells plated onto agar plates supplemented with 5% glucose and 50 μg/ml carbenicillin (Sigma-Aldrich); followed by incubation at 37° C. for overnight.

Specific dAb Binders Screening by ELISA.

Fresh E. coli HB2151 clones were analysed for MP65 and SAP2 binding dAbs by ELISA. Individual clones were grown in 200 μl of 2×TY containing 50 μg/ml carbenicillin, 0.1% glucose in 96-well microtitre plates (Corning) at 37° C. with shaking at 250 rpm for 6 hours and induced with IPTG at final concentration of 1 mM, incubation continued at 30° C./250 rpm overnight to express soluble dAb. The plates were centrifuged at 870×g for 10 min at RT and the supernatant analysed by ELISA as follows (unless stated all volumes were 50 μl/well). Ninety-six well ELISA plates (Nunc Maxisorp) were coated overnight at 4° C. with 1 μg/ml MP65 or SAP2 in BupH carbonate-bicarbonate buffer then washed three times by immersion in PBST. Plates were then blocked with 200 μl/well PBS supplemented with 2% (v/v) Tween-20 for 1 h at room temperature, then washed 3 times with PBST. Twenty-five microlitres of supernatant from the overnight culture was diluted 1:1 in PBST and added into each well and incubated for 1 h at RT. Following three washes with PBST, bound SAP2 specific dAbs were incubated for 1 h at RT with 1:2000 dilution of Protein-A Horse Radish Peroxidase conjugate in PBST. Whereas dAbs selected against MP65 were detected using 1:2000 dilution of mouse 9E10 antibody (anti-myc, Sigma-Aldrich, Cat No M5546) in PBST for 1 h at RT, washed 3 times with PBST then a 1:2000 dilution of anti-mouse Fc-specific Horse Radish Peroxidase conjugate (Sigma-Aldrich, Cat No A0168) in PBST add and incubated at RT for 1 hour. Following incubation with the appropriate detection ligand, both SAP2 and MP65 assays were washed 3 times with PBST followed by 3 washes with PBS. All plates were then developed by adding 50 µl/well of TMB substrate (SureBlue, KPL, MD. USA). The reaction was allowed to develop for several minutes until a sufficient signal had appeared relative to the control wells, then the reaction stopped by the addition of 100 µl/well 1M HCl. Absorbance was read at 450 nm on a Victor2 microtitre plate reader (Perkin Elmer).

Expression and Purification of dAb Protein

Individual fresh colonies corresponding to each soluble dAb ELISA positive clone was inoculated into 5 ml of 2×TY supplemented with 50 µg/ml carbenicillin and 5% glucose and incubated overnight at 37° C. with shaking at 250 rpm. Five millilitres of this culture was used to inoculate 500 ml of fresh pre-warmed media (2×TY supplemented with 50 µg/ml carbenicillin and 0.1% glucose) and incubated at 37° C. with shaking at 250 rpm until the OD600 reached 0.8, when the culture was induced through the addition of IPTG to a final concentration of 1 mM and incubated overnight at 30° C. with shaking at 250 rpm. The cells were then pelleted by centrifugation at 3450×g for 10 minutes and the resulting clarified supernatant filtered through a 0.45 µm sterile filter. Fifty millilitres of this supernatant was then mixed by rotation at 50 rpm with 200 µl of Protein-L-sepharose (Sigma-Aldrich) for VL dAbs or Protein-A streamline (Amersham Pharmacia) for VH dabs at RT for 1 hour. The resins were recovered by centrifugation at 220×g for 1 min, followed by washing twice with 1 ml of 0.5M NaCl in PBS and twice with 1 ml of PBS in 96 well paper-filter plate (Whatman) then the dAb eluted with 210 µl of 0.1M Glycine (pH2.0) and neutralized by adding 40 µl of 1M Tris-HCl (pH8.0). The purity of the dAbs was determined by SDS-PAGE performed under reducing conditions using 12% NuPAGE Bis-Tris gels run in MES buffer (Novex gel system, Invitrogen). Gels were stained with Coomassie blue (Simply Blue Safestain, Invitrogen). The concentration of the dAb samples were determined by absorbance at 280 nm.

Adherence Assays to Endothelial Cells or Plastic.

The fungal cells were grown at 28° C. on YPD agar slants (2.0% wt/vol glucose, 1.0% wt/vol yeast extract, 2.0 wt/vol Bacto peptone, (Difco, Detroit, Mich.). Single suspensions of each organism were prepared by a modification of the procedure of Rotronsen (Rotronsen, D., et al. 1986. Rev Infect Dis.; 8:73-85). Briefly, cells were grown 24 h at 28° C. on a rotating drum in YBD broth pH5.0 (0.2% wt/vol yeast extract, 2.0% wt/vol BSA and 2.0% wt/vol dextrose, (Difco, Detroit, Mich.). After harvesting by centrifugation, the *C. albicans* cells were washed three times in physiological solution (0.85% NaCl). Blastospores were counted with Thoma camera and adjusted to desired concentration ($10^8$ cells/ml) in Hank's Balanced Salt Solution with calcium and magnesium (Hyclone, Logan, Utah).

Human umbilical vein endothelial cells (HUVEC) were prepared by a modification of the method of Jaffe, et al. (Jaffe, et al., 1989. J. Immunol. 15; 143:3961-6). Briefly, HUVECs were obtained from umbilical cord vein by 0.5 mg/ml collagenase H digestion (Boehringer-Mannheim, Mannheim, Germany). Cells were routinely grown in 50% Medium-199, 50% D-Minimum Essential Medium (EuroClone, Yorkshire, United Kingdom) supplemented with 20% fetal bovine serum (Hyclone, Logan, Utah), 50 ng/ml heparin (Sigma) and 50 µg/ml ECGF (Becton Dickinson).

For Candidal adherence studies, cells were grown to confluence in 12-well tissue culture plates (Corning Incorporated, Corning, N.Y., USA) coated with 0.5% bacto gelatin (Difco, Detroit, Mich.). All incubations were in humidified 95% air, 5% CO2 atmosphere at 37° C.

For adherence to the plastic, the fungal cells, grown as above, were washed twice with water and suspended at 1.5× $10^3$ cells/ml in modified Lee's or M199 liquid media. $1.5 \times 10^3$ cells were incubated for 3 hrs at 37° C. in 6-well polystyrene plates (Corning Incorporated, Corning, N.Y.,). After extensive washing, 1 ml of Sabouraud dextrose agar was poured in each well and allowed to solidify. After incubation at 37° C. for 24 hrs, colonies were counted and the results expressed as percentage of the inoculum. The inoculum size of each cell suspension was confirmed by plating aliquots of the culture directly in Sabouraud dextrose agar plates.

ELISA

Binding was measured by an enzyme-linked immunosorbent assay (ELISA). Briefly, polystyrene microtitre plates (Dynatech, PBI, Milan, Italy) were coated overnight at 4° C. with 200 ng of antigen dissolved in 100 µl of 0.05M sodium carbonate (pH9.6). After a wash in bovine serum albumin-phosphate-buffered saline (PBS) blocking solution, 100 µl of twofold dilutions in PBS-0.05% Tween 20 of ascites from immunized animals was diluted and incubated at 37° C. for 2 h.

Pooled serum (diluted 1:2) from non-immunized mice was used as negative control. After three washes with 400 µl of PBS-Tween20, a 1:1.000 dilution in PBS of anti-mouse polyvalent alkaline phosphatase conjugate (Sigma) used as secondary antibody was added to wells 1 h at 37° C., and the reaction was developed with nitrophenyl phosphate disodium (Sigma) as the substrate. Titers were defined as the highest dilution of mouse serum which gave an optical reading of at least twice the reading of the negative control. For the immunoblotting, purified recombinant proteins from IPTG-induced M15 (pUHA1, pDS56/RBSH6xhis-ca) cells were resuspended in sample buffer at approximately 1 µg of protein per µl), boiled for 10 min, and subjected SDS-polyacrylamide gel electrophoresis (PAGE (5 to 15% polyacrylamide gradient)). The electrophoresed materials were electroblotted onto nitrocellulose filters in a buffer containing 25 mM Tris, 192 mM glycine, 0.1% SDS, and 20% methanol. Filters were incubated with ascites as detailed in single experiments. In all cases, non specific binding of ascites to nitrocellulose was prevented by blocking of the filters with 1% bovine serum albumin in phosphate-buffered saline (PBS) for 2 h at room temperature. After extensive washing with PBS-Tween20, bound antibodies were detected by 1:1000 dilution in PBS of anti-mouse polyvalent alkaline phosphatase conjugate (Sigma) used as secondary antibody.

Proteinase Enzyme Assay.

This was based on bovine serum albumin degradation by a native, highly purified SAP2 preparation, essentially as described by Ross et al. Briefly, each assay contained 0.6 ml of 1% (w/v) BSA (Sigma Chem. Co., Detroit, Mich.) in 50 mM sodium citrate pH 3.2 and 0.15 enzyme solution (100 µg/ml). After 30 min at 37° C. 0.4 ml 10% (w/v) trichloroacetic acid was added. The tubes were stored in ice for 30 min and then centrifuged (1600×g) for 10 min. The absorbance of supernatant was read at 280 nm. The control was 1% BSA in enzyme-free citrate buffer. One unit of enzyme catalysed a delta OD of 1 per minute. With our purified SAP2 preparation the assay was proportional to enzyme concentration over a delta OD range of 0.1-0.4 and the detection limit of 1 µg.

Rat Vaginal Infection.

Oophorectomized female Wistar rats (80-100 g, Charles River Breeding Laboratories, Calco, Italy) were used throughout this study. All rats were maintained under pseudoestrus by injection of estradiol benzoate (Amsa Farmaceutici srl, Rome, Italy).

Six days after the first estradiol dose, the animals were inoculated intravaginally with $10^7$ yeast cells in 0.1 ml of saline solution. The number of cells in the vaginal fluid was counted by culturing 10 µl samples (using calibrated plastic loop, Disponoic, PBI, Milan, Italy) taken from each animal, on Sabouraud agar plate containing chloramphenicol (50 µg/ml) as previously described (De Bernardis, et al. 1999. J Infect Dis. 179:201-8). The rat was considered infected when at least 1 CFU was detected in the vaginal lavage, i.e. a count of $\geq 10^3$ CFU/ml. Other vaginal samples were also stained by periodic acid-Schiff-van Gieson method for microscopic examination.

Example 2

Results 1. dAbs Generation, Screening and Characterization

Refolded recombinant *C. albicans* proteins were tested for functional activity prior to dAb selection by phage display. SAP2 was tested by proteinase enzyme assay and showed good functionality which indicated a correctly folded structure. MP65 was refolded using the same method for SAP2, however functionality was not tested due to the lack of a robust assay. Four phage libraries with a combined size of greater than $1 \times 10^{10}$ unique dAbs were used for selection with at least $1 \times 10^{11}$ individual phage used for each round of selection (representing at least a 10 fold overrepresentation of the library diversity). Following three rounds of selection, phage output titres had increased by more than 5 logs. Both MP65 specific and SAP2 specific dAbs were isolated from the third round selection output by screening bacterial culture supernatants containing the expressed dAb for binding to passively adsorbed antigen by ELISA. Ten unique MP65 specific binders (3 VH and 7 VK) and 27 unique SAP2 specific binders (22 VH and 5 VK) were identified. To determine the inhibitory activity of each dAb against its respective antigen, several milligrams of purified dAb were produced for each unique positive clone for screening.

2. dAbs Binding and Functional Properties.

Clones from two different phage expression libraries, comprising VH and Vk sublibraries selected against SAP2 or MP65 following appropriate screening by an immunoenzymatic method (see above) were in addition functionally screened. In the case of SAP2, the dAb capacity to inhibit the enzymatic activity of a native protein preparation was also assessed whereas for MP65, each dAb binder was also tested for inhibition of *Candida* adherence to the plastic. At the end of these preliminary assays, a limited number of each dAb family was therefore chosen, based on both their strong binding to the recombinant protein and their functional inhibitory capacity of adhesion and enzyme activity. However, it was envisaged that all dABs would function in both binding and functional assays.

By way of example, Table 2 shows the capacity of each selected single SAP2 binder to inhibit BSA degradation under acidic conditions, compared with the prototypal inhibitor of aspartic proteases pepstatin A.

TABLE 2

| SAMPLE | ΔOD/ml/min | % Inhibition |
|---|---|---|
| Citrate buffer + 1% BSA + SAP | 1.0 | — |
| Citrate buffer + 1% BSA + SAP + pepstatin | 0.36 | 100* |
| ADR4-11 | 0.80 | 29 |
| ADR4-12 | 0.60 | 60 |
| ADR4-13 | 0.46 | 82 |
| ADR4-3 | 0.66 | 40 |
| ADR4-4 | 0.76 | 32 |
| ADR4-5 | 1 | 0 |
| ADR4-6 | 0.50 | 78 |
| ADR4-7 | 0.70 | 61 |
| ADR4-8 | 1 | 0 |
| ADR4-9 | 0.93 | 5 |
| ADR4-10 | 0.83 | 13 |
| DUMMY | 0.93 | 5 |
| He14/pr2 | 1.16 | — |

The strongest pepstatin-relative dAbs ADR4-13 and ADR4-6 were selected and purified for further study. In the case of MP65 binders, the dAbs ADR3-1, ADR3-2 and ADR3-6 were instead selected on the basis of their capacity to inhibit adherence to plastic.

3. dAb Activity in the Rat Vaginal Candidiasis Model

The selected dAbs as described above were assayed for their capacity to accelerate fungus clearance from the rat vaginal cavity challenged by a virulent vaginopathic *Candida* strain. The controls were the use of an irrelevant dAb, and an anti-enolase antibody as negative ones and the antimycotic fluconazole and pepstatin A (the prototypal Sap inhibitor) as positive ones.

The interpretation of the results is based on two main criteria: 1. the accelerated clearance during early treatment, i.e. three-six days from the intravaginal challenge; 2. the healing of infection (<1 CFU/µl of vaginal fluid) on day 21 post challenge. The differences are assessed by both parametrical (Student's t test) and non-parametrical (Manner Whitney U test) statistics. Two types of experiments were done (repeated three times), one of preventative type and one of therapeutic type. In the former experiments, a single dAb (20 µg as protein) administration was given intravaginally 30 min before intravaginal *Candida* challenge whereas in the latter the same dAb amount was given at 1, 24 and 48 hrs after challenge.

4. dAb Preventative Activity

In an initial experiment whereby rats were pre-treated with either an anti-MP65 dAb (ADR3-2) or an anti-SAP2 dAb (ADR4-6) (FIG. 1), or treated with either fluconazole or pepstatin, both dAbs were shown to accelerate *Candida* elimination from the vagina with a kinetics substantially equivalent to that of both the antimycotic and pepstatin (FIG. 1). All treatments did appear to resolve the infection on day 21st, whereas all control (untreated) rats were still infected on day 28th. Subsequent experiments were intended to analytically examine the activity of each single dAb, and also to examine whether the dAbs exerted therapeutic activity, i.e. when given after challenge.

Figure 2:
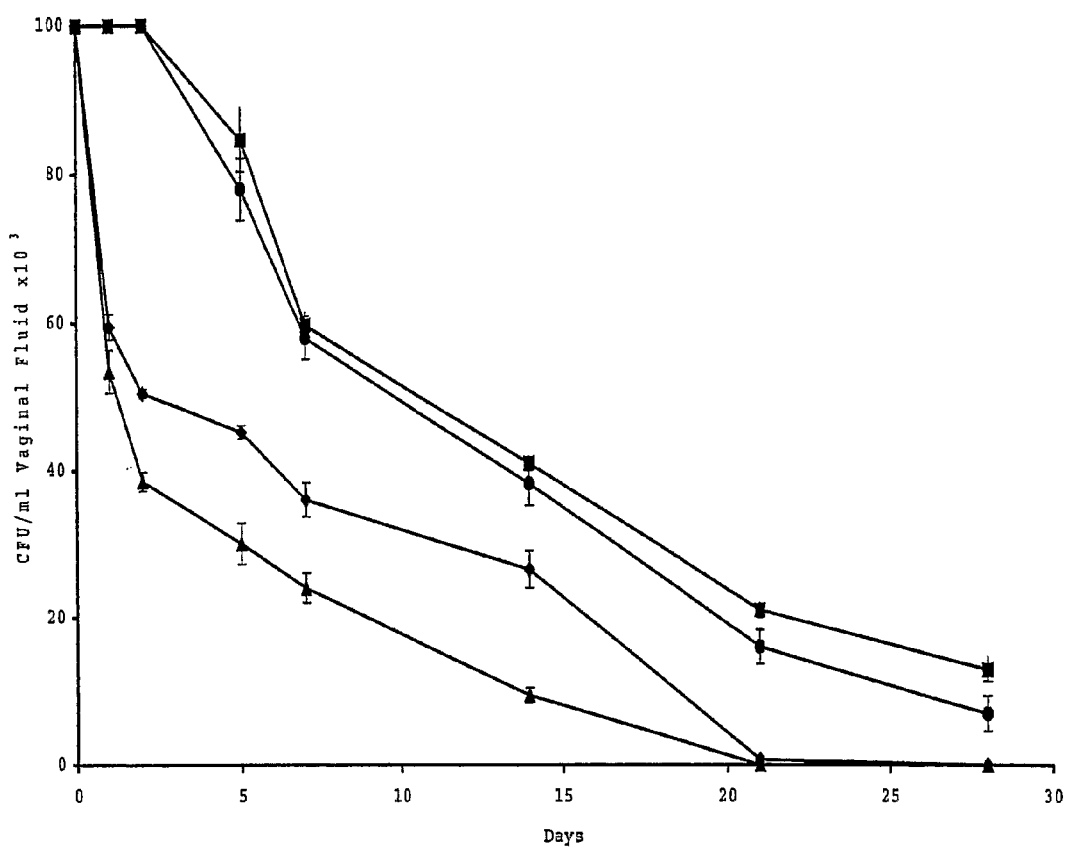
FIG. 2: Vaginal infection with *C. albicans* in rats treated intravaginally with anti-SAP2 dAbs ADR4-6 (triangle) or ADR4-13 (diamonds). Controls were irrelevant dAb Hel4 (circle) or untreated, only challenged with *C. albicans* (squares).

As shown in FIG. 2, both anti-SAP2 dabs (ADR4-6 or ADR4-13) conferred high preventive protection against the fungal challenge, as exemplified by more rapid initial clearance of the fungus and anticipated clearance of infection (day 21) as compared to the control, untreated or irrelevant-dAb treated rats. Comparing the two dAbs, there was no statistically significant difference between them. For instance, in the experiment illustrated in FIG. 2, there was a borderline statistically significant difference (P=0.048; Student's t test) on day 14 only between the vaginal *Candida* CFU in the animals given the two dAbs, but it was not reproduced in additional experiments.

The three selected anti-MP65 dAbs were also markedly active in the rat vaginal candidiasis model, with generally similar behaviour and capacity to accelerate fungal clearance from vagina. Although the rats pre-treated with the dAb ADR3-2 were still infected on day 21st, they were similarly cured, as all other rats pre-treated with the other two anti-MP65 dAbs, on the subsequent day (day 28th) of observation (FIG. 3).

Figure 4:
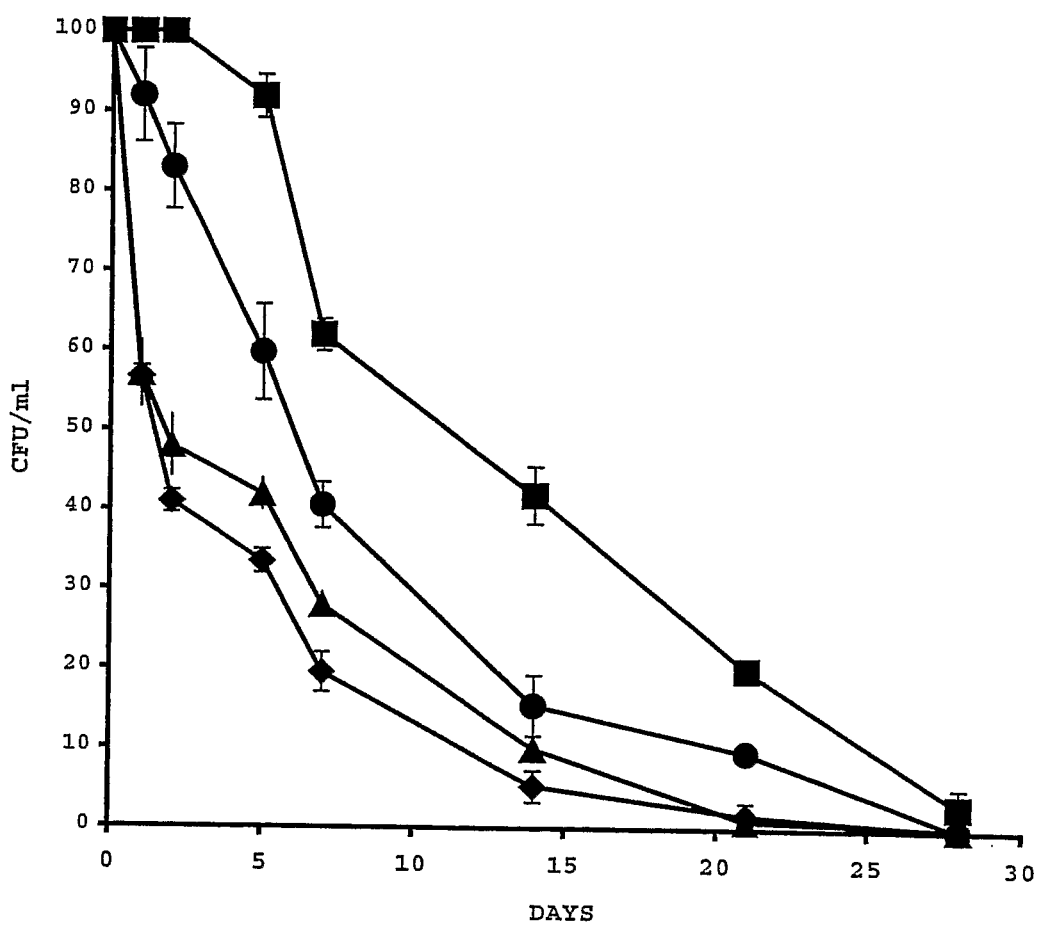
FIG. 4: Vaginal infection with a fluconazole-resistant strain (AIDS 68) of *C. albicans* and treated with anti-SAP2 dAbs; diamonds AIDS68+ADR4-6; triangles AIDS68+ADR4-13; squares AIDS68; circles AIDS68+fluconazole.

In addition, and as expected from the putative mechanism of dAb action (inhibition of SAP2 activity) both ADR4-6 and ADR4-13 were highly efficacious even against the infection caused by a fluconazole-resistant *Candida* strain AIDS 68, with strong acceleration of fungus clearance and premature healing of infection (FIG. 4).

dAb Therapeutic Activity

Figure 5:
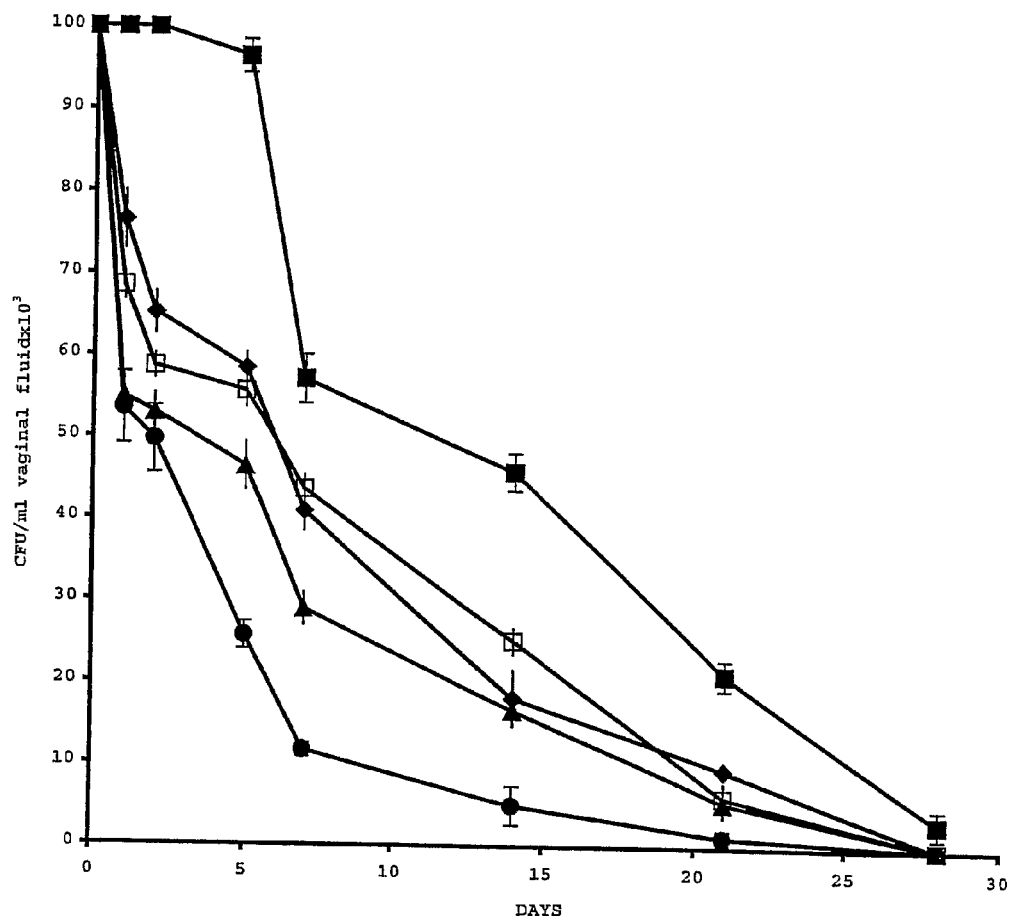
FIG. 5: Vaginal infection with *C. albicans* SA40 in rats intravaginally treated with dAbs after challenge (1, 24, 48 Hrs) (closed squares: SA40 fungal challenge only; diamond: ADR4-6; open squares: ADR3-6 dAb; triangles: ADR4-6 and ADR3-6) dAbs; circles: fluconazole).

Further experiments were performed to assess the dAb potential to exert a curative effect when administered after *Candida* challenge. Each dAb was therefore administered at 1, 24 and 48 hours post-infection. As shown in FIG. 5, this treatment also provided an acceleration of fungus clearance from vagina as compared to the untreated or irrelevant dAb-treated rats. Although the rate of clearance here appeared to be inferior, whichever the dAb used, to that achieved with corresponding dAb pre-treatment, nonetheless full cure of infection was also obtained before the controls, though only on day 28. In this therapeutic approach, no statistically significant differences were observed between the anti-SAP2 and anti-MP65 dAbs), but fluconazole was significantly more active in reducing the number of vaginal CFU at all times examined. There was also no apparent advantage in treating with a mixture of anti-SAP2 and anti-MP65 dAbs. Nonetheless, all treated rats were cured of the infection on day 28.

Systemic Control of *Candida* Infection

The ability of anti-SAP2 and anti-MP65 dAbs to control a systemic infection of *C. albicans* was assessed using standard methods.

Briefly, mice were chronically infected with *C. albicans* by injecting $1 \times 10^6$ cells per mouse via the lateral tail vein (in 0.2 ml saline). Anti-SAP2 or anti-MP65 dAbs were administered as previously indicated. Survival rates compared with control animals were measured.

Further, it is envisaged that the dAbs can be used to confer passive protection against fungal infection in vulnerable subjects by administering an effective dose prior to any possible infection. An effective dose can be determined by means known to those skilled in the art.

Mice were dosed with either 1 mg/kg or 10 mg/kg of either anti-SAP2 or anti-MP65 dAb, followed by a dose of *C. albicans* by injecting $1 \times 10^6$ cells per mouse via the lateral tail vein (in 0.2 ml saline). Fungal infection and survival rates compared to controls were measured. It was observed that both anti-SAP2 and MP65 dAbs protected the mice against fungal infection when compared with the controls.

Example 3

Heterodimer Construction

DNA encoding the dabs ADR3-6 and ADR4-6 was cloned sequentially in both orientations into the expression vector pDOM5D-5U to generate two separate constructs (ADR3-6/ADR4-6 and ADR4-6/ADR3-6). This vector was based on pDOM5 (as pDOM4 described in the examples for monomer production but without the phage expression coding) and contained a linker situated between the dAb cloning sites.

Protein Expression:

Expression and purification as described for the monomer dabs using protein-A. Confirmation of protein purity was by SDS-PAGE with coomassie staining.

In Vivo Analysis:

Five oophorectomized female Wistar rats (80-100 g, Charles River Breeding Laboratories, Calco, Italy) per group were used. Animal maintenance and overall care was as described elsewhere (De Bernardis, F., et al. J. Infect. Dis. 161, 1276-1283 (1990). All rats were maintained under pseudo-oestrus by subcutaneous injections of 50 mg of oestradiol benzoate (Amsa Farmaceutici srl, Rome, Italy) given every second day. Six days after the first estradiol dose, the rats were administered intravaginally with 20 µg (in 0.1 ml of saline) of each dimer molecule 30 min before intravaginal challenge with $10^7$ *Candida albicans* cells (strain SA-40) in 0.1 ml of saline solution. The number of cells in the vaginal fluid was counted by culturing 10 µl samples (using a calibrated plastic loop, Disponoic, PBI, Milan, Italy) taken from each animal on Sabouraud agar plates containing chloramphenicol (50 µg/ml). Rats were considered infected when at least 1 CFU was detected in the vaginal lavage, i.e. a count of $>10^3$ CFU/ml.

Results

Figure 6:
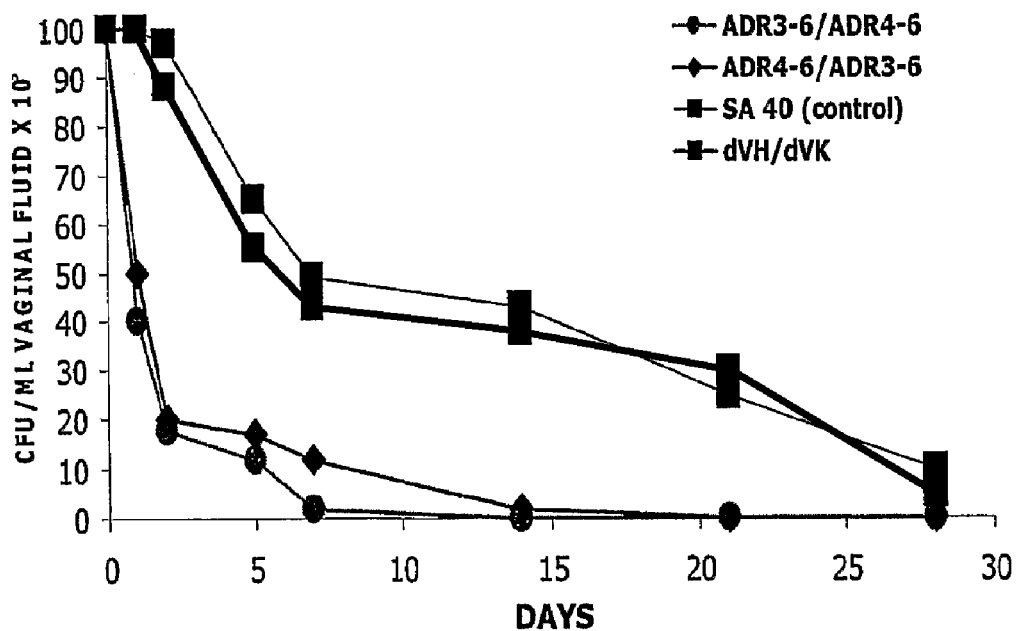
FIG. 6: *C. albicans* infection treated with heterodimer dAbs (circles ADR3-6/ADR4-6; diamonds ADR4-6/ADR3-6; squares with light lines, SA40 (control); squares with heavy line, heterodimer dAbs VH-VL (control)).

Both heterodimers were able to accelerate the clearance of *Candida* (FIG. 6). The heterodimer ADR3-6/ADR4-6 cleared the infection to below the detectable limit by ~day 10. The heterodimer ADR4-6/ADR3-6 cleared infection by day 15.

All publications mentioned in the present specification and references cited in said publications are herein incorporated by reference. Various modifications and variations of the described methods and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in the field or related fields are intended to be within the scope of the following claims.

Example 4

Generation of PEGylated Monospecific and Heterodimer dAb Formats

The DNA sequence encoding individual dAbs, cloned in the expression vector pDOM5, were mutated by PCR to change the codon encoding the final dAb framework 4 amino acid (typically a serine for VH dAbs and arginine for VK dAbs) to a cystein ( . . . TGC . . . codon). Two stop codons ( . . . TAATAA . . . ) were included immediately 3' of the TGC codon. A similar approach was used to introduce a cysteine into the 3' dAb of the heterodimer constructs.

Protein Expression:

Expression and purification of the mutated monomer constructs was as described for the monomer dAbs, using protein-A for VH clones or protein-L for VK clones. Expression and purification of the mutated dimer constructs was as described for the monomer dabs using protein-A. For both mutated monomer and dimer constructs, protein purity was assessed by SDS-PAGE with coomassie staining.

PEGylation:

dAbs in both monomeric form and dimeric form where PEGylated using standard maleimide linker chemistry. The PEG was bound to either cysteine or lysine which was either nature or added to the dAb. If the cysteine or lysine was added it was added at the N or C terminal of the dAb or within the framework of the dAb.

Once PEGylated the dAbs were purified and isolated before use by using a standard SEC purification technique.

Results:

PEGylated versions of both monomer and dimer constructs were assayed for efficacy in controlling a systemic *C. albicans* infection in Balb/c mice, using a protocol similar to the murine systemic model described above. One mg/kg of PEGylated dAb protein or fluconazole was administered at 2 h, 6 h and 24 h post infection to groups of 8 mice. The dual specific heterodimer construct ADR4-6/ADR3-6-PEG showed the most potent activity. This molecule was more efficacious than its constituent monomers or fluconazole.

| Sample | Survival | Mean Survival Time (days) |
| --- | --- | --- |
| dAb diluent (PBS) | 50% | 2 |
| ADR3-1- PEG | 75% | >30 |
| HEL4- PEG | 62% | >30 |
| ADR3-6- PEG | 62% | >30 |
| ADR4-6- PEG | 88% | >30 |
| ADR4-6\ADR3-6- PEG | 88% | >30 |
| ADR4-13- PEG | 50% | 4 |
| ADR3-6\ADR4-6- PEG | 100% | >30 |
| Fluconazole | 88% | >30 |
| SA 40 only | 25% | 2 |
| Uninfected mice | 100% | — |

---

The invention claimed is:

1. A single domain antibody (dAb) which binds to a secretory aspartic protease (Sap) from *Candida* spp.

2. The single domain antibody (dAb) according to claim 1 which binds to Sap2.

3. The single domain antibody (dAb) according to claim 2 which comprises an amino acid sequence selected from the group consisting of ADR4-2 (SEQ ID NO:14), ADR4-3 (SEQ ID NO:15), ADR4-4 (SEQ ID NO:16), ADR4-6 (SEQ ID NO:18), ADR4-7 (SEQ ID NO:19), ADR4-9 (SEQ ID NO:21), ADR4-10 (SEQ ID NO:22), ADR4-11 (SEQ ID NO:23), ADR4-12 (SEQ ID NO:24), ADR4-13 (SEQ ID NO:25), ADR4-14 (SEQ ID NO:26), ADR4-15 (SEQ ID NO:27), ADR4-16 (SEQ ID NO:28), ADR4-17 (SEQ ID NO:29), ADR4-18 (SEQ ID NO:30), ADR4-19 (SEQ ID NO:31), ADR4-20 (SEQ ID NO:32), ADR4-21 (SEQ ID NO:33), ADR4-22 (SEQ ID NO:34), and ADR4-23 (SEQ ID NO:35).

4. The single domain antibody (dAb) according to claim 2 which comprises the amino acid sequence ADR4-6 (SEQ ID NO:18) or ADR4-13 (SEQ ID NO:25).

5. The single domain antibody (dAb) according to claim 1 wherein the dAb binds to a Sap with a $K_{off}$ rate constant of between $5 \times 10^{-1}$ and $1 \times 10^{-7}$ $s^{-1}$.

6. The single domain antibody (dAb) according to claim 1 which binds to a Sap with a dissociation constant (Kd) of at least 100 μM to 1 pM.

7. The single domain antibody according to claim 5 which binds to Sap2.

8. The single domain antibody (dAb) according to claim 1 which comprises an amino acid sequence that has at least 80% amino acid sequence identity to the sequence ADR4-6 (SEQ ID NO:18) or ADR4-13 (SEQ ID NO:25.

9. The single domain antibody (dAb) according to claim 1 which inhibits the functional activity of the secretory aspartic protease (Sap) from *Candida* spp.

10. The single domain antibody (dAb) according to claim 9 which inhibits the functional activity of Sap2.

11. A pharmaceutical composition comprising one or more dAbs according to claim 1 and a pharmaceutically acceptable carrier, diluent and/or excipient.

12. The pharmaceutical composition according to claim 11 further comprising one or more dAbs which bind to mannoprotein adhesin (MP65) from *Candida* spp.

13. A method for the prophylaxis and/or treatment of *Candida* spp. infection in a patient comprising administering to a patient in need of such treatment one or more dAbs which bind to a secretory aspartic protease (Sap) from *Candida* spp. or administering one or more dAbs which bind to a Sap and one or more dAbs which bind to mannoprotein adhesion (MP) from *Candida* spp.

14. The method according to claim 13, wherein said *Candida* spp. infection is an azole resistant *Candida* spp. infection.

15. The method according to claim 14 wherein the azole is a triazole.

16. The method according to claim 15 wherein the triazole is selected from the group consisting of itraconazole, fluconazole and voriconazol.

17. The method according to claim 14, wherein said *Candida* spp. infection is an imidazole resistant *Candida* spp. infection that is resistant to one or more agents in the group consisting of Clotrimazole, econazole, fenticonazole, sulconazole and tioconazole.

18. The method according to claim 13 wherein the *Candida* spp. is one or more of those selected from the group consisting of *Candida albicans, Candida tropicalis, Candida glabrata, Candida parapsilosis, Candida krusei* and *Candida lusitaniae.*

19. The method according to claim 18 wherein the *Candida* spp. is *Candida albicans.*

20. The method according to claim 13 wherein the *Candida* spp. infection is in any one or more of the locations selected from the group consisting of systemic, mucosal, oral, under the nails, bronchial, pulmonary, vaginal, vulvovaginal, esophageal and oropharyngeal.

21. The method according to claim 20 wherein the *Candida* spp. infection is systemic or mucosal.

22. The method according to claim 21 wherein the *Candida* spp. infection is systemic.

23. The method according to claim 13 wherein the dAb is administered to the subject by systemic administration, topical administration, oral administration, intranasal administration or mucosal administration.

24. The method according to claim 23 wherein the dAb is administered to the subject by oral administration.

25. The method according to claim 23 wherein the dAb is administered to the subject by systemic administration.

26. A method for the prophylaxis and/or treatment of one or more conditions associated with immune compromised patients comprising administering to a patient in need of such treatment one or more dAbs which bind to a secretory aspartic protease (Sap) from *Candida* spp. or administering one or more dAbs which bind to a Sap and one or more one or more dAbs which bind to mannoprotein adhesion (MP) from *Candida* spp.

27. The method according to claim 26 wherein the immune compromised patient is suffering from one or more conditions selected from the group consisting of HIV infection, AIDs and yeast infection.

28. The method according to claim 26 wherein the dAb is administered to the patient in the form of a single dose.

29. The method according to claim 26 wherein the dAb is administered to the patient in the form of a single dose followed by multiple dose administration.

30. A method for the prophylaxis and/or treatment of systemic *Candida* spp. infection in a patient wherein the method comprises the step of administering to the patient in need of such treatment one or more of:
  (i) An antibody which binds to a secretory aspartic protease protein of *Candida* spp. (Sap) protein;
  (ii) A fragment of an antibody which binds to a Sap protein; and (iii) A dAb which binds to a Sap protein and a dAb which binds to a mannoprotein adhesion protein (MP) of *Candida* spp.

31. The method of claim 30 wherein said antibody, fragment of an antibody and dAb inhibit the functional activity of a Sap and/or MP protein.

32. The method according to claim 30 wherein the dAb is administered systemically.

33. The method according to claim 30 wherein the antibody is mono-specific.

34. The method according to claim 30 wherein the Sap is Sap2.

35. The method according to claim 30 wherein the MP protein is MP65.

36. A method for the prophylaxis and/or treatment of *Candida* spp. infection or colonization of a medical device comprising administering to the device one or more dAbs selected from the group consisting of dAbs which bind to a secretory aspartic protease (Sap) from *Candia* spp. or administering one or more dAbs which bind to a Sap and one or more dAbs which bind to mannoprotein adhesion (MP) from *Candida* spp.

37. The dAb according to claim 1, wherein the dAb has an amino acid sequence that differs from the amino acid sequence of ADR4-2 (SEQ ID NO:14), ADR4-3 (SEQ ID NO:15), ADR4-4 (SEQ ID NO:16), ADR4-6 (SEQ ID NO:18), ADR4-7 (SEQ ID NO:19), ADR4-9 (SEQ ID NO:21), ADR4-10 (SEQ ID NO:22), ADR4-11 (SEQ ID NO:23), ADR4-12 (SEQ ID NO:24), ADR4-13 (SEQ ID NO:25), ADR4-14 (SEQ ID NO:26), ADR4-15 (SEQ ID NO:27), ADR4-16 (SEQ ID NO:28), ADR4-17 (SEQ ID NO:29), ADR4-18 (SEQ ID NO:30), ADR4-19 (SEQ ID NO:31), ADR4-20 (SEQ ID NO:32), ADR4-21 (SEQ ID NO:33), ADR4-22 (SEQ ID NO:34), or ADR4-23 (SEQ ID NO:35) at no more than 25 amino acid positions, and has a CDR1 sequence that has at least 50% identity to the CDR1 sequence of ADR4-2 (SEQ ID NO:14), ADR4-3 (SEQ ID NO:15), ADR4-4 (SEQ ID NO:16), ADR4-5 (SEQ ID NO:17), ADR4-6 (SEQ ID NO:18), ADR4-7 (SEQ ID NO:19), ADR4-8 (SEQ ID NO:20), ADR4-9 (SEQ ID NO:21), ADR4-10 (SEQ ID NO:22), ADR4-11 (SEQ ID NO:23), ADR4-12 (SEQ ID NO:24), ADR4-13 (SEQ ID NO:25), ADR4-14 (SEQ ID NO:26), ADR4-15 (SEQ ID NO:27), ADR4-16 (SEQ ID NO:28), ADR4-17 (SEQ ID NO:29), ADR4-18 (SEQ ID NO:30), ADR4-19 (SEQ ID NO:31), ADR4-20 (SEQ ID NO:32), ADR4-21 (SEQ ID NO:33), ADR4-22 (SEQ ID NO:34), or ADR4-23 (SEQ ID NO:35).

38. The dAb according to claim 1, wherein the dAb has an amino acid sequence that differs from the amino acid sequence of ADR4-2 (SEQ ID NO:14), ADR4-3 (SEQ ID NO:15), ADR4-4 (SEQ ID NO:16), ADR4-6 (SEQ ID NO:18), ADR4-7 (SEQ ID NO:19), ADR4-9 (SEQ ID NO:21), ADR4-10 (SEQ ID NO:22), ADR4-11 (SEQ ID NO:23), ADR4-12 (SEQ ID NO:24), ADR4-13 (SEQ ID NO:25), ADR4-14 (SEQ ID NO:26), ADR4-15 (SEQ ID NO:27), ADR4-16 (SEQ ID NO:28), ADR4-17 (SEQ ID NO:29), ADR4-18 (SEQ ID NO:30), ADR4-19 (SEQ ID NO:31), ADR4-20 (SEQ ID NO:32), ADR4-21 (SEQ ID NO:33), ADR4-22 (SEQ ID NO:34), or ADR4-23 (SEQ ID NO:35) at no more than 25 amino acid positions, and has a CDR2 sequence that has at least 50% identity to the CDR2 sequence of ADR4-2 (SEQ ID NO:14), ADR4-3 (SEQ ID NO:15), ADR4-4 (SEQ ID NO:16), ADR4-5 (SEQ ID NO:17), ADR4-6 (SEQ ID NO:18), ADR4-7 (SEQ ID NO:19), ADR4-8 (SEQ ID NO:20), ADR4-9 (SEQ ID NO:21), ADR4-10 (SEQ ID NO:22), ADR4-11 (SEQ ID NO:23), ADR4-12 (SEQ ID NO:24), ADR4-13 (SEQ ID NO:25), ADR4-14 (SEQ ID NO:26), ADR4-15 (SEQ ID NO:27), ADR4-16 (SEQ ID NO:28), ADR4-17 (SEQ ID NO:29), ADR4-18 (SEQ ID NO:30), ADR4-19 (SEQ ID NO:31), ADR4-20 (SEQ ID NO:32), ADR4-21 (SEQ ID NO:33), ADR4-22 (SEQ ID NO:34), or ADR4-23 (SEQ ID NO:35).

39. The dAb according to claim 1, wherein the dAb has an amino acid sequence that differs from the amino acid sequence of ADR4-2 (SEQ ID NO:14), ADR4-3 (SEQ ID NO:15), ADR4-4 (SEQ ID NO:16), ADR4-6 (SEQ ID NO:18), ADR4-7 (SEQ ID NO:19), ADR4-9 (SEQ ID NO:21), ADR4-10 (SEQ ID NO:22), ADR4-11 (SEQ ID NO:23), ADR4-12 (SEQ ID NO:24), ADR4-13 (SEQ ID NO:25), ADR4-14 (SEQ ID NO:26), ADR4-15 (SEQ ID NO:27), ADR4-16 (SEQ ID NO:28), ADR4-17 (SEQ ID NO:29), ADR4-18 (SEQ ID NO:30), ADR4-19 (SEQ ID NO:31), ADR4-20 (SEQ ID NO:32), ADR4-21 (SEQ ID NO:33), ADR4-22 (SEQ ID NO:34), or ADR4-23 (SEQ ID NO:35) at no more than 25 amino acid positions, and has a CDR3 sequence that has at least 50% identity to the CDR3 sequence of ADR4-2 (SEQ ID NO:14), ADR4-3 (SEQ ID NO:15), ADR4-4 (SEQ ID NO:16), ADR4-5 (SEQ ID NO:17), ADR4-6 (SEQ ID NO:18), ADR4-7 (SEQ ID NO:19), ADR4-8 (SEQ ID NO:20), ADR4-9 (SEQ ID NO:21), ADR4-10 (SEQ ID NO:22), ADR4-11 (SEQ ID NO:23), ADR4-12 (SEQ ID NO:24), ADR4-13 (SEQ ID NO:25), ADR4-14 (SEQ ID NO:26), ADR4-15 (SEQ ID NO:27), ADR4-16 (SEQ ID NO:28), ADR4-17 (SEQ ID NO:29), ADR4-18 (SEQ ID NO:30), ADR4-19 (SEQ ID NO:31), ADR4-20 (SEQ ID NO:32), ADR4-21 (SEQ ID NO:33), ADR4-22 (SEQ ID NO:34), or ADR4-23 (SEQ ID NO:35).

40. The dAb according to claim 1, wherein the dAb has an amino acid sequence that differs from the amino acid sequence of ADR4-2 (SEQ ID NO:14), ADR4-3 (SEQ ID NO:15), ADR4-4 (SEQ ID NO:16), ADR4-6 (SEQ ID NO:18), ADR4-7 (SEQ ID NO:19), ADR4-9 (SEQ ID NO:21), ADR4-10 (SEQ ID NO:22), ADR4-11 (SEQ ID NO:23), ADR4-12 (SEQ ID NO:24), ADR4-13 (SEQ ID NO:25), ADR4-14 (SEQ ID NO:26), ADR4-15 (SEQ ID NO:27), ADR4-16 (SEQ ID NO:28), ADR4-17 (SEQ ID NO:29), ADR4-18 (SEQ ID NO:30), ADR4-19 (SEQ ID NO:31), ADR4-20 (SEQ ID NO:32), ADR4-21 (SEQ ID NO:33), ADR4-22 (SEQ ID NO:34), or ADR4-23 (SEQ ID NO:35) at no more than 25 amino acid positions, has a CDR1 sequence that has at least 50% identity to the CDR1 sequence of ADR4-2 (SEQ ID NO:14), ADR4-3 (SEQ ID NO:15), ADR4-4 (SEQ ID NO:16), ADR4-5 (SEQ ID NO:17), ADR4-6 (SEQ ID NO:18), ADR4-7 (SEQ ID NO:19), ADR4-8 (SEQ ID NO:20), ADR4-9 (SEQ ID NO:21), ADR4-10 (SEQ ID NO:22), ADR4-11 (SEQ ID NO:23), ADR4-12 (SEQ ID NO:24), ADR4-13 (SEQ ID NO:25), ADR4-14 (SEQ ID NO:26), ADR4-15 (SEQ ID NO:27), ADR4-16 (SEQ ID NO:28), ADR4-17 (SEQ ID NO:29), ADR4-18 (SEQ ID NO:30), ADR4-19 (SEQ ID NO:31), ADR4-20 (SEQ ID NO:32), ADR4-21 (SEQ ID NO:33), ADR4-22 (SEQ ID NO:34), or ADR4-23 (SEQ ID NO:35), and has a CDR2 sequence that has at least 50% identity to the CDR2 sequence of ADR4-2 (SEQ ID NO:14), ADR4-3 (SEQ ID NO:15), ADR4-4 (SEQ ID NO:16), ADR4-5 (SEQ ID NO:17), ADR4-6 (SEQ ID NO:18), ADR4-7 (SEQ ID NO:19), ADR4-8 (SEQ ID NO:20), ADR4-9 (SEQ ID NO:21), ADR4-10 (SEQ ID NO:22), ADR4-11 (SEQ ID NO:23), ADR4-12 (SEQ ID NO:24), ADR4-13 (SEQ ID NO:25), ADR4-14 (SEQ ID NO:26), ADR4-15 (SEQ ID NO:27), ADR4-16 (SEQ ID NO:28), ADR4-17 (SEQ ID NO:29), ADR4-18 (SEQ ID NO:30), ADR4-19 (SEQ ID NO:31), ADR4-20 (SEQ ID NO:32), ADR4-21 (SEQ ID NO:33), ADR4-22 (SEQ ID NO:34), or ADR4-23 (SEQ ID NO:35).

41. The dAb according to claim 1, wherein the dAb has an amino acid sequence that differs from the amino acid sequence of ADR4-2 (SEQ ID NO:14), ADR4-3 (SEQ ID NO:15), ADR4-4 (SEQ ID NO:16), ADR4-6 (SEQ ID NO:18), ADR4-7 (SEQ ID NO:19), ADR4-9 (SEQ ID NO:21), ADR4-10 (SEQ ID NO:22), ADR4-11 (SEQ ID NO:23), ADR4-12 (SEQ ID NO:24), ADR4-13 (SEQ ID NO:25), ADR4-14 (SEQ ID NO:26), ADR4-15 (SEQ ID NO:27), ADR4-16 (SEQ ID NO:28), ADR4-17 (SEQ ID NO:29), ADR4-18 (SEQ ID NO:30), ADR4-19 (SEQ ID NO:31), ADR4-20 (SEQ ID NO:32), ADR4-21 (SEQ ID NO:33), ADR4-22 (SEQ ID NO:34), or ADR4-23 (SEQ ID NO:35) at no more than 25 amino acid positions, has a CDR2 sequence that has at least 50% identity to the CDR2 sequence of ADR4-2 (SEQ ID NO:14), ADR4-3 (SEQ ID NO:15), ADR4-4 (SEQ ID NO:16), ADR4-5 (SEQ ID NO:17), ADR4-6 (SEQ ID NO:18), ADR4-7 (SEQ ID NO:19), ADR4-8 (SEQ ID NO:20), ADR4-9 (SEQ ID NO:21), ADR4-10 (SEQ ID NO:22), ADR4-11 (SEQ ID NO:23), ADR4-12 (SEQ ID NO:24), ADR4-13 (SEQ ID NO:25), ADR4-14 (SEQ ID NO:26), ADR4-15 (SEQ ID NO:27), ADR4-16 (SEQ ID NO:28), ADR4-17 (SEQ ID NO:29), ADR4-18 (SEQ ID NO:30), ADR4-19 (SEQ ID NO:31), ADR4-20 (SEQ ID NO:32), ADR4-21 (SEQ ID NO:33), ADR4-22 (SEQ ID NO:34), or ADR4-23 (SEQ ID NO:35), and has a CDR3 sequence that has at least 50% identity to the CDR3 sequence of ADR4-2 (SEQ ID NO:14), ADR4-3 (SEQ ID NO:15), ADR4-4 (SEQ ID NO:16), ADR4-5 (SEQ ID NO:17), ADR4-6 (SEQ ID NO:18), ADR4-7 (SEQ ID NO:19), ADR4-8 (SEQ ID NO:20), ADR4-9 (SEQ ID NO:21), ADR4-10 (SEQ ID NO:22), ADR4-11 (SEQ ID NO:23), ADR4-12 (SEQ ID NO:24), ADR4-13 (SEQ ID NO:25), ADR4-14 (SEQ ID NO:26), ADR4-15 (SEQ ID NO:27), ADR4-16 (SEQ ID NO:28), ADR4-17 (SEQ ID NO:29), ADR4-18 (SEQ ID NO:30), ADR4-19 (SEQ ID NO:31), ADR4-20 (SEQ ID NO:32), ADR4-21 (SEQ ID NO:33), ADR4-22 (SEQ ID NO:34), or ADR4-23 (SEQ ID NO:35).

42. The dAb according to claim 1, wherein the dAb has an amino acid sequence that differs from the amino acid sequence of ADR4-2 (SEQ ID NO:14), ADR4-3 (SEQ ID NO:15), ADR4-4 (SEQ ID NO:16), ADR4-6 (SEQ ID NO:18), ADR4-7 (SEQ ID NO:19), ADR4-9 (SEQ ID NO:21), ADR4-10 (SEQ ID N0:22), ADR4-11 (SEQ ID N0:23), ADR4-12 (SEQ ID N0:24), ADR4-13 (SEQ ID N0:25), ADR4-14 (SEQ ID N0:26), ADR4-15 (SEQ ID N0:27), ADR4-16 (SEQ ID N0:28), ADR4-17 (SEQ ID N0:29), ADR4-18 (SEQ ID N0:30), ADR4-19 (SEQ ID NO:31), ADR4-20 (SEQ ID N0:32), ADR4-21 (SEQ ID N0:33), ADR4-22 (SEQ ID N0:34), or ADR4-23 (SEQ ID N0:35) at no more than 25 amino acid positions, has a CDR1 sequence that has at least 50% identity to the CDR1 sequence of ADR4-2 (SEQ ID NO:14), ADR4-3 (SEQ ID NO:15), ADR4-4 (SEQ ID NO:16), ADR4-6 (SEQ ID NO:18), ADR4-7 (SEQ ID NO:19), ADR4-9 (SEQ ID NO:21), ADR4-10 (SEQ ID N0:22), ADR4-11 (SEQ ID N0:23), ADR4-12 (SEQ ID N0:24), ADR4-13 (SEQ ID N0:25), ADR4-14 (SEQ ID N0:26), ADR4-15 (SEQ ID N0:27), ADR4-16 (SEQ ID N0:28), ADR4-17 (SEQ ID N0:29), ADR4-18 (SEQ ID N0:30), ADR4-19 (SEQ ID N0:31), ADR4-20 (SEQ ID N0:32), ADR4-21 (SEQ ID N0:33), ADR4-22 (SEQ ID N0:34), or ADR4-23 (SEQ ID N0:35), and has a CDR3 sequence that has at least 50% identity to the CDR3 sequence of ADR4-2 (SEQ ID NO:14), ADR4-3 (SEQ ID NO:15), ADR4-4 (SEQ ID NO:16), ADR4-5 (SEQ ID NO:17), ADR4-6 (SEQ ID N0:18), ADR4-7 (SEQ ID N0:19), ADR4-8 (SEQ ID N0:20), ADR4-9 (SEQ ID N0:21), ADR4-10 (SEQ ID N0:22), ADR4-11 (SEQ ID N0:23), ADR4-12 (SEQ ID N0:24), ADR4-13 (SEQ ID N0:25), ADR4-14 (SEQ ID N0:26), ADR4-15 (SEQ ID N0:27), ADR4-16 (SEQ ID N0:28), ADR4-17 (SEQ ID N0:29), ADR4-18 (SEQ ID N0:30), ADR4-19 (SEQ ID N0:31), ADR4-20 (SEQ ID N0:32), ADR4-21 (SEQ ID N0:33), ADR4-22 (SEQ ID N0:34), or ADR4-23 (SEQ ID NO:35).

43. The dAb according to claim 1, wherein the dAb has an amino acid sequence that differs from the amino acid sequence of ADR4-2 (SEQ ID NO:14), ADR4-3 (SEQ ID NO:15), ADR4-4 (SEQ ID NO:16), ADR4-6 (SEQ ID NO:18), ADR4-7 (SEQ ID NO:19), ADR4-9 (SEQ ID NO:21), ADR4-10 (SEQ ID NO:22), ADR4-11 (SEQ ID NO:23), ADR4-12 (SEQ ID NO:24), ADR4-13 (SEQ ID NO:25), ADR4-14 (SEQ ID NO:26), ADR4-15 (SEQ ID NO:27), ADR4-16 (SEQ ID NO:28), ADR4-17 (SEQ ID NO:29), ADR4-18 (SEQ ID NO:30), ADR4-19 (SEQ ID NO:31), ADR4-20 (SEQ ID NO:32), ADR4-21 (SEQ ID NO:33), ADR4-22 (SEQ ID NO:34), or ADR4-23 (SEQ ID NO:35) at no more than 25 amino acid positions, has a CDR1 sequence that has at least 50% identity to the CDR1 sequence of ADR4-2 (SEQ ID NO:14), ADR4-3 (SEQ ID NO:15), ADR4-4 (SEQ ID NO:16), ADR4-5 (SEQ ID NO:17), ADR4-6 (SEQ ID NO:18), ADR4-7 (SEQ ID NO:19), ADR4-8 (SEQ ID NO:20), ADR4-9 (SEQ ID NO:21), ADR4-10 (SEQ ID NO:22), ADR4-11 (SEQ ID NO:23), ADR4-12 (SEQ ID NO:24), ADR4-13 (SEQ ID NO:25), ADR4-14 (SEQ ID NO:26), ADR4-15 (SEQ ID NO:27), ADR4-16 (SEQ ID NO:28), ADR4-17 (SEQ ID NO:29), ADR4-18 (SEQ ID NO:30), ADR4-19 (SEQ ID NO:31), ADR4-20 (SEQ ID NO:32), ADR4-21 (SEQ ID NO:33), ADR4-22 (SEQ ID NO:34), or ADR4-23 (SEQ ID NO:35), has a CDR2 sequence that has at least 50% identity to the CDR2 sequence of ADR4-2 (SEQ ID NO:14), ADR4-3 (SEQ ID NO:15), ADR4-4 (SEQ ID NO:16), ADR4-6 (SEQ ID NO:18), ADR4-7 (SEQ ID NO:19), ADR4-9 (SEQ ID NO:21), ADR4-10 (SEQ ID NO:22), ADR4-11 (SEQ ID NO:23), ADR4-12 (SEQ ID NO:24), ADR4-13 (SEQ ID NO:25), ADR4-14 (SEQ ID NO:26), ADR4-15 (SEQ ID NO:27), ADR4-16 (SEQ ID NO:28), ADR4-17 (SEQ ID NO:29), ADR4-18 (SEQ ID NO:30), ADR4-19 (SEQ ID NO:31), ADR4-20 (SEQ ID NO:32), ADR4-21 (SEQ ID NO:33), ADR4-22 (SEQ ID NO:34), or ADR4-23 (SEQ ID NO:35), and has a CDR3 sequence that has at least 50% identity to the CDR3 sequence of ADR4-2 (SEQ ID NO:14), ADR4-3 (SEQ ID NO:15), ADR4-4 (SEQ ID NO:16), ADR4-5 (SEQ ID NO:17), ADR4-6 (SEQ ID NO:18), ADR4-7 (SEQ ID NO:19), ADR4-8 (SEQ ID NO:20), ADR4-9 (SEQ ID NO:21), ADR4-10 (SEQ ID NO:22), ADR4-11 (SEQ ID NO:23), ADR4-12 (SEQ ID NO:24), ADR4-13 (SEQ ID NO:25), ADR4-14 (SEQ ID NO:26), ADR4-15 (SEQ ID NO:27), ADR4-16 (SEQ ID NO:28), ADR4-17 (SEQ ID NO:29), ADR4-18 (SEQ ID NO:30), ADR4-19 (SEQ ID NO:31), ADR4-20 (SEQ ID NO:32), ADR4-21 (SEQ ID NO:33), ADR4-22 (SEQ ID NO:34), or ADR4-23 (SEQ ID NO:35).

44. The dAb according to claim 1, wherein the dAb has a CDR1 sequence that has at least 50% identity to the CDR1 sequence of ADR4-2 (SEQ ID NO:14), ADR4-3 (SEQ ID NO:15), ADR4-4 (SEQ ID NO:16), ADR4-6 (SEQ ID NO:18), ADR4-7 (SEQ ID NO:19), ADR4-9 (SEQ ID NO:21), ADR4-10 (SEQ ID NO:22), ADR4-11 (SEQ ID NO:23), ADR4-12 (SEQ ID NO:24), ADR4-13 (SEQ ID NO:25), ADR4-14 (SEQ ID NO:26), ADR4-15 (SEQ ID NO:27), ADR4-16 (SEQ ID NO:28), ADR4-17 (SEQ ID NO:29), ADR4-18 (SEQ ID NO:30), ADR4-19 (SEQ ID NO:31), ADR4-20 (SEQ ID NO:32), ADR4-21 (SEQ ID NO:33), ADR4-22 (SEQ ID NO:34), or ADR4-23 (SEQ ID NO:35).

45. The dAb according to claim 1, wherein the dAb has a CDR2 sequence that has at least 50% identity to the CDR2 sequence of ADR4-2 (SEQ ID NO:14), ADR4-3 (SEQ ID NO:15), ADR4-4 (SEQ ID NO:16), ADR4-6 (SEQ ID NO:18), ADR4-7 (SEQ ID NO:19), ADR4-9 (SEQ ID NO:21), ADR4-10 (SEQ ID NO:22), ADR4-11 (SEQ ID NO:23), ADR4-12 (SEQ ID NO:24), ADR4-13 (SEQ ID NO:25), ADR4-14 (SEQ ID NO:26), ADR4-15 (SEQ ID NO:27), ADR4-16 (SEQ ID NO:28), ADR4-17 (SEQ ID NO:29), ADR4-18 (SEQ ID NO:30), ADR4-19 (SEQ ID NO:31), ADR4-20 (SEQ ID NO:32), ADR4-21 (SEQ ID NO:33), ADR4-22 (SEQ ID NO:34), or ADR4-23 (SEQ ID NO:35).

46. The dAb according to claim 1, wherein the dAb has a CDR3 sequence that has at least 50% identity to the CDR3 sequence of ADR4-2 (SEQ ID NO:14), ADR4-3 (SEQ ID NO:15), ADR4-4 (SEQ ID NO:16), ADR4-6 (SEQ ID NO:18), ADR4-7 (SEQ ID NO:19), ADR4-9 (SEQ ID NO:21), ADR4-10 (SEQ ID NO:22), ADR4-11 (SEQ ID NO:23), ADR4-12 (SEQ ID NO:24), ADR4-13 (SEQ ID NO:25), ADR4-14 (SEQ ID NO:26), ADR4-15 (SEQ ID NO:27), ADR4-16 (SEQ ID NO:28), ADR4-17 (SEQ ID NO:29), ADR4-18 (SEQ ID NO:30), ADR4-19 (SEQ ID NO:31), ADR4-20 (SEQ ID NO:32), ADR4-21 (SEQ ID NO:33), ADR4-22 (SEQ ID NO:34), or ADR4-23 (SEQ ID NO:35).

47. The dAb according to claim 1, comprising a half-life extension moiety.

48. The dAb according to claim 47, wherein the half-life extension moiety is a PEG.

49. The dAb according to claim 47, wherein the half-life extension moiety binds to serum albumin.

50. The dAb according to claim 12, wherein the *Candida* spp. is one or more of those selected from the group consisting of: *Candida albicans, Candida tropicalis, Candida glabrata, Candida parapsilosis, Candida krusei* and *Candida lusitaniae*.

51. The pharmaceutical composition according to claim 12 comprising one or more dAbs which inhibit the functional activity of MP65 and one or more dAbs which inhibit the functional activity of Sap2.

52. The pharmaceutical composition of claim 12, wherein the dAb which binds to MP protein comprises an amino acid sequence selected from the group consisting of ADR3-1 (SEQ ID NO:5), ADR3-2 (SEQ ID NO:6), ADR3-3 (SEQ ID NO:7), ADR3-4 (SEQ ID NO:8), ADR3-5 (SEQ ID NO:9), ADR3-6 (SEQ ID NO:10), ADR3-7 (SEQ ID NO:11), ADR3-8 (SEQ ID NO:12) and ADR3-9 (SEQ ID NO:13).

53. The method of claim 13, wherein the dAb which binds to MP protein comprises an amino acid sequence selected from the group consisting of ADR3-1 (SEQ ID NO:5), ADR3-2 (SEQ ID NO:6), ADR3-3 (SEQ ID NO:7), ADR3-4 (SEQ ID NO:8), ADR3-5 (SEQ ID NO:9), ADR3-6 (SEQ ID NO:10), ADR3-7 (SEQ ID NO:11), ADR3-8 (SEQ ID NO:12) and ADR3-9 (SEQ ID NO:13).

54. The method of claim 26, wherein the dAb which binds to MP protein comprises an amino acid sequence selected from the group consisting of ADR3-1 (SEQ ID NO:5), ADR3-2 (SEQ ID NO:6), ADR3-3 (SEQ ID NO:7), ADR3-4 (SEQ ID NO:8), ADR3-5 (SEQ ID NO:9), ADR3-6 (SEQ ID NO:10), ADR3-7 (SEQ ID NO:11), ADR3-8 (SEQ ID NO:12) and ADR3-9 (SEQ ID NO:13).

55. The method of claim 30, wherein the dAb which binds to MP protein comprises an amino acid sequence selected from the group consisting of ADR3-1 (SEQ ID NO:5), ADR3-2 (SEQ ID NO:6), ADR3-3 (SEQ ID NO:7), ADR3-4 (SEQ ID NO:8), ADR3-5 (SEQ ID NO:9), ADR3-6 (SEQ ID NO:10), ADR3-7 (SEQ ID NO:11), ADR3-8 (SEQ ID NO:12) and ADR3-9 (SEQ ID NO:13).

56. The method of claim 36, wherein the dAb which binds to MP protein comprises an amino acid sequence selected from the group consisting of ADR3-1 (SEQ ID NO:5), ADR3-2 (SEQ ID NO:6), ADR3-3 (SEQ ID NO:7), ADR3-4 (SEQ ID NO:8), ADR3-5 (SEQ ID NO:9), ADR3-6 (SEQ ID NO:10), ADR3-7 (SEQ ID NO:11), ADR3-8 (SEQ ID NO:12) and ADR3-9 (SEQ ID NO:13).

* * * * *

UNITED STATES PATENT AND TRADEMARK OFFICE
CERTIFICATE OF CORRECTION

PATENT NO. : 8,092,800 B2  
APPLICATION NO. : 11/886492  
DATED : January 10, 2012  
INVENTOR(S) : Cassone et al.

Page 1 of 1

It is certified that error appears in the above-identified patent and that said Letters Patent is hereby corrected as shown below:

In Column 2, line 34, please delete "100 M to 1 μM." and replace with --100 μM to 1 pM.--.

In Column 3, line 27, please delete "1 μM" and replace with --1 pM.--.

In Column 6, line 38, please insert --or-- between "SEQ ID No 35" and "ADR3-1,".

In Column 6, line 47, please insert --or-- between "respectively" and "ADR3-1,".

In Column 6, line 66, please insert --or-- between "SEQ ID No 35" and "ADR3-1,".

In Column 7, line 8, please insert --or-- between "respectively" and "ADR3-1,".

In Column 7, line 27, please insert --or-- between "SEQ ID No 35" and "ADR3-1,".

In Column 7, line 36, please insert --or-- between "respectively" and "ADR3-1,".

In Column 8, line 29, please delete "CDR" and replace with --CDR2--.

In Column 10, line 13, please delete "and designated" and replace with --or ADR3-1, ADR3-2, ADR3-3, ADR3-4,--.

In Column 14, line 67, please delete "1 μM." and replace with --1 pM.--.

In Column 15, line 24, please delete "1 μM." and replace with --1 pM.--.

Signed and Sealed this  
Twelfth Day of June, 2012

David J. Kappos  
*Director of the United States Patent and Trademark Office*